(12) United States Patent
Demers et al.

(10) Patent No.: US 8,926,294 B2
(45) Date of Patent: Jan. 6, 2015

(54) PUMPING CASSETTE

(71) Applicant: DEKA Products Limited Partnership, Manchester, NH (US)

(72) Inventors: Jason A. Demers, Manchester, NH (US); Michael J. Wilt, Windham, NH (US); Kevin L. Grant, Litchfield, NH (US); James D. Dale, Nashua, NH (US); Brian D. Tracey, Litchfield, NH (US)

(73) Assignee: DEKA Products Limited Partnership, Manchester, NH (US)

(*) Notice: Subject to any disclaimer, the term of this patent is extended or adjusted under 35 U.S.C. 154(b) by 0 days.

(21) Appl. No.: 13/684,995

(22) Filed: Nov. 26, 2012

(65) Prior Publication Data

US 2013/0177457 A1   Jul. 11, 2013

Related U.S. Application Data

(63) Continuation of application No. 11/871,712, filed on Oct. 12, 2007, now Pat. No. 8,317,492.

(60) Provisional application No. 60/904,024, filed on Feb. 27, 2007, provisional application No. 60/921,314, filed on Apr. 2, 2007.

(51) Int. Cl.
*F04B 45/00* (2006.01)
*F04B 43/06* (2006.01)
*F04B 43/00* (2006.01)
*F04B 9/109* (2006.01)
*F04B 13/02* (2006.01)

(52) U.S. Cl.
CPC ............. *F04B 43/00* (2013.01); *F04B 9/109* (2013.01); *F04B 13/02* (2013.01)
USPC .......................................... 417/395; 210/646

(58) Field of Classification Search
CPC .... F04B 7/0275; F04B 9/109; F04B 11/0091; F04B 13/02; F04B 39/0072; F04B 43/023; F04B 45/041
USPC .............. 417/323, 379, 392, 394, 395, 413.1, 417/439, 440, 442, 479, 521; 210/645, 646; 604/6.11
See application file for complete search history.

(56) References Cited

U.S. PATENT DOCUMENTS 2,529,028 A   11/1950   Landon
2,816,514 A   12/1957   Freese (Continued)

FOREIGN PATENT DOCUMENTS

DE   33 28 744 A1   2/1985
EP   0 687 474 A1   12/1995

(Continued)

OTHER PUBLICATIONS

Office Action for CN Application No. 200880013766.6 filed Feb. 26, 2008, published as CN 101678159 on Mar. 24, 2010, which Office Action is dated Mar. 23, 2012, and claims as pending for CN Application No. 200880013766.6 as of Mar. 23, 2012.

(Continued)

*Primary Examiner* — Bryan Lettman
(74) *Attorney, Agent, or Firm* — Wold, Greenfield & Sacks, P.C.

(57) ABSTRACT

A pumping cassette including a housing having at least two inlet fluid lines and at least two outlet fluid lines. At least one balancing pod within the housing and in fluid connection with the fluid paths. The balancing pod balances the flow of a first fluid and the flow of a second fluid such that the volume of the first fluid equals the volume of the second fluid. The balancing pod also includes a membrane that forms two balancing chambers. Also included in the cassette is at least two reciprocating pressure displacement membrane pumps. The pumps are within the housing and they pump the fluid from a fluid inlet to a fluid outlet line and pump the second fluid from a fluid inlet to a fluid outlet.

10 Claims, 90 Drawing Sheets

(56) References Cited

U.S. PATENT DOCUMENTS

| | | |
|---|---|---|
| 3,200,648 A | 8/1965 | Waggaman |
| 3,508,656 A | 4/1970 | Serfass et al. |
| 3,539,081 A | 11/1970 | Norton et al. |
| 3,656,873 A | 4/1972 | Schiff |
| 3,759,483 A | 9/1973 | Baxter |
| RE27,849 E | 12/1973 | Wortman |
| 3,827,561 A | 8/1974 | Serfass et al. |
| 3,882,861 A | 5/1975 | Kettering et al. |
| 3,936,729 A | 2/1976 | Winslow |
| 4,096,211 A | 6/1978 | Rameau |
| 4,096,859 A | 6/1978 | Agarwal et al. |
| 4,155,852 A | 5/1979 | Fischel et al. |
| 4,161,264 A | 7/1979 | Malmgren et al. |
| 4,266,814 A | 5/1981 | Gallagher |
| 4,267,040 A | 5/1981 | Schal |
| 4,282,099 A | 8/1981 | Jones |
| 4,309,592 A | 1/1982 | Le Boeuf |
| 4,322,054 A | 3/1982 | Campbell |
| 4,362,156 A | 12/1982 | Feller et al. |
| 4,369,781 A | 1/1983 | Gilson et al. |
| 4,398,908 A | 8/1983 | Siposs |
| 4,439,188 A | 3/1984 | Dennehey et al. |
| 4,441,357 A | 4/1984 | Kahn et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,490,254 A | 12/1984 | Gordon et al. |
| 4,501,405 A | 2/1985 | Usry |
| 4,574,876 A | 3/1986 | Aid |
| 4,585,442 A | 4/1986 | Mannes |
| 4,623,334 A | 11/1986 | Riddell |
| 4,623,450 A | 11/1986 | Vantard et al. |
| 4,664,891 A | 5/1987 | Cosentino et al. |
| 4,680,445 A | 7/1987 | Ogawa |
| 4,695,385 A | 9/1987 | Boag |
| 4,731,072 A | 3/1988 | Aid |
| 4,770,769 A | 9/1988 | Schael |
| 4,778,451 A | 10/1988 | Kamen |
| 4,784,495 A | 11/1988 | Jonsson et al. |
| 4,808,161 A | 2/1989 | Kamen |
| 4,822,343 A | 4/1989 | Beiser |
| 4,826,482 A | 5/1989 | Kamen |
| 4,828,543 A | 5/1989 | Weiss et al. |
| 4,833,329 A | 5/1989 | Quint et al. |
| 4,906,816 A | 3/1990 | van Leerdam |
| 4,927,411 A | 5/1990 | Pastrone et al. |
| 4,950,235 A | 8/1990 | Slate et al. |
| 4,971,700 A | 11/1990 | Tsuji et al. |
| 4,976,162 A | 12/1990 | Kamen |
| 4,997,570 A | 3/1991 | Polaschegg |
| 5,024,756 A | 6/1991 | Sternby |
| 5,033,513 A | 7/1991 | Bartholomew |
| 5,061,241 A | 10/1991 | Stephens, Jr. et al. |
| 5,062,774 A | 11/1991 | Kramer et al. |
| 5,074,838 A | 12/1991 | Kroyer |
| 5,088,515 A | 2/1992 | Kamen |
| 5,088,901 A | 2/1992 | Brauer |
| 5,100,554 A | 3/1992 | Polaschegg |
| 5,105,981 A | 4/1992 | Gehman |
| 5,110,447 A | 5/1992 | MacWilliams et al. |
| 5,110,477 A | 5/1992 | Howard et al. |
| 5,116,316 A | 5/1992 | Sertic et al. |
| 5,125,069 A | 6/1992 | O'Boyle |
| 5,178,182 A | 1/1993 | Kamen |
| 5,245,693 A | 9/1993 | Ford et al. |
| 5,247,434 A | 9/1993 | Peterson et al. |
| 5,267,956 A | 12/1993 | Beuchat |
| 5,278,072 A | 1/1994 | Wall et al. |
| 5,300,044 A | 4/1994 | Classey et al. |
| 5,306,242 A | 4/1994 | Joyce et al. |
| 5,324,422 A | 6/1994 | Colleran et al. |
| 5,326,476 A | 7/1994 | Grogan et al. |
| D350,823 S | 9/1994 | Lanigan |
| D350,850 S | 9/1994 | Angelini |
| 5,350,357 A | 9/1994 | Kamen et al. |
| 5,351,686 A | 10/1994 | Steuer et al. |
| 5,378,126 A | 1/1995 | Abrahamson et al. |
| 5,381,510 A | 1/1995 | Ford et al. |
| 5,385,540 A | 1/1995 | Abbott et al. |
| 5,395,316 A | 3/1995 | Martin |
| 5,410,255 A | 4/1995 | Bailey |
| 5,411,472 A | 5/1995 | Steg, Jr. et al. |
| 5,413,566 A | 5/1995 | Sevrain et al. |
| 5,420,962 A | 5/1995 | Bakke |
| 5,421,823 A | 6/1995 | Kamen et al. |
| 5,423,738 A | 6/1995 | Robinson et al. |
| 5,429,485 A | 7/1995 | Dodge |
| 5,431,626 A | 7/1995 | Bryant et al. |
| 5,438,510 A | 8/1995 | Bryant et al. |
| 5,441,231 A | 8/1995 | Payne et al. |
| 5,441,343 A | 8/1995 | Pylkki et al. |
| 5,441,636 A | 8/1995 | Chevallet et al. |
| 5,472,614 A | 12/1995 | Rossi |
| 5,474,683 A | 12/1995 | Bryant et al. |
| 5,476,444 A | 12/1995 | Keeling et al. |
| 5,482,440 A | 1/1996 | Dennehey et al. |
| 5,486,286 A | 1/1996 | Peterson et al. |
| 5,487,827 A | 1/1996 | Peterson et al. |
| 5,496,273 A | 3/1996 | Pastrone et al. |
| 5,527,507 A | 6/1996 | Childers et al. |
| 5,541,344 A | 7/1996 | Becker et al. |
| 5,542,919 A | 8/1996 | Simon et al. |
| 5,558,255 A | 9/1996 | Sancoff et al. |
| 5,575,310 A | 11/1996 | Kamen et al. |
| 5,578,012 A | 11/1996 | Kamen et al. |
| 5,580,460 A | 12/1996 | Polaschegg |
| 5,586,438 A | 12/1996 | Fahy et al. |
| 5,591,344 A | 1/1997 | Kenley et al. |
| 5,593,290 A * | 1/1997 | Greisch et al. ............... 417/478 |
| 5,628,908 A | 5/1997 | Kamen et al. |
| 5,632,894 A | 5/1997 | White et al. |
| 5,634,896 A | 6/1997 | Bryant et al. |
| 5,645,531 A | 7/1997 | Thompson et al. |
| 5,651,765 A | 7/1997 | Haworth et al. |
| 5,651,893 A | 7/1997 | Kenley et al. |
| 5,651,898 A | 7/1997 | Imura |
| 5,690,831 A | 11/1997 | Kenley et al. |
| 5,692,729 A | 12/1997 | Harhen |
| 5,729,653 A | 3/1998 | Magliochetti et al. |
| 5,730,720 A | 3/1998 | Sites et al. |
| 5,744,027 A | 4/1998 | Connell et al. |
| 5,755,275 A | 5/1998 | Rose et al. |
| 5,755,683 A | 5/1998 | Houle et al. |
| 5,776,091 A | 7/1998 | Brugger et al. |
| 5,782,508 A | 7/1998 | Bartholomew |
| 5,797,897 A | 8/1998 | Jepson et al. |
| 5,875,282 A | 2/1999 | Jordan et al. |
| 5,879,316 A | 3/1999 | Safar et al. |
| 5,882,047 A | 3/1999 | Ostrander et al. |
| 5,899,873 A | 5/1999 | Jones et al. |
| 5,902,476 A | 5/1999 | Twardowski et al. |
| 5,931,648 A | 8/1999 | Del Canizo |
| 5,932,103 A | 8/1999 | Kenley et al. |
| 5,932,110 A | 8/1999 | Shah et al. |
| 5,938,634 A | 8/1999 | Packard |
| 5,947,931 A | 9/1999 | Bierman et al. |
| 5,989,423 A | 11/1999 | Kamen et al. |
| 6,041,801 A | 3/2000 | Gray et al. |
| 6,042,784 A | 3/2000 | Wamsiedler et al. |
| 6,047,108 A | 4/2000 | Sword et al. |
| 6,062,068 A | 5/2000 | Bowling et al. |
| 6,070,761 A | 6/2000 | Bloom et al. |
| 6,101,406 A | 8/2000 | Hacker et al. |
| 6,109,881 A | 8/2000 | Snodgrass et al. |
| 6,136,201 A | 10/2000 | Shah et al. |
| 6,139,819 A | 10/2000 | Unger et al. |
| 6,142,164 A | 11/2000 | Wier et al. |
| 6,142,446 A | 11/2000 | Leinsing |
| 6,146,523 A | 11/2000 | Kenley et al. |
| 6,146,536 A | 11/2000 | Twardowski et al. |
| 6,153,102 A | 11/2000 | Kenley et al. |
| 6,159,192 A | 12/2000 | Fowles et al. |
| 6,171,261 B1 | 1/2001 | Niermann et al. |
| 6,176,904 B1 | 1/2001 | Gupta |

(56) References Cited

U.S. PATENT DOCUMENTS

| | | |
|---|---|---|
| 6,210,361 B1 | 4/2001 | Kamen et al. |
| 6,213,996 B1 | 4/2001 | Jepson et al. |
| 6,223,130 B1 | 4/2001 | Gray et al. |
| 6,234,997 B1 | 5/2001 | Kamen et al. |
| 6,274,303 B1 | 8/2001 | Wowk et al. |
| 6,277,272 B1 | 8/2001 | Nikaido et al. |
| 6,277,277 B1 | 8/2001 | Jacobi et al. |
| 6,284,131 B1 | 9/2001 | Hogard et al. |
| 6,302,653 B1 | 10/2001 | Bryant et al. |
| 6,321,597 B1 | 11/2001 | Demers et al. |
| 6,331,778 B1 | 12/2001 | Dailey et al. |
| 6,336,003 B1 | 1/2002 | Mitsunaga et al. |
| 6,336,911 B1 | 1/2002 | Westerbeck et al. |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck et al. |
| 6,413,233 B1 | 7/2002 | Sites et al. |
| 6,415,797 B1 | 7/2002 | Groth et al. |
| 6,416,293 B1 | 7/2002 | Bouchard et al. |
| 6,423,053 B1 | 7/2002 | Lee |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,491,656 B1 | 12/2002 | Morris |
| 6,497,676 B1 | 12/2002 | Childers et al. |
| 6,517,510 B1 | 2/2003 | Stewart et al. |
| 6,520,747 B2 | 2/2003 | Gray et al. |
| 6,527,758 B2 | 3/2003 | Ko et al. |
| 6,529,775 B2 | 3/2003 | Whitebook et al. |
| 6,535,689 B2 | 3/2003 | Augustine et al. |
| 6,539,172 B2 | 3/2003 | Akahane |
| 6,543,814 B2 | 4/2003 | Bartholomew |
| 6,579,253 B1 | 6/2003 | Burbank et al. |
| 6,579,496 B1 | 6/2003 | Fausset et al. |
| RE38,203 E | 7/2003 | Kelly |
| 6,595,944 B2 | 7/2003 | Balschat et al. |
| 6,595,948 B2 | 7/2003 | Suzuki et al. |
| 6,604,908 B1 | 8/2003 | Bryant et al. |
| 6,608,968 B2 | 8/2003 | Bakke |
| 6,660,974 B2 | 12/2003 | Faries, Jr. et al. |
| 6,663,353 B2 | 12/2003 | Lipscomb et al. |
| 6,663,359 B2 | 12/2003 | Gray |
| 6,673,314 B1 | 1/2004 | Burbank et al. |
| 6,709,417 B1 | 3/2004 | Houle et al. |
| 6,722,865 B2 | 4/2004 | Domroese |
| 6,723,062 B1 | 4/2004 | Westberg et al. |
| 6,726,656 B2 | 4/2004 | Kamen et al. |
| 6,743,201 B1 | 6/2004 | Doing et al. |
| 6,749,403 B2 | 6/2004 | Bryant et al. |
| 6,752,172 B2 | 6/2004 | Lauer |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,826,948 B1 | 12/2004 | Bhatti et al. |
| 6,860,866 B1 | 3/2005 | Graf et al. |
| 6,868,309 B1 | 3/2005 | Begelman |
| 6,877,713 B1 | 4/2005 | Gray et al. |
| 6,905,314 B2 | 6/2005 | Danby |
| 6,905,479 B1 | 6/2005 | Bouchard et al. |
| 6,929,751 B2 | 8/2005 | Bowman et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,083,719 B2 | 8/2006 | Bowman et al. |
| 7,122,210 B2 | 10/2006 | Elisabettini et al. |
| 7,124,996 B2 | 10/2006 | Clarke et al. |
| 7,147,613 B2 | 12/2006 | Burbank et al. |
| 7,168,334 B1 | 1/2007 | Drott et al. |
| 7,169,303 B2 | 1/2007 | Sullivan et al. |
| 7,175,397 B2 | 2/2007 | Claude et al. |
| 7,175,606 B2 | 2/2007 | Bowman et al. |
| 7,214,210 B2 | 5/2007 | Kamen et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,318,892 B2 | 1/2008 | Connell et al. |
| 7,410,294 B2 | 8/2008 | Shiraki et al. |
| 7,461,968 B2 | 12/2008 | Demers et al. |
| 7,465,285 B2 | 12/2008 | Hutchinson et al. |
| 7,488,448 B2 | 2/2009 | Wieting et al. |
| 7,500,962 B2 | 3/2009 | Childers et al. |
| 7,544,179 B2 | 6/2009 | Distler et al. |
| 7,559,524 B2 | 7/2009 | Gray et al. |
| 7,601,636 B2 | 10/2009 | Dumas |
| 7,632,078 B2 | 12/2009 | Demers et al. |
| 7,632,080 B2 | 12/2009 | Tracey et al. |
| 7,717,682 B2 | 5/2010 | Orr |
| 7,727,176 B2 | 6/2010 | Tonelli et al. |
| 7,744,553 B2 | 6/2010 | Kelly et al. |
| 7,776,301 B2 | 8/2010 | Comrie et al. |
| 7,794,141 B2 | 9/2010 | Perry et al. |
| 7,815,595 B2 | 10/2010 | Busby et al. |
| 7,867,214 B2 | 1/2011 | Childers et al. |
| 7,892,197 B2 | 2/2011 | Folden et al. |
| 7,896,830 B2 | 3/2011 | Gura et al. |
| 7,935,074 B2 | 5/2011 | Plahey et al. |
| 7,938,792 B2 | 5/2011 | Roger et al. |
| 7,967,022 B2 | 6/2011 | Grant et al. |
| 8,002,726 B2 | 8/2011 | Karoor et al. |
| 8,042,563 B2 | 10/2011 | Grant et al. |
| 8,246,826 B2 | 8/2012 | Wilt et al. |
| 8,273,049 B2 | 9/2012 | Demers et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Kamen et al. |
| 8,425,471 B2 | 4/2013 | Grant et al. |
| 8,459,292 B2 | 6/2013 | Wilt et al. |
| 8,491,184 B2 | 7/2013 | Kamen et al. |
| 8,499,780 B2 | 8/2013 | Wilt et al. |
| 8,545,698 B2 | 10/2013 | Wilt et al. |
| 8,562,834 B2 | 10/2013 | Kamen et al. |
| 8,721,879 B2 | 5/2014 | Van der Merwe et al. |
| 8,721,884 B2 | 5/2014 | Wilt et al. |
| 8,771,508 B2 | 7/2014 | Grant et al. |
| 2002/0056672 A1 | 5/2002 | Lyle et al. |
| 2002/0103453 A1 | 8/2002 | Burbank et al. |
| 2002/0150476 A1 | 10/2002 | Lucke et al. |
| 2002/0179505 A1 | 12/2002 | Rovatti et al. |
| 2002/0179595 A1 | 12/2002 | Nagele |
| 2002/0182090 A1 | 12/2002 | Gray |
| 2003/0114795 A1 | 6/2003 | Faries et al. |
| 2003/0194328 A1 | 10/2003 | Bryant et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0229302 A1 | 12/2003 | Robinson et al. |
| 2004/0009096 A1 | 1/2004 | Wellman |
| 2004/0019313 A1 | 1/2004 | Childers et al. |
| 2004/0091374 A1 | 5/2004 | Gray |
| 2004/0101026 A1 | 5/2004 | Nitta et al. |
| 2004/0136843 A1 | 7/2004 | Jahn et al. |
| 2004/0138607 A1 | 7/2004 | Burbank et al. |
| 2004/0249331 A1* | 12/2004 | Burbank et al. ............. 604/4.01 |
| 2004/0262917 A1 | 12/2004 | Sunohara et al. |
| 2005/0020958 A1 | 1/2005 | Paolini et al. |
| 2005/0045540 A1 | 3/2005 | Connell et al. |
| 2005/0069425 A1 | 3/2005 | Gray et al. |
| 2005/0069427 A1 | 3/2005 | Roemuss et al. |
| 2005/0095141 A1 | 5/2005 | Lanigan et al. |
| 2005/0095154 A1 | 5/2005 | Tracey et al. |
| 2005/0126998 A1 | 6/2005 | Childers |
| 2005/0130332 A1 | 6/2005 | Ishii et al. |
| 2005/0131332 A1 | 6/2005 | Kelly et al. |
| 2005/0230292 A1 | 10/2005 | Beden et al. |
| 2005/0234385 A1 | 10/2005 | Vandlik et al. |
| 2005/0242034 A1 | 11/2005 | Connell et al. |

(56) References Cited

U.S. PATENT DOCUMENTS

| | | |
|---|---|---|
| 2005/0274658 A1 | 12/2005 | Rosenbaum et al. |
| 2006/0002823 A1 | 1/2006 | Feldstein |
| 2006/0093531 A1 | 5/2006 | Tremoulet et al. |
| 2006/0184084 A1 | 8/2006 | Ware et al. |
| 2006/0195064 A1 | 8/2006 | Plahey et al. |
| 2006/0241550 A1 | 10/2006 | Kamen et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0166181 A1 | 7/2007 | Nilson |
| 2007/0253463 A1 | 11/2007 | Perry et al. |
| 2007/0278155 A1 | 12/2007 | Lo et al. |
| 2008/0015493 A1 | 1/2008 | Childers et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0204086 A1 | 8/2008 | Park et al. |
| 2008/0205481 A1 | 8/2008 | Faries et al. |
| 2008/0208103 A1 | 8/2008 | Demers et al. |
| 2008/0208111 A1 | 8/2008 | Kamen et al. |
| 2008/0215898 A1 | 9/2008 | Lu et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Knelp et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076434 A1 | 3/2009 | Mischelevich et al. |
| 2009/0095679 A1 | 4/2009 | Demers et al. |
| 2009/0101549 A1 | 4/2009 | Kamen et al. |
| 2009/0101550 A1 | 4/2009 | Muller et al. |
| 2009/0101566 A1 | 4/2009 | Crnkovich et al. |
| 2009/0105621 A1 | 4/2009 | Boyd et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0154524 A1 | 6/2009 | Girelli |
| 2009/0173682 A1 | 7/2009 | Robinson et al. |
| 2009/0182263 A1 | 7/2009 | Burbank et al. |
| 2009/0192367 A1 | 7/2009 | Braig et al. |
| 2009/0202367 A1 | 8/2009 | Gray et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0133153 A1 | 6/2010 | Beden et al. |
| 2010/0137782 A1 | 6/2010 | Jansson et al. |
| 2010/0185134 A1 | 7/2010 | Houwen et al. |
| 2010/0187176 A1 | 7/2010 | Lopez |
| 2010/0192686 A1 | 8/2010 | Kamen et al. |
| 2010/0296953 A1 | 11/2010 | Gray |
| 2010/0327849 A1 | 12/2010 | Kamen et al. |
| 2011/0009797 A1 | 1/2011 | Kelly et al. |
| 2011/0092875 A1 | 4/2011 | Beck et al. |
| 2011/0105877 A1 | 5/2011 | Wilt et al. |
| 2011/0218600 A1 | 9/2011 | Kamen et al. |
| 2011/0299358 A1 | 12/2011 | Wilt et al. |
| 2011/0303588 A1 | 12/2011 | Kelly et al. |
| 2011/0303598 A1 | 12/2011 | Lo et al. |
| 2012/0106289 A1 | 5/2012 | Wilt et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0126413 A1 | 5/2013 | Van der Merwe et al. |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Grant et al. |
| 2014/0199193 A1 | 7/2014 | Wilt et al. |

FOREIGN PATENT DOCUMENTS

| | | |
|---|---|---|
| EP | 0 815 882 A2 | 1/1998 |
| EP | 0 992 255 A2 | 4/2000 |
| EP | 2 319 551 A2 | 5/2011 |
| JP | 63-106445 U | 7/1988 |
| JP | 2005-526574 A | 9/2005 |
| JP | 2007-215557 A | 8/2007 |
| WO | 94/20158 A1 | 9/1994 |
| WO | 98/37801 A1 | 9/1998 |
| WO | 98/39058 A1 | 9/1998 |
| WO | WO 99/10028 A1 | 3/1999 |
| WO | 01/37895 A2 | 5/2001 |
| WO | 02/03879 A1 | 1/2002 |
| WO | 02/30267 A2 | 4/2002 |
| WO | 03/099354 A2 | 12/2003 |
| WO | 2004/041081 A1 | 5/2004 |
| WO | 2005/044339 A2 | 5/2005 |
| WO | WO 2005/044435 A2 | 5/2005 |
| WO | 2006/120415 A1 | 11/2006 |
| WO | 2007/120812 A2 | 10/2007 |
| WO | 2007/126360 A1 | 11/2007 |
| WO | 2008/106191 A2 | 9/2008 |
| WO | 2008/106452 A1 | 9/2008 |
| WO | 2008/106538 A2 | 9/2008 |
| WO | WO 2008/106440 A1 | 9/2008 |
| WO | 2008/118600 A1 | 10/2008 |
| WO | 2009/051669 A1 | 4/2009 |
| WO | 2009/094179 A2 | 7/2009 |
| WO | 2009/094183 A1 | 7/2009 |
| WO | 2010/027435 A1 | 3/2010 |
| WO | 2010/027437 A2 | 3/2010 |

OTHER PUBLICATIONS

International Search Report and Written Opinion for Application No. PCT/US2008/055000 mailed Aug. 1, 2008.

International Preliminary Report on Patentability for Application No. PCT/US2008/055000 mailed Sep. 11, 2009.

Office Action for U.S. Appl. No. 11/871,712 filed Oct. 12, 2007, published as US 2009/0004033 on Jan. 1, 2009, which Office Action is dated Feb. 4, 2010, and claims as pending for U.S. Appl. No. 11/871,712 as of Feb. 4, 2010.

(56) References Cited

OTHER PUBLICATIONS

Office Action for U.S. Appl. No. 11/871,712 filed Oct. 12, 2007, published as US 2009-0004033 on Jan. 1, 2009, which Office Action is dated Oct. 15, 2010, and claims as pending for U.S. Appl. No. 11/871,712 as of Oct. 15, 2010.
Office Action for U.S. Appl. No. 11/871,712 filed Oct. 12, 2007, published as US 2009-0004033 on Jan. 1, 2009, which Office Action is dated Feb. 7, 2011, and claims as pending for U.S. Appl. No. 11/871,712 as of Feb. 7, 2011.
Written Opinion for Application No. PCT/US2008/002636 mailed Jul. 2, 2008.
International Preliminary Report on Patentability for Application No. PCT/US2008/002636 mailed Sep. 11, 2009.
Invitation to Pay Additional Fees mailed Aug. 5, 2008 for Application No. PCT/US2008/055168.
International Search Report and Written Opinion mailed Nov. 10, 2008 for International Application No. PCT/US2008/055168.
International Preliminary Report on Patentability mailed Sep. 11, 2009 for International Application No. PCT/US2008/055168.
International Search Report and Written Opinion for Application No. PCT/US2008/055136 mailed Jul. 24, 2008.
International Preliminary Report on Patentability for Application No. PCT/US2008/055136 mailed Sep. 11, 2009.
Invitation to Pay Additional Fees mailed Nov. 27, 2009 for International Application No. PCT/US2009/004866.
International Search Report and Written Opinion mailed Jan. 27, 2010 for International Application No. PCT/US2009/004822.
International Preliminary Report on Patentability for Application No. PCT/US2009/004866 mailed Mar. 10, 2011.
Invitation to Pay Additional Fees mailed Dec. 8, 2009 for International Application No. PCT/US2009/004877.
International Search Report and Written Opinion mailed Feb. 12, 2010 for International Application No. PCT/US2009/004877.
International Preliminary Report on Patentability for Application No. PCT/US2009/004877 mailed Mar. 10, 2011.
Written Opinion mailed Aug. 17, 2007 for International Application No. PCT/US2007/009107.
International Preliminary Report on Patentability mailed Oct. 23, 2008 for International Application No. PCT/US2007/009107.
Partial European Search Report for Application No. 11150584.8 mailed Mar. 30, 2011.
Extended European Search Report for Application No. 11150584 8 mailed Jul. 26, 2011.
International Search Report and Written Opinion mailed Feb. 20, 2009 for International Application No. PCT/US2008/011663.
International Preliminary Report on Patentability mailed Apr. 22, 2010 for International Application No. PCT/US2008/011663.
Invitation to Pay Additional Fees for Application No. PCT/US2009/000433 mailed Jun. 4, 2009.
International Search Report and Written Opinion for Application No. PCT/US2009/000433 mailed Sep. 25, 2009.
International Preliminary Report on Patentability for Application No. PCT/US2009/000433 mailed Aug. 5, 2010.
International Search Report and Written Opinion mailed Jul. 23, 2008 for International Application No. PCT/US2008/0055021.
International Preliminary Report on Patentability mailed Sep. 11, 2009 for International Application No. PCT/US2008/055021.
Office Action for U.S. Appl. No. 12/072,908 filed Feb. 27, 2008, published as US 2009-0008331 on Jan. 8, 2009, which Office Action is dated Oct. 15, 2010, and claims as pending for U.S. Appl. No. 12/072,908 as of Oct. 15, 2010.
Office Action for U.S. Appl. No. 12/072,908 filed Feb. 27, 2008, published as US 2009-0008331 on Jan. 8, 2009 which Office Action is dated Jul. 15, 2011, and claims as pending for U.S. Appl. No. 12/072,908 as of Jul. 15, 2011.
Office Action for US Application No. 12/038,648 filed Feb. 27, 2008, published as US 2008-0216898 on Sep. 11, 2008, which Office Action is dated Oct. 1, 2010, and claims as pending for U.S. Appl. No. 12/038,648 as Oct. 1, 2010.
Ex Parte Quayle Action for U.S. Appl. No. 12/038,648 filed Feb. 27, 2008, published as 2008-0216898, on Sep. 11, 2008, which Office Action is dated Mar. 29, 2011, and claims as pending for U.S. Appl. No. 12/038,648 as of Mar. 29, 2011.
Office Action for U.S. Application No. 12/199,176 filed Aug. 27, 2008, published as 2010-0056975 on Mar. 4, 2010, which Office Action is dated Nov. 22, 2010, and claims as pending for U.S. Appl. No. 12/199,176 as of Nov. 22, 2010.
Office Action for U.S. Appl. No. 12/199,176 filed Aug. 27, 2008, published as 2010-0056975 on Mar. 4, 2010, which Office Action is dated Sep. 2, 2011, and claims as pending for U.S. Appl. No. 12/199,176 as of Sep. 2, 2011.
Office Action for U.S. Appl. No. 12/199,176 filed Aug. 27, 2008, published as 2010-0056975 on Mar. 4, 2010, which Office Action is dated Feb. 10, 2012, and claims as pending for U.S. Appl. No. 12/199,176 as of Feb. 10, 2012.
Office Action for U.S. Appl. No. 11/787,212 filed Apr. 13, 2007, published as US 2008-0175719 on Jul. 24, 2008, which Office Action is dated May 26, 2010, and claims as pending for U.S. Appl. No. 11/787,212 as of May 26, 2010.
Office Action for U.S. Appl. No. 11/787,212 filed Apr. 13, 2007, published as 2008-0175719 on Jul. 24, 2008, which Office Action is dated Feb. 7, 2011, and claims as pending for U.S. Appl. No. 11/787,212 as of Feb. 7, 2011.
Office Action for U.S. Appl. No. 11/787,213 filed Apr. 13, 2007, published as US 2008-0058697 on Mar. 6, 2008, which Office Action is dated Mar. 18, 2010, and claims as pending for U.S. Appl. No. 11/787,213 as of Mar. 18, 2010.
Office Action for U.S. Appl. No. 11/787,112 filed Apr. 13, 2007, published as US 2007/0253463 on Nov. 1, 2007, which Office Action is dated Nov. 21, 2008, and claims as pending for U.S. Appl. No. 11/787,112 as of Nov. 21, 2008.
Office Action for U.S. Appl. No. 11/871,821 filed Oct. 12, 2007, published as US 2008-0240929 on Oct. 2, 2008, which Office Action is dated Sep. 23, 2009, and claims as pending for U.S. Appl. No. 11/871,821 as of Sep. 23, 2009.
Office Action for U.S. Appl. No. 11/871,828 filed Oct. 12, 2007, published as US 2008-0208111 on Aug. 28, 2008, which Office Action is dated Mar. 11, 2010, and claims as pending for U.S. Appl. No. 11/871,828 as of Mar. 11, 2010.
Office Action for U.S. Appl. No. 11/871,828 filed Oct. 12, 2007, published as US 2008-0208111 on Aug. 28, 2008, which Office Action is dated Nov. 26, 2010, and claims as pending for U.S. Appl. No. 11/871,828 as of Nov. 26, 2010.
Bengtsson et al., Haemo dialysis software architecture design experiences. Proceedings of the 1999 International Conference on Software Engineering. ACM New York, NY. 1999:516-525.
Choppy et al., Architectural patterns for problem frames. IEE Proceedings: Software. Aug. 2005; 152(4):190-208.
Gentilini et al., Multitasked closed-loop control in anesthesia. IEEE Eng Med Biol Mag. Jan.-Feb. 2001; 20(1):39-53.
Harel, Statecharts: A visual formalism for complex systems. Science of Computer Programming. 1987; 8:231-274.
Krasner et al., A cookbook for using the model-view-controller user interface paradigm in smalltalk-80. JOOP. Aug. 1988; 1(3):26-49.

\* cited by examiner

1500

1600

1800

1900

2000

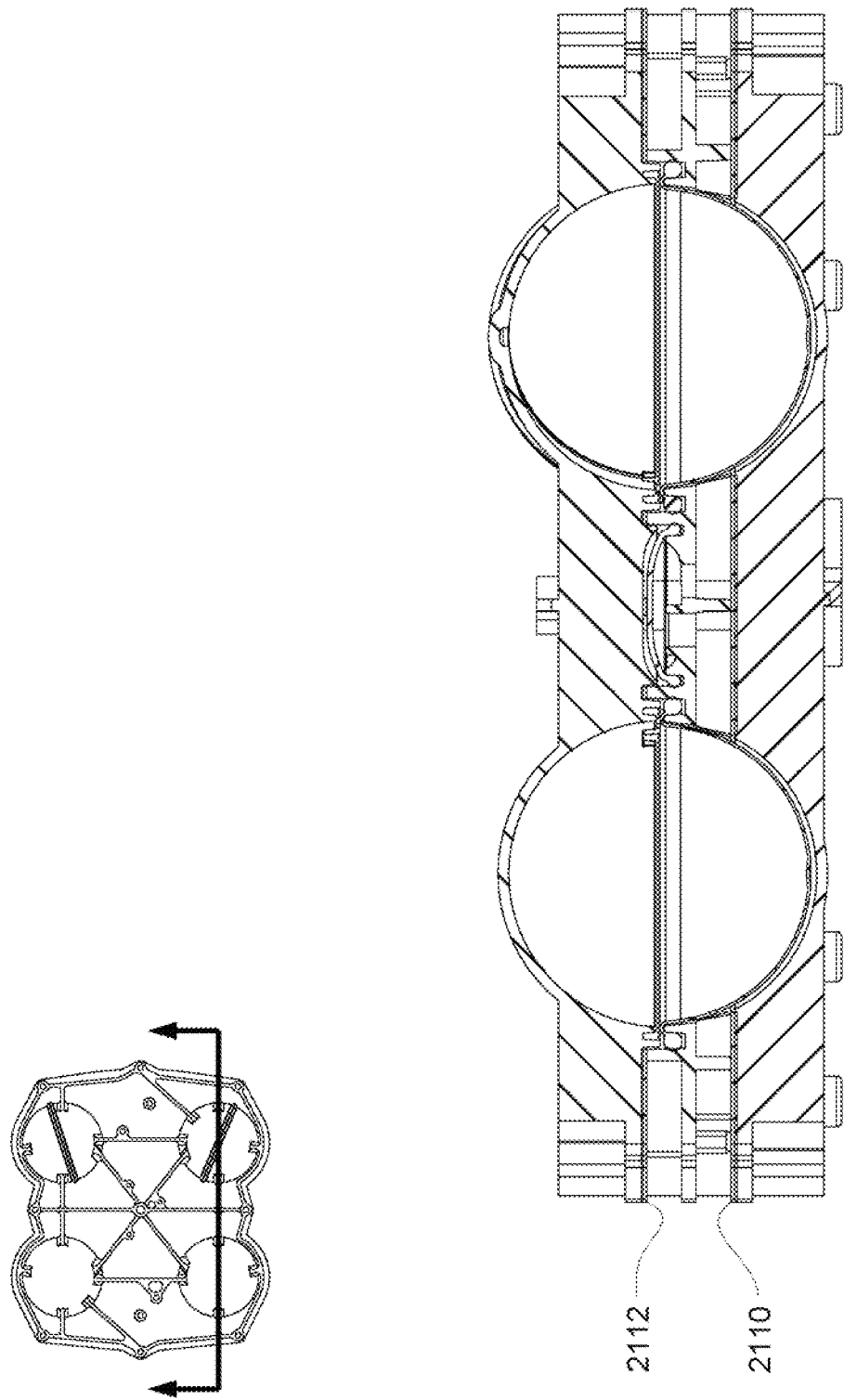

PUMPING CASSETTE

CROSS-REFERENCE TO RELATED APPLICATIONS

This application is a continuation of U.S. patent application Ser. No. 11/871,712, filed on Oct. 12, 2007 and issued on Nov. 27, 2012 as U.S. Pat. No. 8,317,492, which claims priority from the following U.S. Provisional Patent Applications:

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007. Each of the three above-indicated priority applications are hereby incorporated by reference in their entireties.

TECHNICAL FIELD

The present invention relates to a cassette for pumping fluid.

SUMMARY OF THE INVENTION

In accordance with one aspect of the pumping cassette, the cassette is a cassette including a housing having at least two inlet fluid lines and at least two outlet fluid lines. At least one balancing pod within the housing and in fluid connection with the fluid paths. The balancing pod balances the flow of a first fluid and the flow of a second fluid such that the volume of the first fluid equals the volume of the second fluid. The balancing pod also includes a membrane that forms two balancing chambers. Also included in the cassette is at least two reciprocating pressure displacement membrane pumps. The pumps are within the housing and they pump the fluid from a fluid inlet to a fluid outlet line and pump the second fluid from a fluid inlet to a fluid outlet.

Various embodiments of this aspect of the cassette include one or more of the following. Where the reciprocating pressure displacement pumps includes a curved rigid chamber wall and a flexible membrane attached to the rigid chamber wall. The flexible membrane and the rigid chamber wall define a pumping chamber. Also, where the cassette housing includes a top plate, midplate and a bottom plate. Also, where the cassette further includes a metering pump within the housing. The metering pump is fluidly connected to a fluid line and pumps a volume of a fluid. Also, where the pressure pump and the metering pump are pneumatically actuated pumps. Also, where the metering pump pumps a volume of a fluid such that the fluid bypasses the balancing chambers and the metering pump is a membrane pump. Also, where the cassette includes at least one fluid valve. Also, where the cassette includes at least two fluid valves actuated by one pneumatic valve.

In accordance with another aspect of the cassette is a cassette including a housing that includes at least one inlet fluid line and at least one outlet fluid line. The cassette also includes at least one balancing pod within the housing and in fluid connection with the fluid paths. The balancing pod balances the flow of a first fluid and the flow of a second fluid such that the volume of the first fluid equals the volume of the second fluid. The balancing pod includes a membrane wherein the membrane forms two chambers within the balancing pod. Also included in the cassette is at least one reciprocating pressure displacement membrane pump within the housing. The pressure pump pumps a fluid from the fluid inlet line to the fluid outlet line. A metering pump is also included within the housing. The metering pump is fluidly connected to a fluid line. The metering pump pumps a predetermined volume of a fluid such that the fluid bypasses the balancing chambers and wherein the metering pump is a membrane pump.

Various embodiments of this aspect of the cassette include one or more of the following. Where the reciprocating pressure displacement pumps includes a curved rigid chamber wall and a flexible membrane attached to the rigid chamber wall. The flexible membrane and the rigid chamber wall define a pumping chamber. Also, where the cassette housing includes a top plate, a midplate and a bottom plate. Also, where the cassette further includes a at least one fluid valve, and/or where the fluid valve is actuated by one pneumatic valve. Also, where the cassette includes at least two fluid valves actuated by one pneumatic valve.

In accordance with another aspect of the pumping cassette, the pumping cassette includes a housing that includes at least two inlet fluid lines and at least two outlet fluid lines. Also, at least two balancing pods within the housing and in fluid connection with the fluid lines. The balancing pods balance the flow of pure dialysate and impure dialysate such that the volume of pure dialysate equals the volume of impure dialysate. At least two reciprocating pressure displacement membrane pumps are also included in the housing. The pressure pumps pump the pure dialysate and said impure dialysate. A UF metering pump is also included within the housing. The UF metering pump pumps a predetermined volume of impure dialysate from the at least one fluid line such that the predetermined volume bypasses said balancing chamber.

Various embodiments of this aspect of the cassette include one or more of the following. Where the reciprocating pressure displacement pumps includes a curved rigid chamber wall and a flexible membrane attached to the rigid chamber wall. The flexible membrane and the rigid chamber wall define a pumping chamber. Also, where the cassette housing includes a top plate, a midplate and a bottom plate. Also, a plurality of pneumatically actuated fluid valves.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 22A shows a cross sectional view of the exemplary embodiment of the assembled cassette.

DETAILED DESCRIPTION OF SPECIFIC EMBODIMENTS

1. Pumping Cassette 1.1 Cassette

The pumping cassette include various features, namely, pod pumps, fluid lines and in some embodiment, valves. The cassette embodiments shown and described in this description include exemplary and some alternate embodiments. However, any variety of cassettes having a similar functionality is contemplated.

Figure 8A:
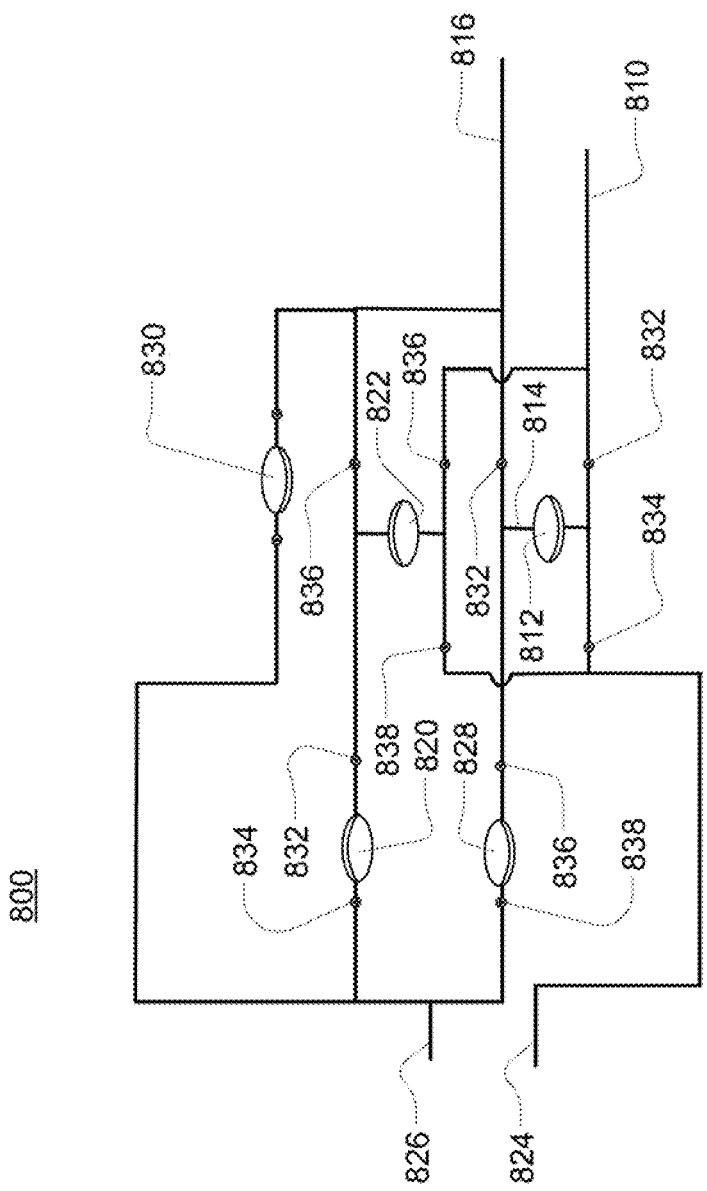
FIG. 8A is one embodiment of the fluid flow-path schematic of the cassette.
Figure 8B:
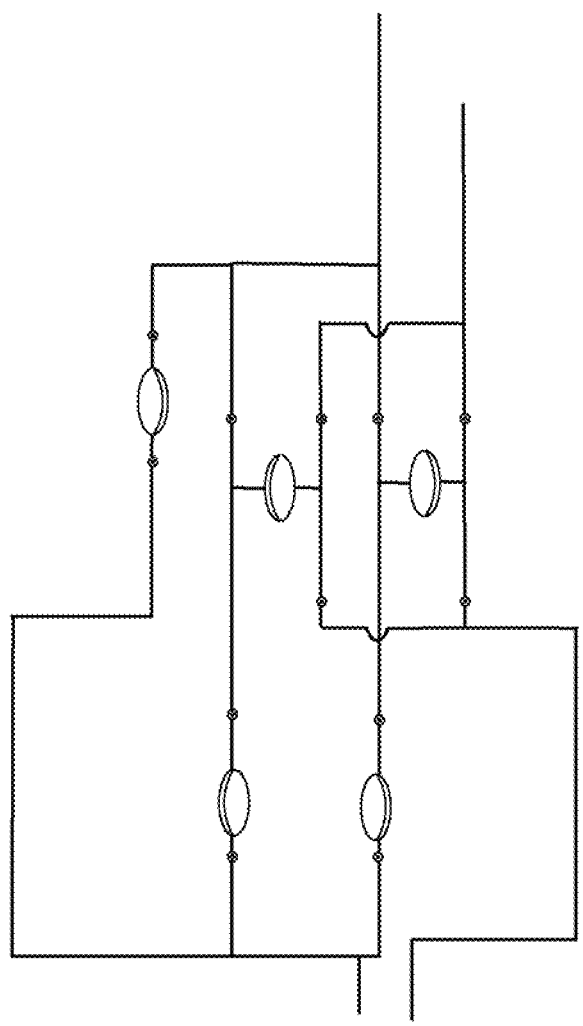
FIG. 8B is an alternate embodiment of the fluid flow-path schematic of the cassette.

As well, although the cassette embodiments described herein are implementations of the fluid schematics as shown in FIGS. 8A and 8B, in other embodiments, the cassette may have varying fluid paths and/or valve placement and/or pod pump placements and numbers and thus, is still within the scope of the invention.

In the exemplary embodiment, the cassette includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber).

In general, the membranes are located between the midplate and the bottom plate. However, with respect to balancing chambers, a portion of a membrane is located between the midplate and the top plate. Some embodiments include where the membrane is attached to the cassette, either overmolded, captured, bonded, press fit, welded in or any other process or method for attachment. However, in the exemplary embodiments, the membranes are separate from the top plate, midplate and bottom plate until the plates are assembled.

The cassettes may be constructed of a variety of materials. Generally, in the various embodiments, the materials used are solid and non flexible. In the preferred embodiment, the plates are constructed of polysulfone, but in other embodiments, the cassettes are constructed of any other solid material, and in exemplary embodiments, of any thermoplastic or thermosot. In some embodiments the cassettes are constructed of polycarbonate.

In the exemplary embodiment, the cassettes are formed by placing the membranes in their correct locations, assembling the plates in order, and connecting the plates. In one embodiment, the plates are connected using a laser welding technique. However, in other embodiments, the plates may be glued, mechanically fastened, strapped together, ultrasonically welded, or any other mode of attaching the plates together.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas. Thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow. Either or both may be used in various embodiments of the cassette.

The various fluid inlets and fluid outlets are fluid ports. In practice, depending on the valve arrangement and control, a fluid inlet can be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

1.2 Exemplary Pressure Pod Pump Embodiments

Figure 1A:
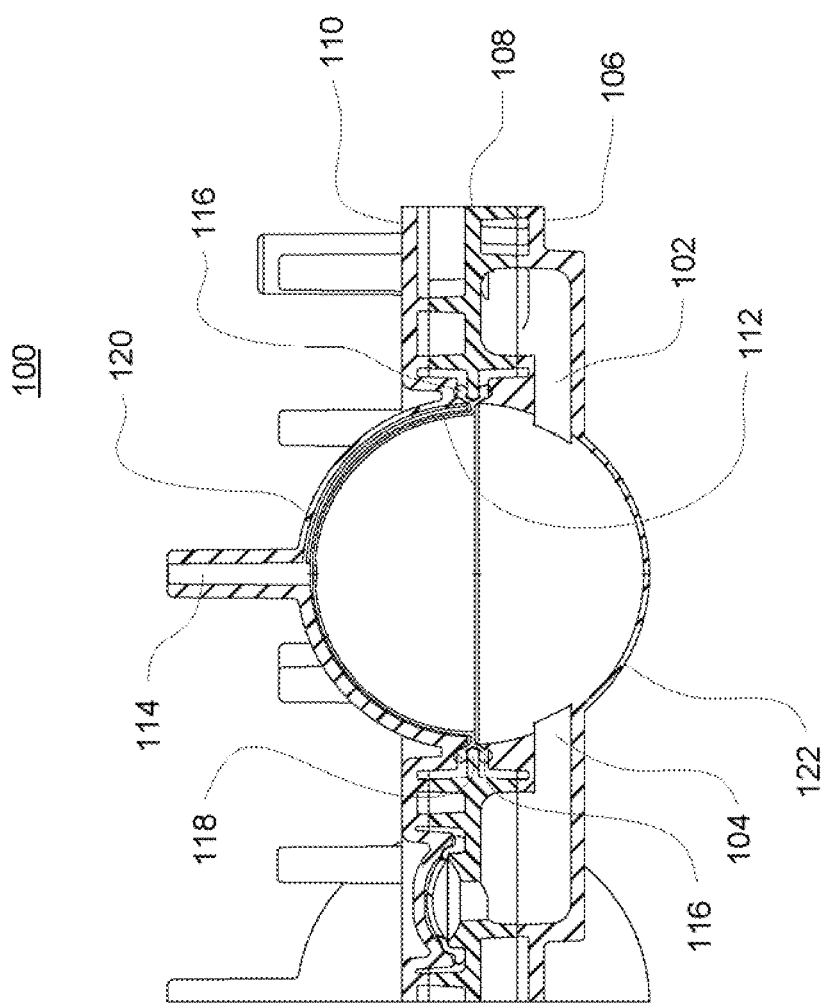
FIG. 1A is a sectional view of one embodiment of a pod pump that is incorporated into embodiments of the cassette.

FIG. 1A is a sectional view of an exemplary pod pump 100 that is incorporated into a fluid control or pump cassette (see also FIGS. 3 and 4), in accordance with an exemplary embodiment of the cassette. In this embodiment, the pod pump is formed from three rigid pieces, namely a "top" plate 106, a midplate 108, and a "bottom" plate 110 (it should be noted that the terms "top" and "bottom" are relative and are used here for convenience with reference to the orientation shown in FIG. 1A). The top and bottom plates 106 and 110 include generally hemispheroid portions that when assembled together define a hemispheroid chamber, which is a pod pump 100.

A membrane 112 separates the central cavity of the pod pump into two chambers. In one embodiment, these chambers are: the pumping chamber that receives the fluid to be pumped, and an actuation chamber for receiving the control gas that pneumatically actuates the pump. An inlet 102 allows fluid to enter the pumping chamber, and an outlet 104 allows fluid to exit the pumping chamber. The inlet 102 and the outlet 104 may be formed between midplate 108 and the top plate 106. Pneumatic pressure is provided through a pneumatic port 114 to either force, with positive gas pressure, the membrane 112 against one wall of pod pump cavity to minimize the pumping chamber's volume, or to draw, with negative gas pressure, the membrane 112 towards the other wall of the pod pump 100 cavity to maximize the pumping chamber's volume.

The membrane 112 is provided with a thickened rim 116, which is held tightly by a protrusion 118 in the midplate 108. Thus, in manufacture, the membrane 112 can be placed in and held by the groove 108 before the bottom plate 110 is connected (in the exemplary embodiment) to the midplate 108.

Figure 1B:
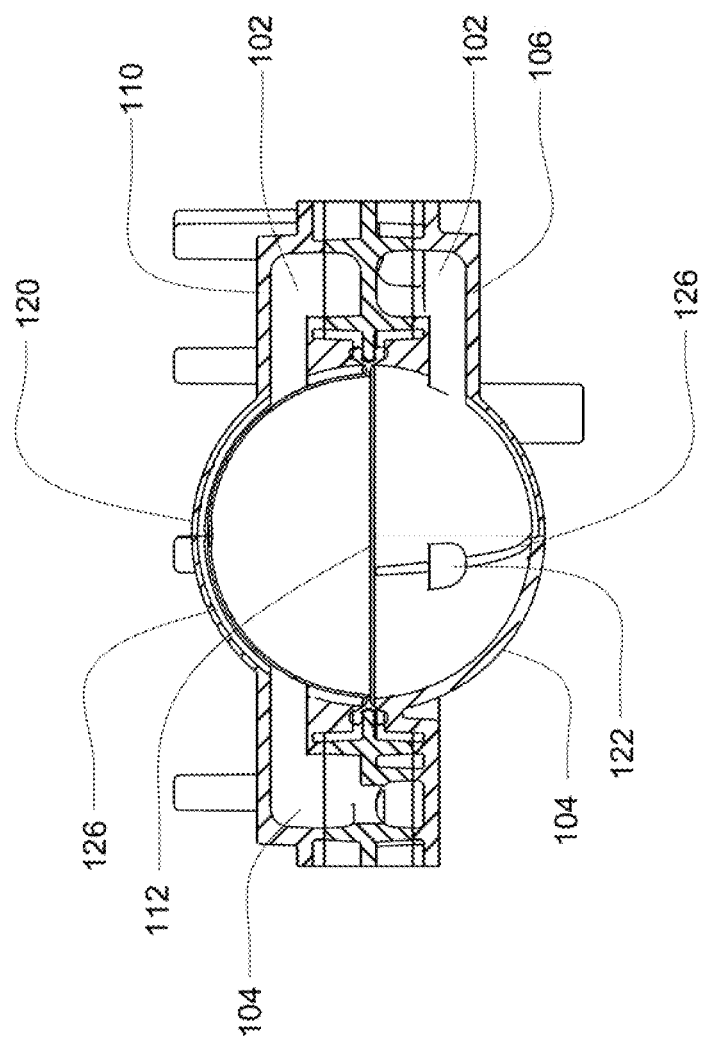
FIG. 1B is a sectional view of an exemplary embodiment of a pod pump that is incorporated into embodiments of the cassette.

Although not shown in FIGS. 1A and 1B, in some embodiments of the pod pump, on the fluid side, a groove is present on the chamber wall. The groove acts to prevent folds in the membrane from trapping fluid in the chamber when emptying.

Referring first to FIG. 1A, a cross sectional view of a reciprocating positive-displacement pump 100 in a cassette is shown. The pod pump 100 includes a flexible membrane 112 (also referred to as the "pump diaphragm" or "membrane") mounted where the pumping chamber (also referred to as a "liquid chamber" or "liquid pumping chamber") wall 122 and the actuation chamber (also referred to as the "pneumatic chamber") wall 120 meet. The membrane 112 effectively divides that interior cavity into a variable-volume pumping chamber (defined by the rigid interior surface of the pumping chamber wall 122 and a surface of the membrane 112) and a complementary variable-volume actuation chamber (defined by the rigid interior surface of the actuation chamber wall 120 and a surface of the membrane 112). The top portion 106 includes a fluid inlet 102 and a fluid outlet 104, both of which are in fluid communication with the pumping/liquid chamber. The bottom portion 110 includes an actuation or pneumatic interface 114 in fluid communication with the actuation chamber. As discussed in greater detail below, the membrane 112 can be urged to move back and forth within the cavity by alternately applying negative or vent to atmosphere and positive pneumatic pressure at the pneumatic interface 114. As the membrane 112 reciprocates back and forth, the sum of the volumes of the pumping and actuation chambers remains constant.

During typical fluid pumping operations, the application of negative or vent to atmosphere pneumatic pressure to the actuation or pneumatic interface 114 tends to withdraw the membrane 112 toward the actuation chamber wall 120 so as to expand the pumping/liquid chamber and draw fluid into the pumping chamber through the inlet 102, while the application of positive pneumatic pressure tends to push the membrane 112 toward the pumping chamber wall 122 so as to collapse the pumping chamber and expel fluid in the pumping chamber through the outlet 104. During such pumping operations, the interior surfaces of the pumping chamber wall 122 and the actuation chamber wall 120 limit movement of the membrane 112 as it reciprocates back and forth. In the embodiment shown in FIG. 1A, the interior surfaces of the pumping chamber wall 122 and the actuation chamber wall 120 are rigid, smooth, and hemispherical. In lieu of a rigid actuation chamber wall 120, an alternative rigid limit structure—for example, a portion of a bezel used for providing pneumatic pressure and/or a set of ribs—may be used to limit the movement of the membrane as the pumping chamber approaches maximum value. Bezels and rib structures are described generally in U.S. patent application Ser. No. 10/697,450 entitled BEZEL ASSEMBLY FOR PNEUMATIC CONTROL filed on Oct. 30, 2003 and published as Publication No. US 2005/0095154 and related PCT Application No. PCT/US2004/035952 entitled BEZEL ASSEMBLY FOR PNEUMATIC CONTROL filed on Oct. 29, 2004 and published as Publication No. WO 2005/044435, both of which are hereby incorporated herein by reference in their entireties. Thus, the rigid limit structure—such as the rigid actuation chamber wall 120, a bezel, or a set of ribs—defines the shape of the membrane 112 when the pumping chamber is at its maximum value. In a preferred embodiment, the membrane 112 (when urged against the rigid limit structure) and the rigid interior surface of the pumping chamber wall 122 define a spherical pumping chamber volume when the pumping chamber volume is at a minimum.

Thus, in the embodiment shown in FIG. 1A, movement of the membrane 112 is limited by the pumping chamber wall 122 and the actuation chamber wall 120. As long as the positive and vent to atmosphere or negative pressurizations provided through the pneumatic port 114 are strong enough, the membrane 112 will move from a position limited by the actuation chamber wall 120 to a position limited by the pumping chamber wall 122. When the membrane 112 is forced against the actuation chamber wall 120, the membrane and the pumping chamber wall 122 define the maximum volume of the pumping chamber. When the membrane is forced against the pumping chamber wall 122, the pumping chamber is at its minimum volume.

In an exemplary embodiment, the pumping chamber wall 122 and the actuation chamber wall 120 both have a hemispheroid shape so that the pumping chamber will have a spheroid shape when it is at its maximum volume. By using a pumping chamber that attains a spheroid shape—and particularly a spherical shape—at maximum volume, circulating flow may be attained throughout the pumping chamber. Such shapes accordingly tend to avoid stagnant pockets of fluid in the pumping chamber. As discussed further below, the orientations of the inlet 102 and outlet 104 also tend to have an impact on the flow of fluid through the pumping chamber and in some embodiments, reduce the likelihood of stagnant pockets of fluid forming. Additionally, compared to other volumetric shapes, the spherical shape (and spheroid shapes in general) tends to create less shear and turbulence as the fluid circulates into, through, and out of the pumping chamber.

Figure 3:
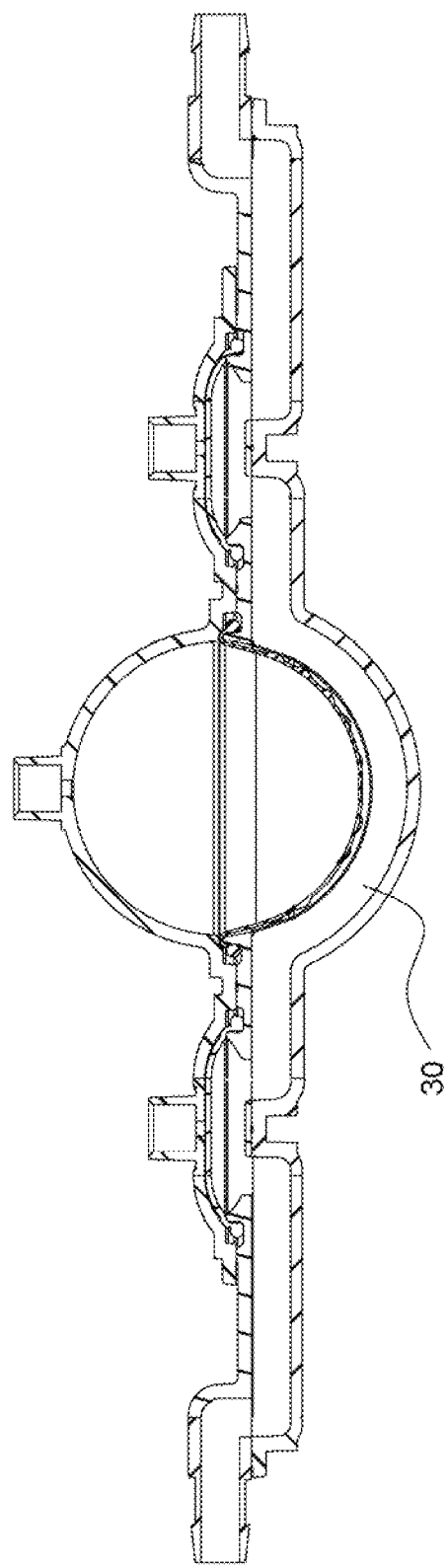
FIG. 3 is a section view of a pod pump within a cassette.
Figure 4:
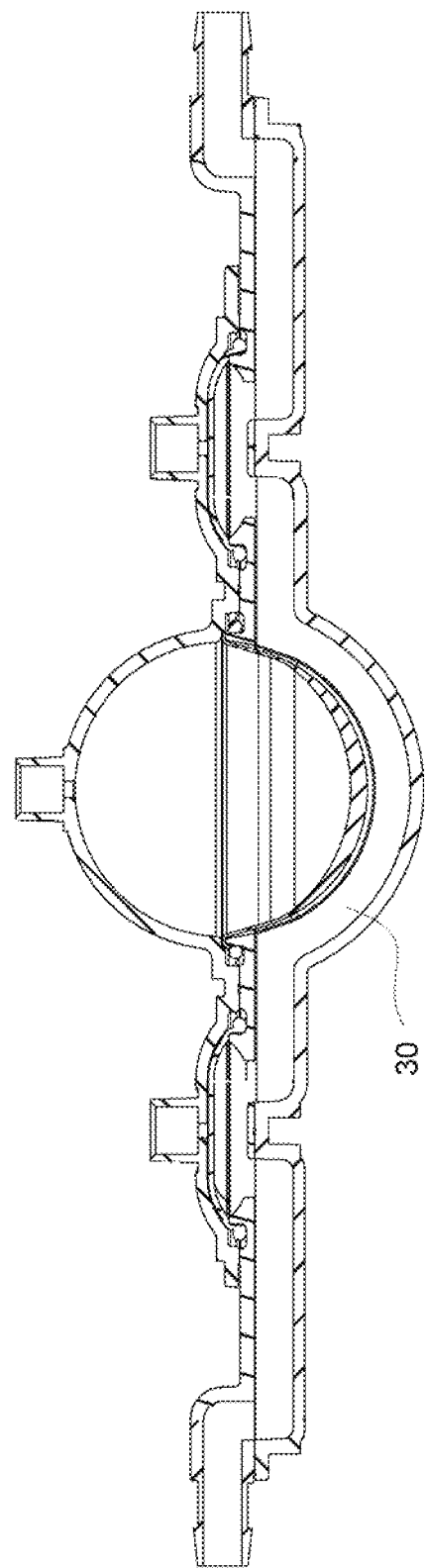
FIG. 4 is a section view of a pod pump within a cassette having a variable membrane.

Referring now to FIGS. 3-4, a raised flow path 30 is shown in the pumping chamber. This raised flow path 30 allows for the fluid to continue flowing through the pod pumps after the membrane reaches the end of stroke. Thus, the raised flow path 30 minimizes the chances of the membrane causing air or fluid to be trapped in the pod pump or the membrane blocking the inlet or outlet of the pod pump which would inhibit continuous flow. The raised flow path 30 is shown in the exemplary embodiment having particular dimensions. However, in alternate embodiments, as seen in FIGS. 18A-18E, the raised flow path 30 is narrower, or in still other embodiments, the raised flow path 30 can be any dimensions as the purpose is to control fluid flow so as to achieve a desired flow rate or behavior of the fluid. Thus, the dimensions shown and described here with respect to the raised flow path, the pod pumps, the valves, or any other aspect are mere exemplary and alternate embodiments. Other embodiments are readily apparent.

1.3 Exemplary Balancing Pods Embodiment

Referring now to FIGS. 1B, an exemplary embodiment of a balancing pod is shown. The balancing pod is constructed similar to the pod pump described above with respect to FIG. 1A. However, a balancing pod includes two fluid balancing chambers, rather than an actuation chamber and a pumping chamber, and does not include an actuation port. Additionally, each balancing chamber includes an inlet 102 and an outlet 104. In the exemplary embodiment, a groove 126 is included on each of the balancing chamber walls 120, 122. The groove 126 is described in further detail below.

The membrane 112 provides a seal between the two chambers. The balancing chambers work to balance the flow of fluid into and out of the chambers such that both chambers maintain an equal volume rate flow. Although the inlets 102 and outlets 104 for each chamber are shown to be on the same side, in other embodiments, the inlets 102 and outlets 104 for each chamber are on different sides. Also, the inlets 102 and outlets 104 can be on either side, depending on the flow path in which the balancing chamber is integrated.

In one embodiment of the balancing chambers the membrane 112 includes an embodiment similar to the one described below with respect to FIG. 6A-6G. However, in alternate embodiments, the membrane 112 can be over molded or otherwise constructed such that a double-ring seal is not applicable.

1.4 Metering Pumps and Fluid Management System

The metering pump can be any pump that is capable of adding any fluid or removing any fluid. The fluids include but are not limited to pharmaceuticals, inorganic compounds or elements, organic compounds or elements, nutraceuticals, nutritional elements or compounds or solutions, or any other fluid capable of being pumped. In one embodiment, the metering pump is a membrane pump. In the exemplary embodiment, the metering pump is a smaller volume pod pump. In the exemplary embodiment, the metering pump includes an inlet and an outlet, similar to a larger pod pump (as shown in FIG. 1A for example). However, the inlet and outlet are generally much smaller than a pod pump and, in one exemplary embodiment, includes a volcano valve-like raised ring around either the inlet or outlet. Metering pumps include a membrane, and various embodiments of a metering pump membrane are shown in FIGS. 5E-5H. The metering pump, in some embodiments, pumps a volume of fluid out of the fluid line. Once the fluid is in the pod pump, a reference chamber, located outside the cassette, using the FMS, determines the volume that has been removed.

Thus, depending on the embodiment, this volume of fluid that has been removed will not then flow to the fluid outlet, the balance chambers or to a pod pump. Thus, in some embodiments, the metering pump is used to remove a volume of fluid from a fluid line. In other embodiments, the metering pump is used to remove a volume of fluid to produce other results.

FMS may be used to perform certain fluid management system measurements, such as, for example, measuring the volume of subject fluid pumped through the pump chamber during a stroke of the membrane or detecting air in the pumping chamber, e.g., using techniques described in U.S. Pat. Nos. 4,808,161; 4,826,482; 4,976,162; 5,088,515; and 5,350,357, which are hereby incorporated herein by reference in their entireties.

Metering pumps are also used in various embodiments to pump a second fluid into the fluid line. In some embodiments, the metering pump is used to pump a therapeutic or a compound into a fluid line. One embodiment uses the metering pump to pump a volume of compound into a mixing chamber in order to constitute a solution. In some of these embodiments, the metering pumps are configured for FMS volume measurement. In other embodiments, the metering pumps are not.

For FMS measurement, a small fixed reference air chamber is located outside of the cassette, for example, in the pneumatic manifold (not shown). A valve isolates the reference chamber and a second pressure sensor. The stroke volume of the metering pump may be precisely computed by charging the reference chamber with air, measuring the pressure, and then opening the valve to the pumping chamber. The volume of air on the chamber side may be computed based on the fixed volume of the reference chamber and the change in pressure when the reference chamber was connected to the pump chamber.

1.5 Valves

Figure 2A:
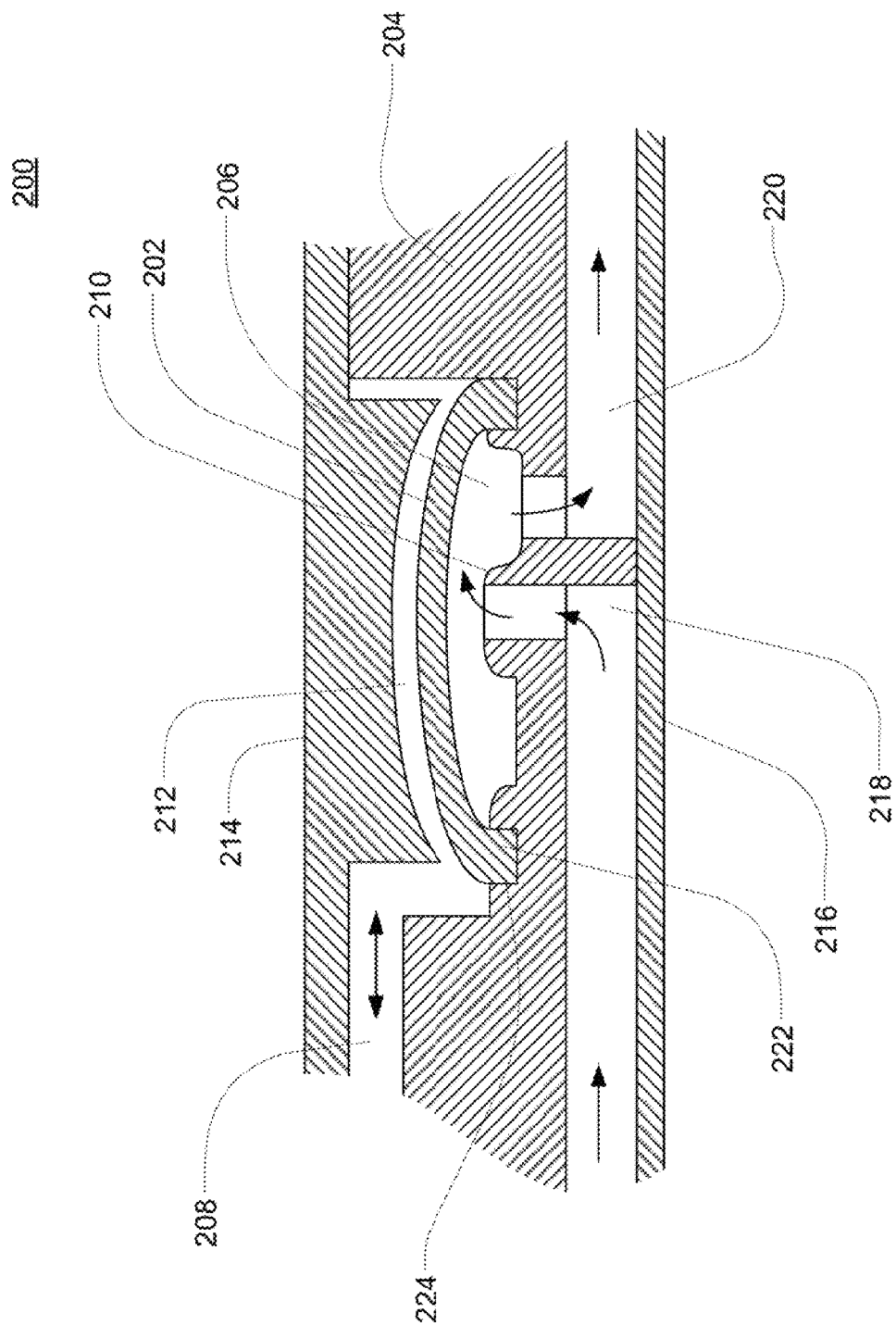
FIG. 2A is an illustrative sectional view of one embodiment of one type of pneumatically controlled valve that is incorporated into some embodiments of the cassette.
Figure 2B:
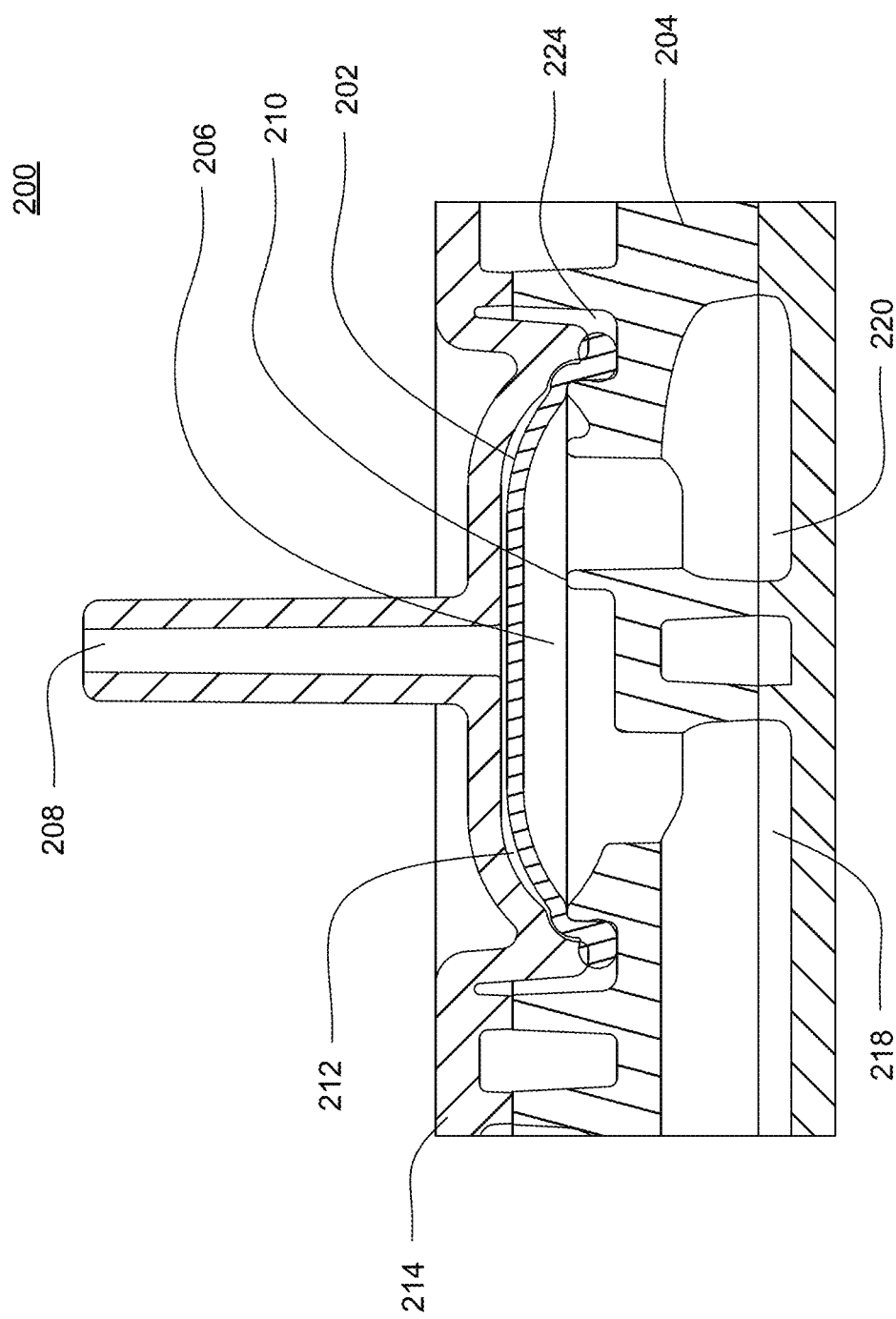
FIG. 2B is a sectional view of another embodiment of one type of pneumatically controlled valve that is incorporated into some embodiments of the cassette.
Figure 2C:
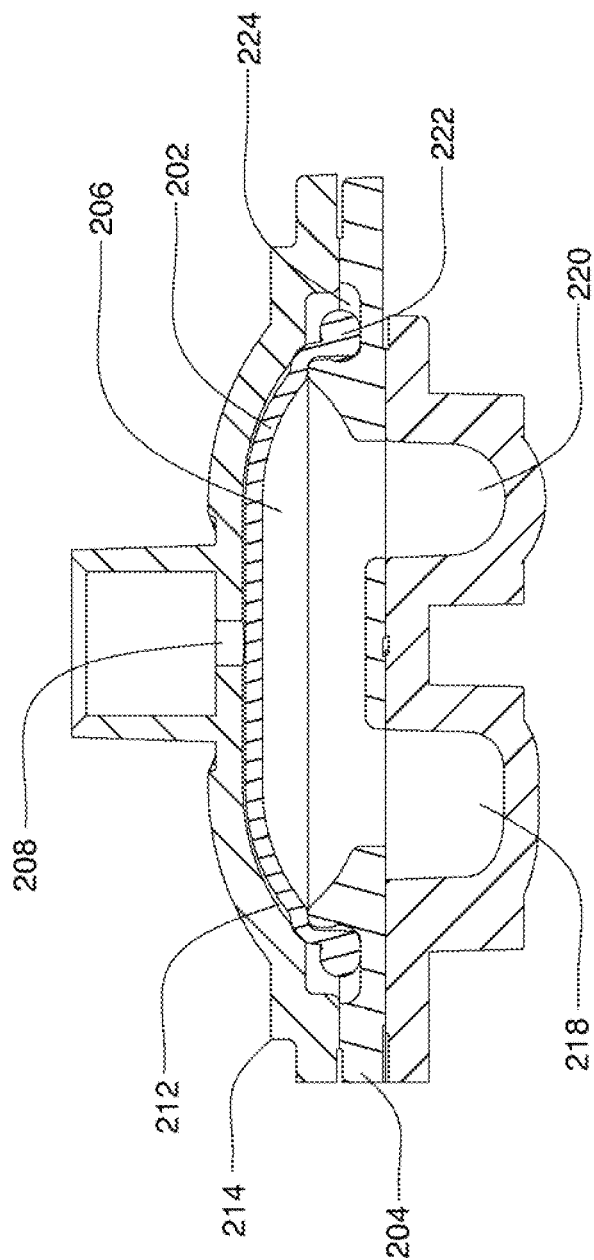
FIG. 2C is a sectional view of another embodiment of one type of pneumatically controlled valve that is incorporated into some embodiments of the cassette.

The exemplary embodiment of the cassette includes one or more valves. Valves are used to regulate flow by opening and closing fluid lines. The valves included in the various embodiments of the cassette include one or more of the following: volcano valves or smooth valves. In some embodiments of the cassette, check valves may be included. Embodiments of the volcano valve are shown in FIGS. 2A and 2B, while an embodiment of the smooth valve is shown in FIG. 2C. Additionally, FIGS. 3 and 4 show cross sections of one embodiment of a pod pump in a cassette with an inlet and an outlet valve.

Generally speaking, reciprocating positive-displacement pumps of the types just described may include, or may be used in conjunction with, various valves to control fluid flow through the pump. Thus, for example, the reciprocating positive-displacement pump or the balancing pods may include, or be used in conjunction with, an inlet valve and/or an outlet valve. The valves may be passive or active. In the exemplary embodiment of the reciprocating positive-displacement pump the membrane is urged back and forth by positive and negative pressurizations, or by positive and vent to atmosphere pressurizations, of a gas provided through the pneumatic port, which connects the actuation chamber to a pressure actuation system. The resulting reciprocating action of the membrane pulls fluid into the pumping chamber from the inlet (the outlet valve prevents liquid from being sucked back into the pumping chamber from the outlet) and then pushes the fluid out of the pumping chamber through the outlet (the inlet valve prevents fluid from being forced back from the inlet).

In the exemplary embodiments, active valves control the fluid flow through the pump(s) and the cassette. The active valves may be actuated by a controller in such a manner as to direct flow in a desired direction. Such an arrangement would generally permit the controller to cause flow in either direction through the pod pump. In a typical system, the flow would normally be in a first direction, e.g., from the inlet to the outlet. At certain other times, the flow may be directed in the opposite direction, e.g., from the outlet to the inlet. Such reversal of flow may be employed, for example, during priming of the pump, to check for an aberrant line condition (e.g., a line occlusion, blockage, disconnect, or leak), or to clear an aberrant line condition (e.g., to try to dislodge a blockage).

Pneumatic actuation of valves provides pressure control and a natural limit to the maximum pressure that may be developed in a system. In the context of a system, pneumatic actuation has the added benefit of providing the opportunity to locate all the solenoid control valves on one side of the system away from the fluid paths.

Referring now to FIGS. 2A and 2B, sectional views of two embodiments of a volcano valve are shown. The volcano valves are pneumatically controlled valves that may be used in embodiments of the cassette. A membrane 202, along with the midplate 204, defines a valving chamber 206. Pneumatic pressure is provided through a pneumatic port 208 to either force, with positive gas pressure, the membrane 202 against a valve seat 210 to close the valve, or to draw, with negative gas pressure, or in some embodiments, with vent to atmospheric pressure, the membrane away from the valve seat 210 to open the valve. A control gas chamber 212 is defined by the membrane 202, the top plate 214, and the midplate 204. The midplate 204 has an indentation formed on it, into which the membrane 202 is placed so as to form the control gas chamber 212 on one side of the membrane 202 and the valving chamber 206 on the other side.

The pneumatic port 208 is defined by a channel formed in the top plate 214. By providing pneumatic control of several valves in a cassette, valves can be ganged together so that all the valves ganged together can be opened or closed at the same time by a single source of pneumatic pressure. Channels formed on the midplate 204, corresponding with fluid paths along with the bottom plate 216, define the valve inlet 218 and the valve outlet 220. Holes formed through the midplate 204 provide communication between the inlet 218 and the valving chamber 206 and between the valving chamber 206 and the outlet 220.

The membrane 202 is provided with a thickened rim 222, which fits tightly in a groove 224 in the midplate 204. Thus, the membrane 202 can be placed in and held by the groove 224 before the top plate 214 is connected to the midplate 204. Thus, this valve design may impart benefits in manufacture. As shown in FIGS. 2B and 2C, the top plate 214 may include additional material extending into control gas chamber 212 so as to prevent the membrane 202 from being urged too much in a direction away from the groove 224, so as to prevent the membrane's thickened rim 222 from popping out of the groove 224. The location of the pneumatic port 208 with respect to the control gas chamber 212 varies in the two embodiments shown in FIGS. 2A and 2B.

Figure 2D:
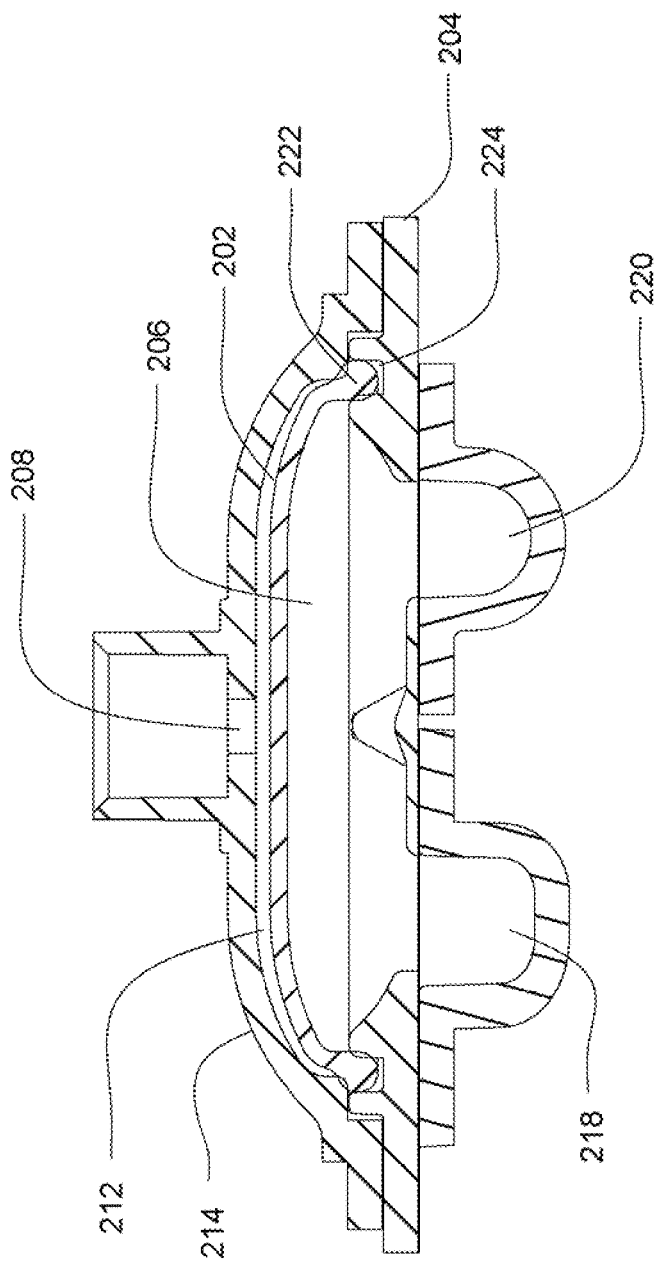
FIG. 2D is a sectional view of another embodiment of one type of pneumatically controlled valve that is incorporated into some embodiments of the cassette.
Figure 2E:
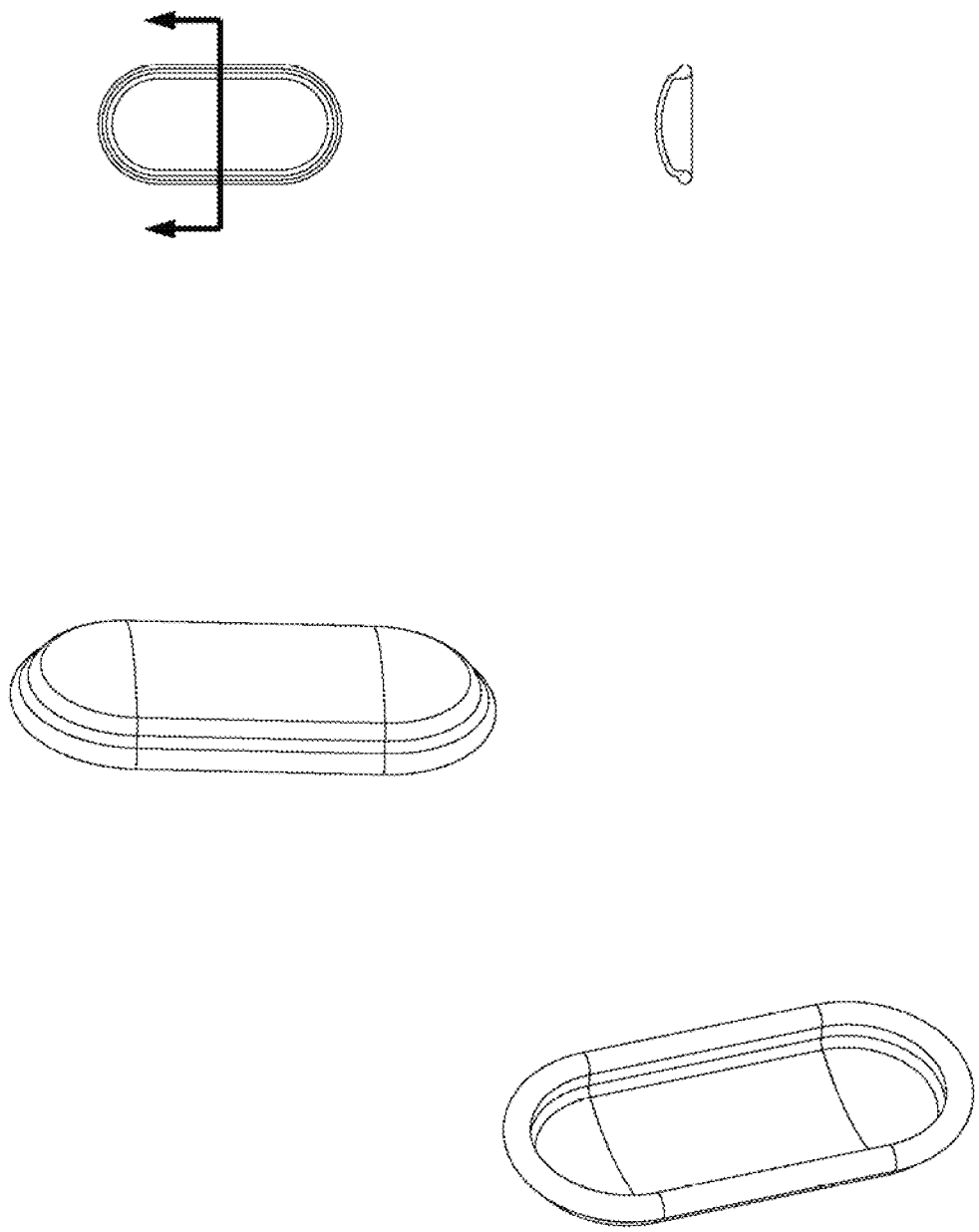
FIGS. 2E-2F are top and bottom views of embodiments of the valving membrane.
Figure 2F:
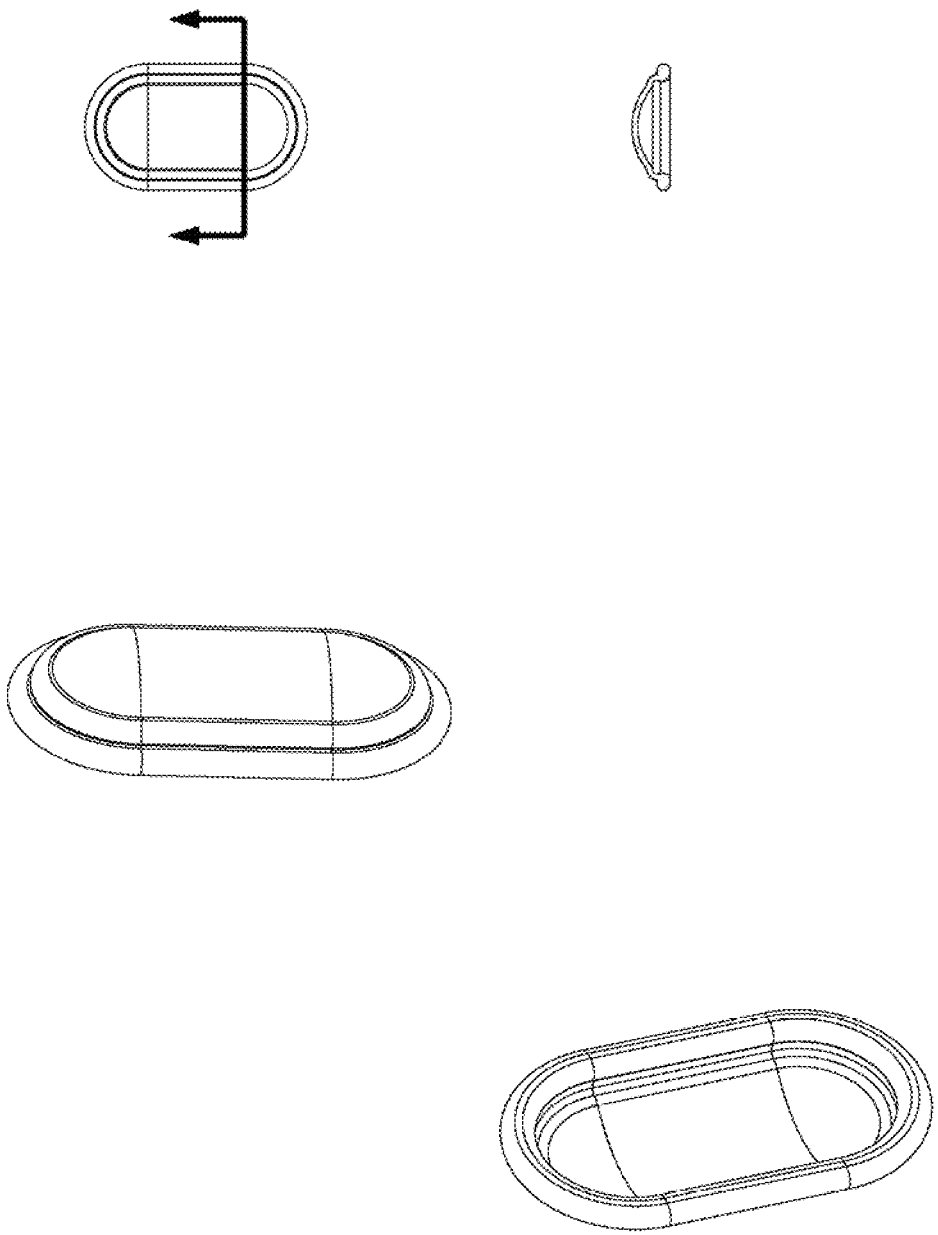
Figure 2G:
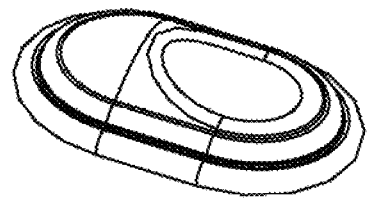
FIG. 2G shows pictorial, top and cross sectional views of one embodiment of the valving membrane.
Figure 2G:
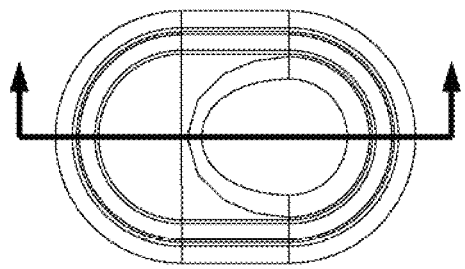
Figure 2G:

FIG. 2C shows an embodiment in which the valving chamber lacks a valve seat feature. Rather, in FIG. 2C, the valve in this embodiment does not include any volcano features and thus, the valving chamber 206, i.e., the fluid side, does not include any raised features and thus is smooth. This embodiment is used in cassettes used to pump fluid sensitive to shearing. FIG. 2D shows an embodiment in which the valving chamber has a raised area to aid in the sealing of the valving membrane. Referring now to FIGS. 2E-2G, various embodiments of the valve membrane are shown. Although some exemplary embodiments have been shown and described, in other embodiments, variations of the valve and valving membrane may be used.

1.6 Exemplary Embodiments of the Pod Membrane

In some embodiments, the membrane has a variable cross-sectional thickness, as shown in FIG. 4. Thinner, thicker or variable thickness membranes may be used to accommodate the strength, flexural and other properties of the chosen membrane's materials. Thinner, thicker or variable membrane wall thickness may also be used to manage the membrane thereby encouraging it to flex more easily in some areas than in other areas, thereby aiding in the management of pumping action and flow of subject fluid in the pump chamber. In this embodiment, the membrane is shown having its thickest cross-sectional area closest to its center. However, in other embodiments having a membrane with a varying cross section, the thickest and thinnest areas may be in any location on the membrane. Thus, for example, the thinner cross section may be located near the center and the thicker cross sections located closer to the perimeter of the membrane. Still other configurations are possible. Referring to FIGS. 5A-5D, one embodiment of a membrane is shown having various surface embodiments, these include smooth (FIG. 5A), rings (FIG. 5D), ribs (FIG. 5C), dimples or dots (FIG. 5B) of variable thickness and or geometry located at various locations on the actuation and or pumping side of the membrane. In one embodiment of the membrane, the membrane has a tangential slope in at least one section, but in other embodiments, the membrane is completely smooth or substantially smooth.

Figure 4A:
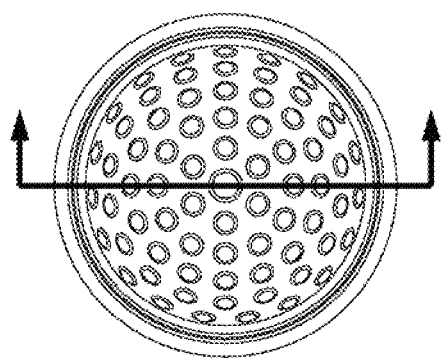
FIGS. 4A and 4B are top and section views respectively of a dimpled/variable membrane.
Figure 4B:
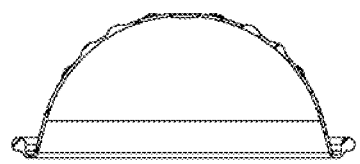
Figure 4C:
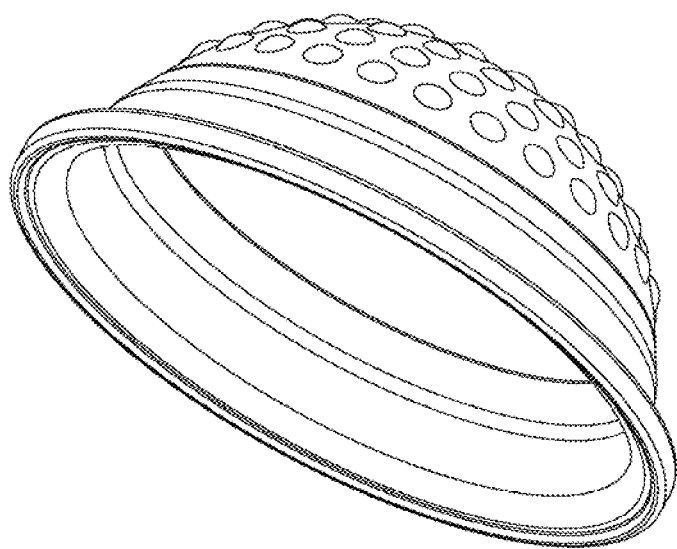
FIGS. 4C and 4D are pictorial views of a single ring membrane with a variable surface.
Figure 4D:
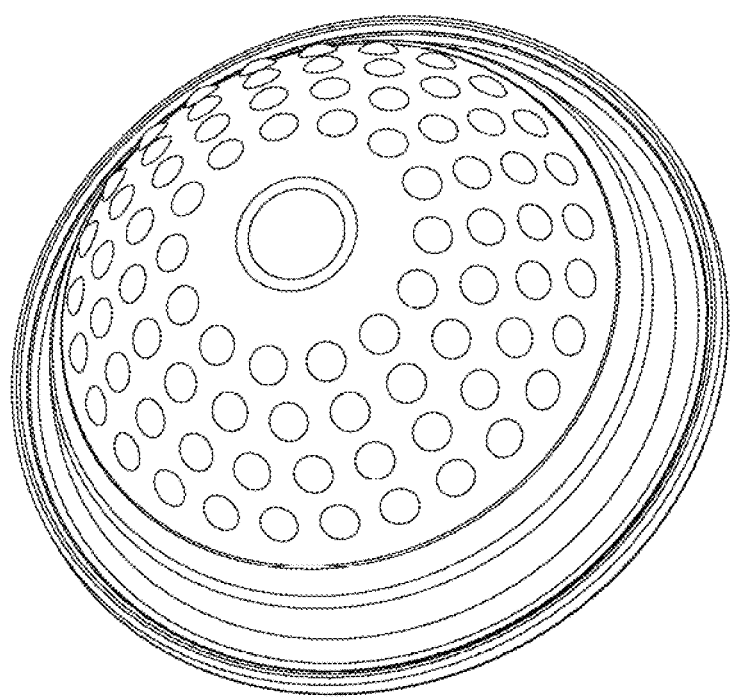

Referring now to FIGS. 4A, 4C and 4D, an alternate embodiment of the membrane is shown. In this embodiment, the membrane has a dimpled or dotted surface.

The membrane may be made of any flexible material having a desired durability and compatibility with the subject fluid. The membrane can be made from any material that may flex in response to fluid, liquid or gas pressure or vacuum applied to the actuation chamber. The membrane material may also be chosen for particular bio-compatibility, temperature compatibility or compatibility with various subject fluids that may be pumped by the membrane or introduced to the chambers to facilitate movement of the membrane. In the exemplary embodiment, the membrane is made from high elongation silicone. However, in other embodiments, the membrane is made from any elastomer or rubber, including, but not limited to, silicone, urethane, nitrile, EPDM or any other rubber, elastomer or flexible material.

The shape of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. The size of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. Thus, depending on these or other variables, the shape and size of the membrane may vary in various embodiments.

The membrane can have any thickness. However, in some embodiments, the range of thickness is between 0.002 inches to 0.125 inches. Depending on the material used for the membrane, the desired thickness may vary. In one embodiment, high elongation silicone is used in a thickness ranging from 0.015 inches to 0.050 inches. However, in other embodiments, the thickness may vary.

In the exemplary embodiment, the membrane is preformed to include a substantially dome shape in at least part of the area of the membrane. One embodiment of the dome-shaped membrane is shown in FIGS. 4C and 4D. Again, the dimensions of the dome may vary based on some or more of the variables described above. However, in other embodiments, the membrane may not include a preformed dome shape.

In the exemplary embodiment, the membrane dome is formed using liquid injection molding. However, in other embodiments, the dome may be formed by using compression molding. In alternate embodiments, the membrane is substantially flat. In other embodiments, the dome size, width, or height may vary.

In various embodiments, the membrane may be held in place by various means and methods. In one embodiment, the membrane is clamped between the portions of the cassette, and in some of these embodiments, the rim of the cassette may include features to grab the membrane. In others of this embodiment, the membrane is clamped to the cassette using at least one bolt or another device. In another embodiment, the membrane is over-molded with a piece of plastic and then the plastic is welded or otherwise attached to the cassette. In another embodiment, the membrane is pinched between the mid plate described with respect to FIGS. 1A and 1B and the bottom plate. Although some embodiments for attachment of the membrane to the cassette are described, any method or means for attaching the membrane to the cassette can be used. The membrane, in one alternate embodiment, is attached directly to one portion of the cassette. In some embodiments, the membrane is thicker at the edge, where the membrane is pinched by the plates, than in other areas of the membrane. In some embodiments, this thicker area is a gasket, and in some embodiments an O-ring, ring, or any other shaped gasket. Referring again to FIGS. 6A-6D, one embodiment of the membrane is shown with two gaskets 62, 64. In some of these embodiments, the gaskets 62, 64 provide the attachment point of the membrane to the cassette. In other embodiments, the membrane includes more than two gaskets. Membranes with one gasket are also included in some embodiments (see FIGS. 4A-4D).

In some embodiments of the gasket, the gasket is contiguous with the membrane. However, in other embodiments, the gasket is a separate part of the membrane. In some embodiments, the gasket is made from the same material as the membrane. However, in other embodiments, the gasket is made of a material different from the membrane. In some embodiments, the gasket is formed by over-molding a ring around the membrane. The gasket can be any shape ring or seal desired so as to complement the pod pump housing embodiment. In some embodiments, the gasket is a compression type gasket.

1.7 Mixing Pods

Some embodiments of the cassette include a mixing pod. A mixing pod includes a chamber for mixing. In some embodiments, the mixing pod is a flexible structure, and in some embodiments, at least a section of the mixing pod is a flexible structure. The mixing pod can include a seal, such as an o-ring, or a membrane. The mixing pod can be any shape desired. In the exemplary embodiment, the mixing pod is similar to a pod pump except it does not include a membrane and does not include an actuation port. Some embodiments of this embodiment of the mixing pod include an o-ring seal to seal the mixing pod chamber. Thus, in the exemplary embodiment, the mixing pod is a spherical hollow pod with a fluid inlet and a fluid outlet. As with the pod pumps, the chamber size can be any size desired.

2. Pressure Pump Actuation System

Figure 7:
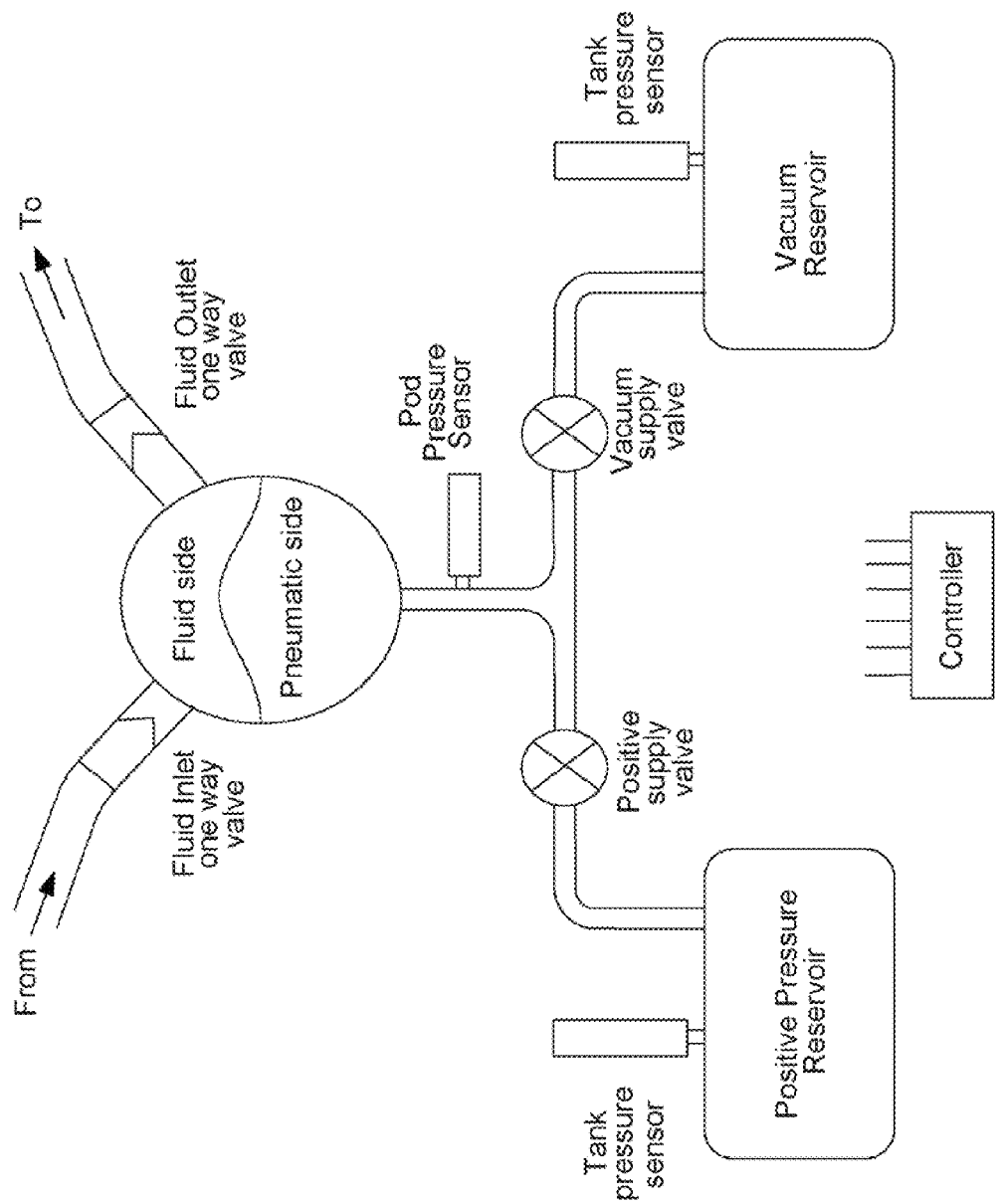
FIG. 7 is a schematic showing a pressure actuation system that may be used to actuate a pod pump.

FIG. 7 is a schematic showing an embodiment of a pressure actuation system that may be used to actuate a pod pump with both positive and negative pressure, such as the pod pump shown in FIG. 1A. The pressure actuation system is capable of intermittently or alternately providing positive and negative pressurizations to the gas in the actuation chamber of the pod pump. However, in some embodiments, FIG. 7 does not apply, in these embodiments, actuation of the pod pump is accomplished by applying positive pressure and vent to atmosphere (again, not shown in FIG. 7). The pod pump—including the flexible membrane, the inlet, the outlet, the pneumatic port, the pumping chamber, the actuation chamber, and possibly including an inlet check valve and an outlet check valve or other valves—is part of a larger disposable system. The pneumatic actuation system—including an actuation-chamber pressure transducer, a positive-supply valve, a negative-supply valve, a positive-pressure gas reservoir, a negative-pressure gas reservoir, a positive-pressure-reservoir pressure transducer, a negative-pressure-reservoir pressure transducer, as well as an electronic controller including, in some embodiments, a user interface console (such as a touch-panel screen)—may be part of a base unit.

The positive-pressure reservoir provides to the actuation chamber the positive pressurization of a control gas to urge the membrane towards a position where the pumping chamber is at its minimum volume (i.e., the position where the membrane is against the rigid pumping-chamber wall). The negative-pressure reservoir provides to the actuation chamber the negative pressurization of the control gas to urge the membrane in the opposite direction, towards a position where the pumping chamber is at its maximum volume (i.e., the position where the membrane is against the rigid actuation-chamber wall).

A valving mechanism is used to control fluid communication between each of these reservoirs and the actuation chamber. As shown in FIG. 7, a separate valve is used for each of the reservoirs; a positive-supply valve controls fluid communication between the positive-pressure reservoir and the actuation chamber, and a negative-supply valve controls fluid communication between the negative-pressure reservoir and the actuation chamber. These two valves are controlled by the controller. Alternatively, a single three-way valve may be used in lieu of the two separate valves. The valves may be binary on-off valves or variable-restriction valves.

The controller also receives pressure information from the three pressure transducers: an actuation-chamber pressure transducer, a positive-pressure-reservoir pressure transducer, and a negative-pressure-reservoir pressure transducer. As their names suggest, these transducers respectively measure the pressure in the actuation chamber, the positive-pressure reservoir, and the negative-pressure reservoir. The actuation-chamber-pressure transducer is located in a base unit but is in fluid communication with the actuation chamber through the pod pump pneumatic port. The controller monitors the pressure in the two reservoirs to ensure they are properly pressurized (either positively or negatively). In one exemplary embodiment, the positive-pressure reservoir may be maintained at around 750 mmHg, while the negative-pressure reservoir may be maintained at around −450 mmHg.

Still referring to FIG. 7, a compressor-type pump or pumps (not shown) may be used to maintain the desired pressures in these reservoirs. For example, two independent compressors may be used to respectively service the reservoirs. Pressure in the reservoirs may be managed using a simple bang-bang control technique in which the compressor servicing the positive-pressure reservoir is turned on if the pressure in the reservoir falls below a predetermined threshold and the compressor servicing the negative-pressure reservoir is turned on if the pressure in the reservoir is above a predetermined threshold. The amount of hysteresis may be the same for both reservoirs or may be different. Tighter control of the pressure in the reservoirs can be achieved by reducing the size of the hysteresis band, although this will generally result in higher cycling frequencies of the compressors. If very tight control of the reservoir pressures is required or otherwise desirable for a particular application, the bang-bang control technique could be replaced with a PID control technique and could use PWM signals on the compressors.

The pressure provided by the positive-pressure reservoir is preferably strong enough—under normal conditions—to urge the membrane all the way against the rigid pumping-chamber wall. Similarly, the negative pressure (i.e., the vacuum) provided by the negative-pressure reservoir is preferably strong enough—under normal conditions—to urge the membrane all the way against the actuation-chamber wall. In a further preferred embodiment, however, these positive and negative pressures provided by the reservoirs are within safe enough limits that even with either the positive-supply valve or the negative-supply valve open all the way, the positive or negative pressure applied against the membrane is not so strong as to damage the pod pump or create unsafe fluid pressures (e.g., that may harm a patient receiving pumped blood or other fluid).

It will be appreciated that other types of actuation systems may be used to move the membrane back and forth instead of the two-reservoir pneumatic actuation system shown in FIG. 7, although a two-reservoir pneumatic actuation system is generally preferred. For example, alternative pneumatic actuation systems may include either a single positive-pressure reservoir or a single negative-pressure reservoir along with a single supply valve and a single tank pressure sensor, particularly in combination with a resilient membrane. Such pneumatic actuation systems may intermittently provide either a positive gas pressure or a negative gas pressure to the actuation chamber of the pod pump. In embodiments having a single positive-pressure reservoir, the pump may be operated by intermittently providing positive gas pressure to the actuation chamber, causing the membrane to move toward the pumping chamber wall and expel the contents of the pumping chamber, and releasing the gas pressure, causing the membrane to return to its relaxed position and draw fluid into the pumping chamber. In embodiments having a single negative-pressure reservoir, the pump may be operated by intermittently providing negative gas pressure to the actuation chamber, causing the membrane to move toward the actuation chamber wall and draw fluid into the pumping chamber, and releasing the gas pressure, causing the membrane to return to its relaxed position and expel fluid from the pumping chamber.

3. Fluid Handling

As shown and described with respect to FIGS. 2A-2D, a fluid valve in the exemplary embodiment consists of a small chamber with a flexible membrane or membrane across the center dividing the chamber into a fluid half and a pneumatic half. The fluid valve, in the exemplary embodiment, has three entry/exit ports, two on the fluid half of the chamber and one the pneumatic half of the chamber. The port on the pneumatic half of the chamber can supply either positive pressure or vacuum (or rather than vacuum, in some embodiments, there is a vent to atmosphere) to the chamber. When a vacuum is applied to the pneumatic portion of the chamber, the membrane is pulled towards the pneumatic side of the chamber, clearing the fluid path and allowing fluid to flow into and out of the fluid side of the chamber. When positive pressure is applied to the pneumatic portion of the chamber, the membrane is pushed towards the fluid side of the chamber, blocking the fluid path and preventing fluid flow. In the volcano valve embodiment (as shown in FIGS. 2A-2B) on one of the fluid ports, that port seals off first when closing the valve and the remainder of any fluid in the valve is expelled through the port without the volcano feature. Additionally, in one embodiment of the valves, shown in FIG. 2D, the raised feature between the two ports allows for the membrane to seal the two ports from each other earlier in the actuation stroke (i.e., before the membrane seals the ports directly).

Referring again to FIG. 7, pressure valves are used to operate the pumps located at different points in the flow path. This architecture supports pressure control by using two variable-orifice valves and a pressure sensor at each pump chamber which requires pressure control. In one embodiment, one valve is connected to a high-pressure source and the other valve is connected to a low-pressure sink. A high-speed control loop monitors the pressure sensor and controls the valve positions to maintain the necessary pressure in the pump chamber.

Pressure sensors are used to monitor pressure in the pneumatic portion of the chambers themselves. By alternating between positive pressure and vacuum on the pneumatic side of the chamber, the membrane is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

In many embodiments, pressure pumps consist of a pair of chambers. When the two chambers are run 180 degrees out of phase from one another the flow is essentially continuous.

4. Volume Measurement

These flow rates in the cassette are controlled using pressure pod pumps which can detect end of stroke. An outer control loop determines the correct pressure values to deliver the required flow. Pressure pumps can run an end-of-stroke algorithm to detect when each stroke completes. While the membrane is moving, the measured pressure in the chamber tracks a desired sinusoidal pressure. When the membrane contacts a chamber wall, the pressure becomes constant, no longer tracking the sinusoid. This change in the pressure signal is used to detect when the stroke has ended, i.e., the end of stroke.

The pressure pumps have a known volume. Thus, an end of stroke indicates a known volume of fluid is in the chamber. Thus, using the end of stroke, fluid flow may be controlled using rate equating to volume.

As described above in more detail, FMS may be used to determine the volume of fluid pumped by the metering pumps. In some embodiments, the metering pump may pump fluid without using the FMS volume measurement system, however, in the exemplary embodiments, the FMS volume measurement system is used to calculate the exact volume of fluid pumped.

5. Exemplary Embodiment of the Pumping Cassette

Referring now to FIG. 8A, an exemplary embodiment of the fluid schematic of the balancing pumping and metering cassette 800 is shown. Other schematics are readily discernable. The cassette 800 includes at least one pod pump 828, 820 and at least one balancing pod 822, 812. The cassette 800 also includes a first fluid inlet 810, where a first fluid enters the cassette. The first fluid includes a flow rate provided outside the cassette 800. The cassette 800 also includes a first fluid outlet 824 where the first fluid exits the cassette 800 having a flow rate provided by one of the at least one pod pumps 828. The cassette 800 includes a second fluid inlet 826 where the second fluid enters the cassette 800, and a second fluid outlet 816 where the second fluid exits the cassette.

Balancing pods 822, 812 in the cassette 800 provide for a desired balance of volume of fluid pumped into and out of the cassette 800, i.e., between the first fluid and the second fluid. The balancing pods 822, 812, however, may be bypassed by way of the metering pump 830. The metering pump 830 pumps a volume of second fluid (or first fluid in other embodiments) out of the fluid line, bypassing the balancing pod 822, 812. Thus, a smaller or reduced volume (i.e., a "new" volume) of the fluid that has been removed by the metering pump 830 will actually enter the balancing pod 822, 812 and thus, the metering pump 830 functions to provide a "new" volume of second fluid by removing the desired volume from the fluid path before the second fluid reaches the balancing pod 822, 812 (or in other embodiments, removing first fluid the desired volume from the fluid path before the second fluid reaches the balancing pod 822, 812) resulting in less first fluid (or in other embodiments, second fluid) being pumped for that pump cycle.

The fluid schematic of the cassette 800 shown in FIG. 8A may be embodied into various cassette apparatus. Thus, the embodiments of the cassette 800 including the fluid schematic shown in FIG. 8A are not the only cassette embodiments that may incorporate this or an alternate embodiment of this fluid schematic. Additionally, the types of valves, the ganging of the valves, the number of pumps and chambers may vary in various cassette embodiments of this fluid schematic.

Figure 9A:
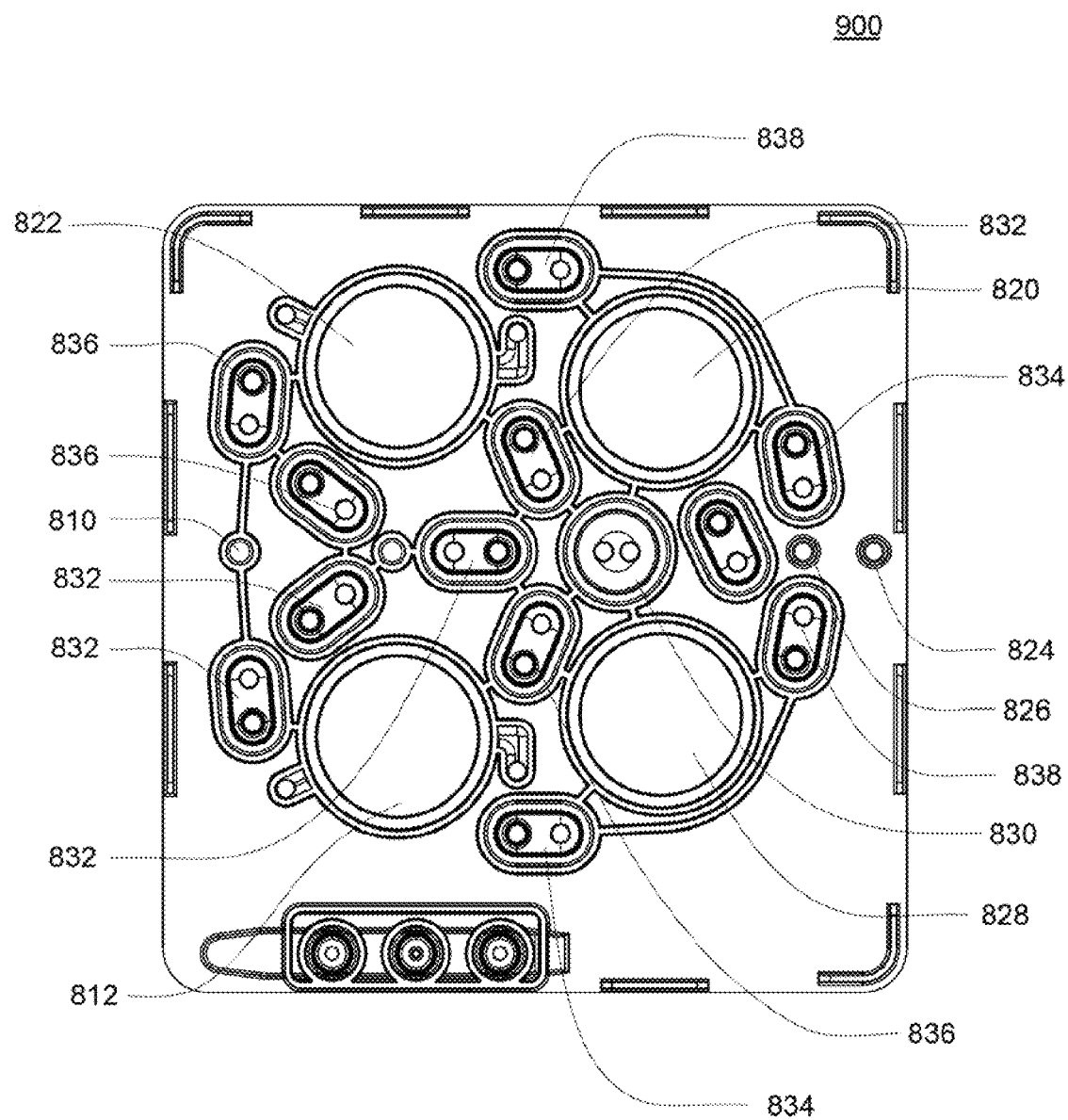
FIG. 9A is an isometric bottom view of the exemplary embodiment of the midplate of the exemplary embodiment of the cassette.
Figure 9B:
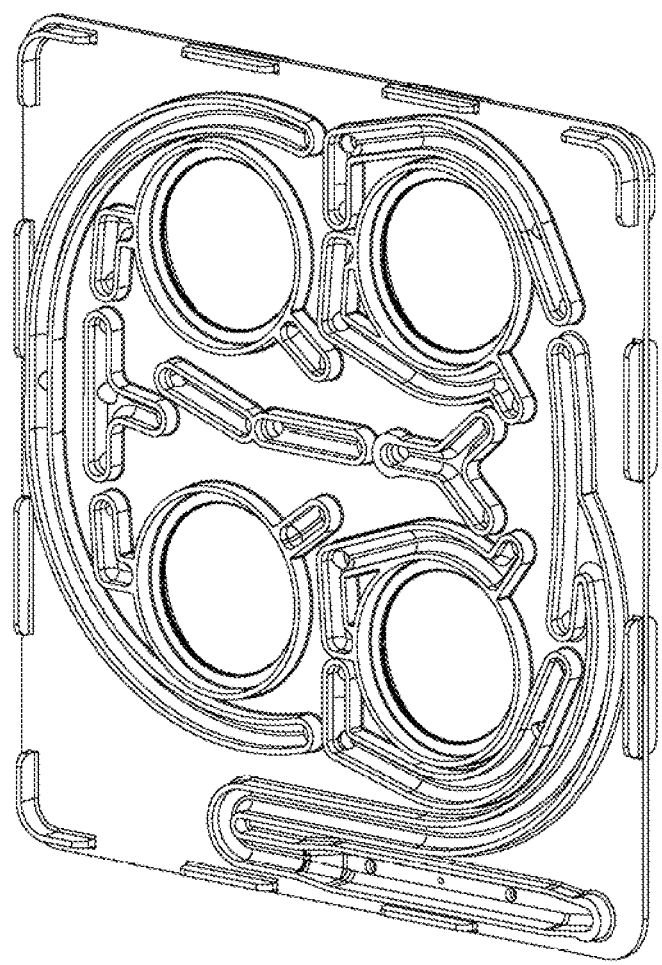
FIG. 9B is an isometric top view of the of the midplate of the exemplary embodiment of the cassette.
Figure 9C:
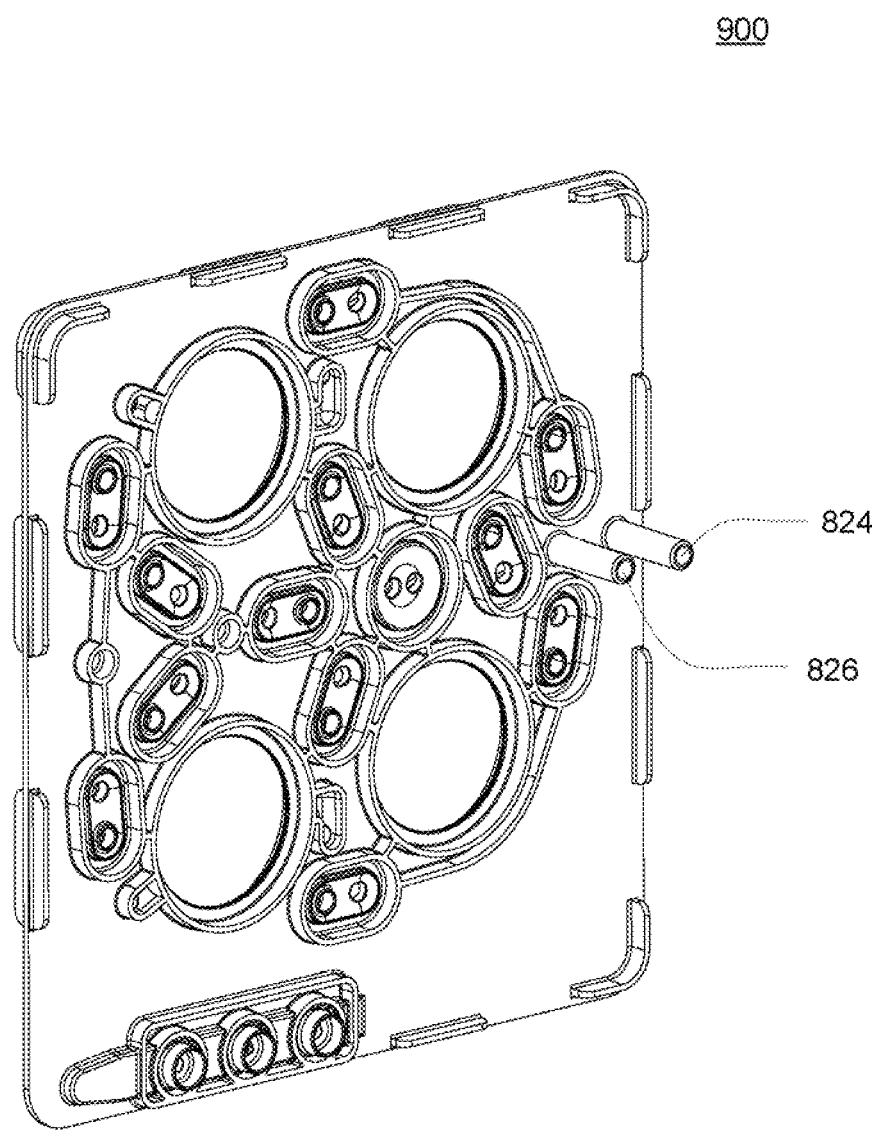
FIG. 9C is an isometric bottom view of the exemplary embodiment of the midplate of the cassette.
Figure 9D:
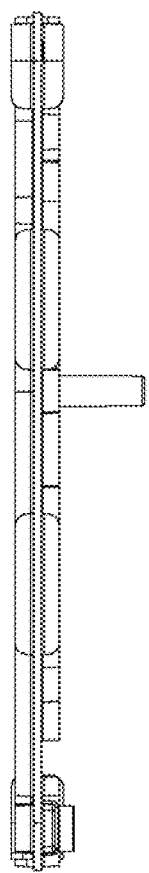
FIG. 9D is a side view of the exemplary embodiment of the midplate of the cassette.

Referring still to FIG. 8A, a fluid flow-path schematic 800 is shown. The fluid flow-path schematic 800 is described herein corresponding to the flow paths in one embodiment of the cassette. The exemplary embodiment of the midplate 900 of the cassette is shown in FIG. 9A with the valves corresponding to the fluid flow-path schematic in FIG. 8A indicated. The valving side of the midplate 900 shown in FIG. 9A corresponds to the fluid side shown in FIG. 9B.

Referring first to FIG. 8A with FIG. 9A, a first fluid enters the cassette at the first fluid inlet 810. The first fluid flows to balancing pod A 812. Balancing pod A 812 is a balancing pod as described above. Balancing pod A 812 initially contained a first volume of second fluid. When the first fluid flows into the balancing pod A 812, the membrane forces the second fluid out of balancing pod A 812. The second fluid flows through the drain path 814 and out the first fluid outlet 816.

At the same time, pod pump B 820 includes a volume of second fluid. The volume of second fluid is pumped to balancing pod B 822. Balancing pod B 822 contains a volume of first fluid, and this volume of first fluid is displaced by the volume of second fluid. The volume of first fluid from balancing pod B 822 flows to the second fluid outlet 824 and exits the cassette. A volume of a second fluid enters the cassette at fluid inlet two 826 and flows to pod pump A 828.

Referring still to FIG. 8A with FIG. 9A, the second fluid is pumped from pod pump A 828 to balancing pod A 812. The second fluid displaces the first fluid in balancing pod A 812. The first fluid from balancing pod A 812 flows to the second fluid outlet 824.

First fluid flows into the cassette through the first fluid inlet 810 and flows to balancing pod B 822. The first fluid displaces the second fluid in balancing pod B 822, forcing the second fluid to flow out of the cassette through the first fluid outlet 816. Second fluid flows into the cassette through the second fluid inlet 826 and to pod pump B 820.

The metering pump can be actuated at any time and its function is to remove fluid from the fluid path in order to bypass the balancing pod. Thus, any volume of fluid removed would act to decrease the volume of the other fluid flowing out of the second fluid outlet 824. The metering pump is independent of the balancing pods 812, 822 and the pod pumps 820, 828. The fluid enters through fluid inlet two 826 and is pulled by the metering pump 830. The metering pump then pumps the volume of fluid through the second fluid outlet 816.

Although in the embodiment of the fluid schematic shown in FIG. 8A, the metering pump is described only with respect to second fluid entering the cassette through fluid inlet two 826, the metering pump can easily bypass first fluid entering the cassette through fluid inlet one 810. Thus, depending on whether the desired end result is to have less of the first fluid or less of the second fluid, the metering pump and valves that control the fluid lines in the cassette can perform accordingly to accomplish the result.

In the exemplary fluid flow-path embodiment shown in FIG. 8A, and corresponding structure of the cassette shown in FIG. 9A, valves are ganged such that they are actuated at the same time. In the preferred embodiment, there are four gangs of valves 832, 834, 836, 838. In the preferred embodiment, the ganged valves are actuated by the same air line. However, in other embodiments, each valve has its own air line. Ganging the valves as shown in the exemplary embodiment creates the fluid-flow described above. In some embodiments, ganging the valves also ensures the appropriate valves are opened and closed to dictate the fluid pathways as desired.

In the exemplary embodiment, the fluid valves are volcano valves, as described in more detail in this specification. Although the fluid flow-path schematic has been described with respect to a particular flow path, in various embodiments, the flow paths can change based on the actuation of the valves and the pumps. Additionally, the terms inlet and outlet as well as first fluid and second fluid are used for description purposes only. In other embodiments, an inlet can be an outlet, as well as, a first and second fluid may be different fluids or the same fluid types or composition.

Figure 10A:
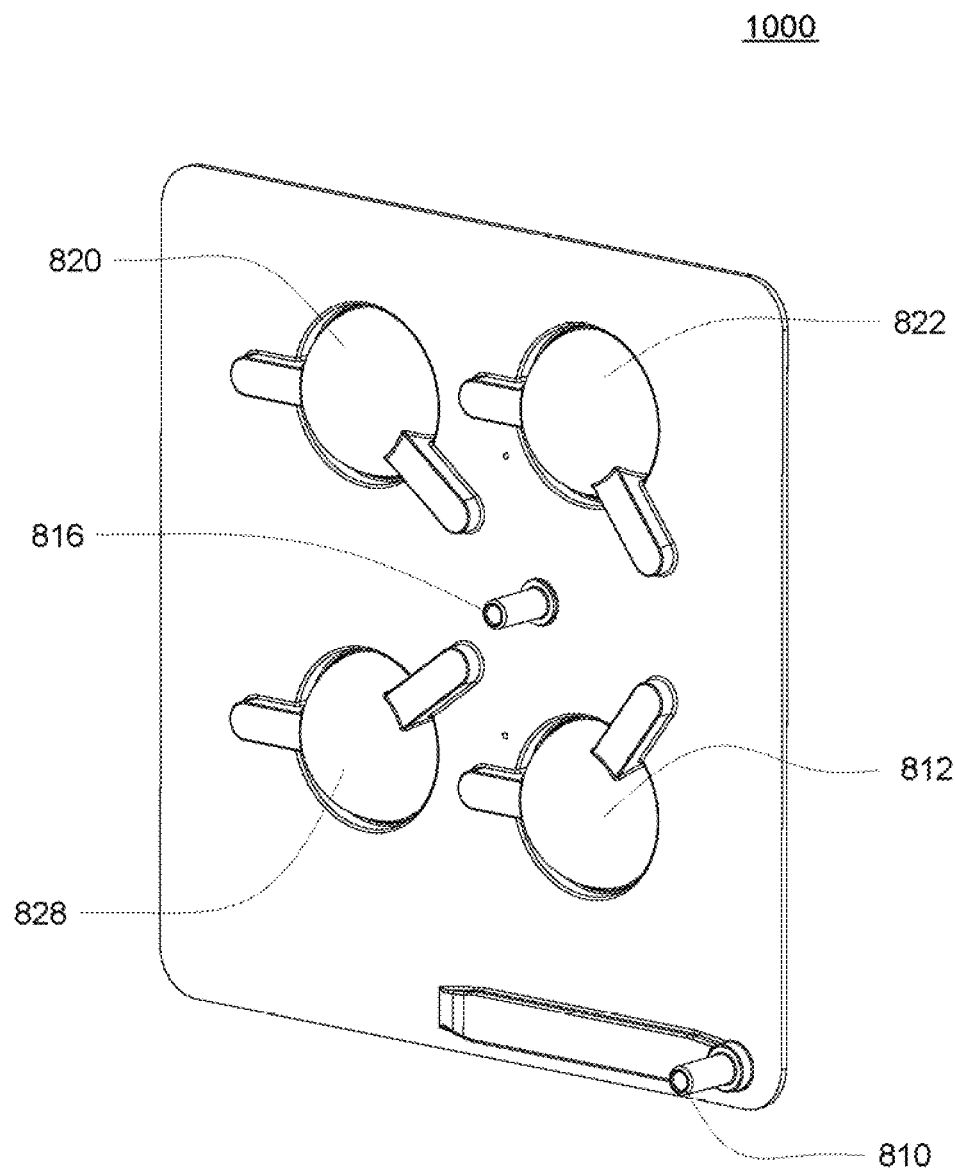
FIGS. 10A-10B are isometric and top views of the exemplary embodiment of the top plate of the exemplary embodiment of the cassette.
Figure 10B:
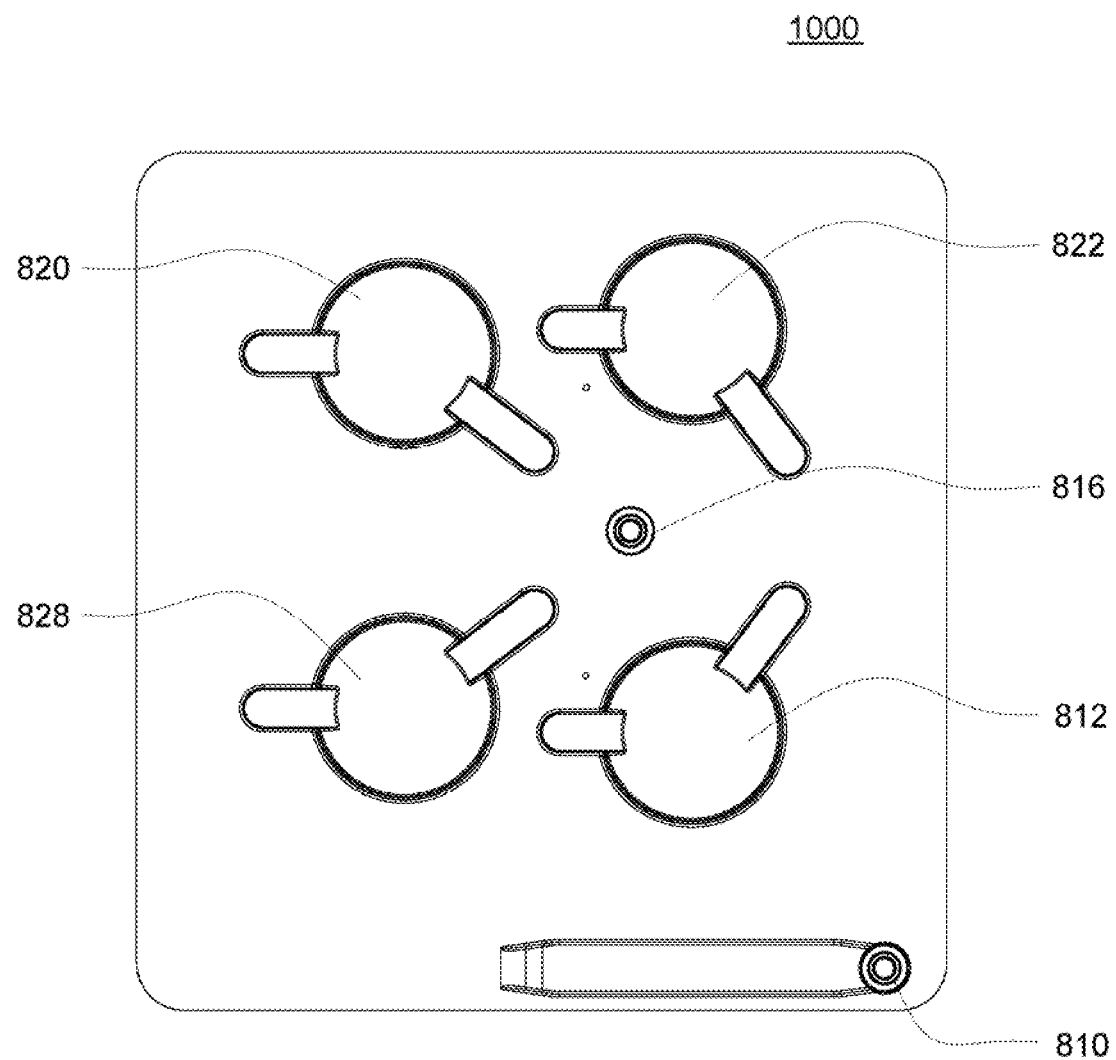

Referring now to FIGS. 10A-10E, the top plate 1000 of the exemplary embodiment of the cassette is shown. Referring first to FIGS. 10A and 10B, the top view of the top plate 1000 is shown. In the exemplary embodiment, the pod pumps 820, 828 and the balancing pods 812, 822 on the top plate, are formed in a similar fashion. In the exemplary embodiment, the pod pumps 820, 828 and balancing pods 812, 822, when assembled with the bottom plate, have a total volume of capacity of 38 ml. However, in various embodiments, the total volume capacity can be greater or less than in the exemplary embodiment. The first fluid inlet 810 and the second fluid outlet 816 are shown.

Figure 10C:
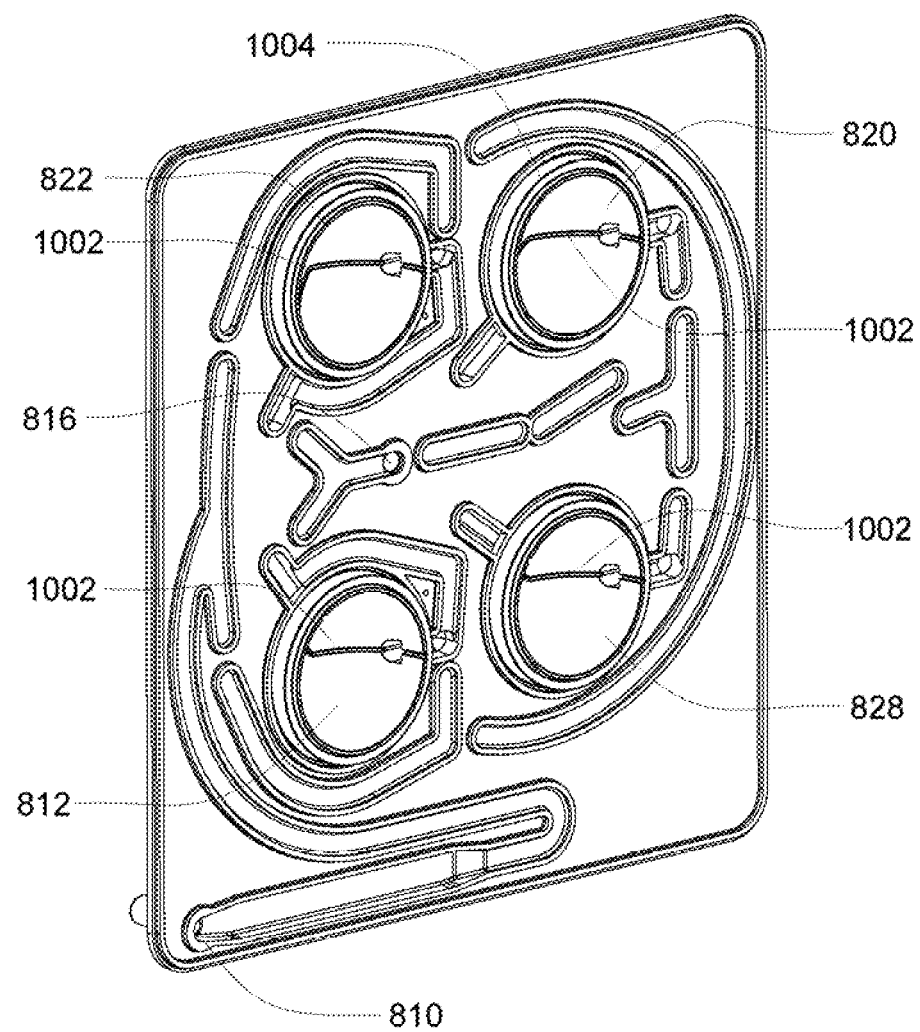
FIGS. 10C-10D are isometric views of the of the exemplary embodiment of the top plate of the exemplary embodiment of the cassette.
Figure 10D:
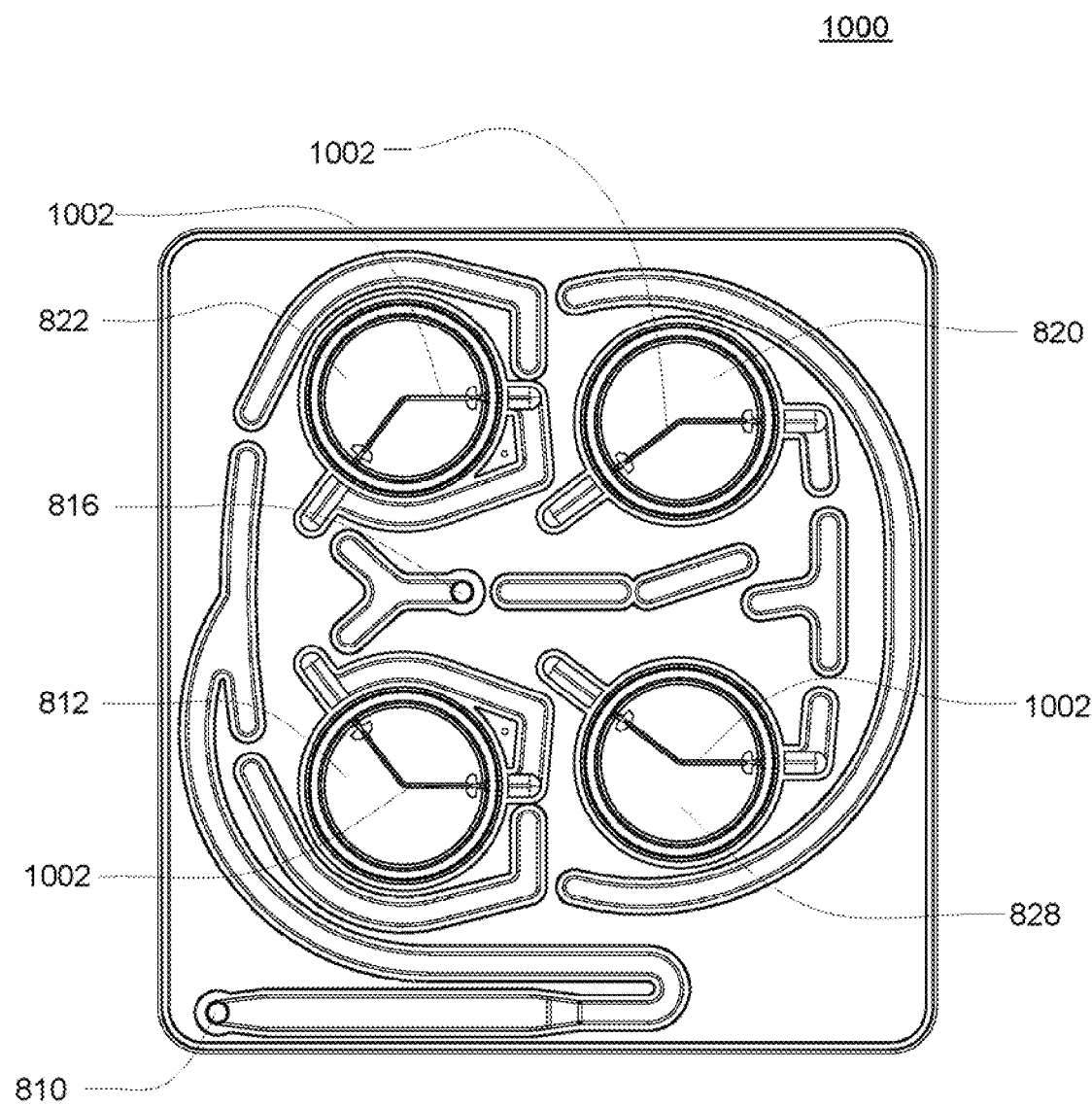

Referring now to FIGS. 10C and 10D, the bottom view of the top plate 1000 is shown. The fluid paths are shown in this view. These fluid paths correspond to the fluid paths shown in FIG. 9B in the midplate 900. The top plate 1000 and the top of the midplate form the liquid or fluid side of the cassette for the pod pumps 820, 828 and for one side of the balancing pods 812, 822. Thus, most of the liquid flow paths are on the top and midplates. The other side of the balancing pods' 812, 822 flow paths is located on the inner side of the bottom plate, not shown here, shown in FIGS. 11A-11B.

Still referring to FIGS. 10C and 10D, the pod pumps 820, 828 and balancing pods 812, 822 include a groove 1002. The groove 1002 is shown having a particular shape, however, in other embodiments, the shape of the groove 1002 can be any shape desirable. The shape shown in FIGS. 10C and 10D is the exemplary embodiment. In all embodiments of the groove 1002, the groove forms a path between the fluid inlet side and the fluid outlet side of the pod pumps 820, 828 and balancing pods 812, 822.

The groove 1002 provides a fluid path whereby when the membrane is at the end of stroke, there is still a fluid path between the inlet and outlet such that the pockets of fluid or air do not get trapped in the pod pump or balancing pod. The groove 1002 is included in both the liquid and air sides of the pod pumps 820, 828 and balancing pods 812, 822 (see FIGS. 11A-11B with respect to the air side of the pod pumps 820, 828 and the opposite side of the balancing pods 812, 822).

The liquid side of the pod pumps 820, 828 and balancing pods 812, 822, in the exemplary embodiment, include a feature whereby the inlet and outlet flow paths are continuous while the outer ring 1004 is also continuous. This feature allows for the seal, formed with the membrane (not shown) to be maintained.

Figure 10E:
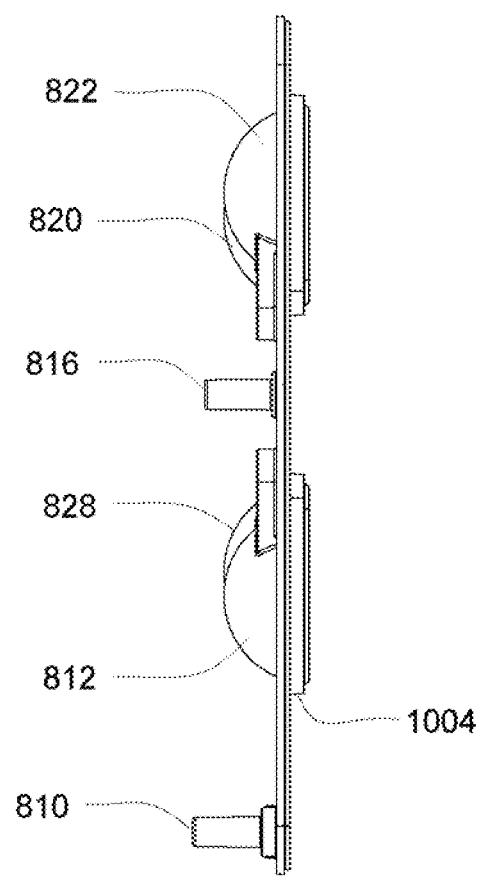
FIG. 10E is a side view of the exemplary embodiment of the top plate of the cassette.

Referring to FIG. 10E, the side view of the exemplary embodiment of the top plate 1000 is shown. The continuous outer ring 1004 of the pod pumps 820, 828 and balancing pods 812, 822 can be seen.

Figure 11A:
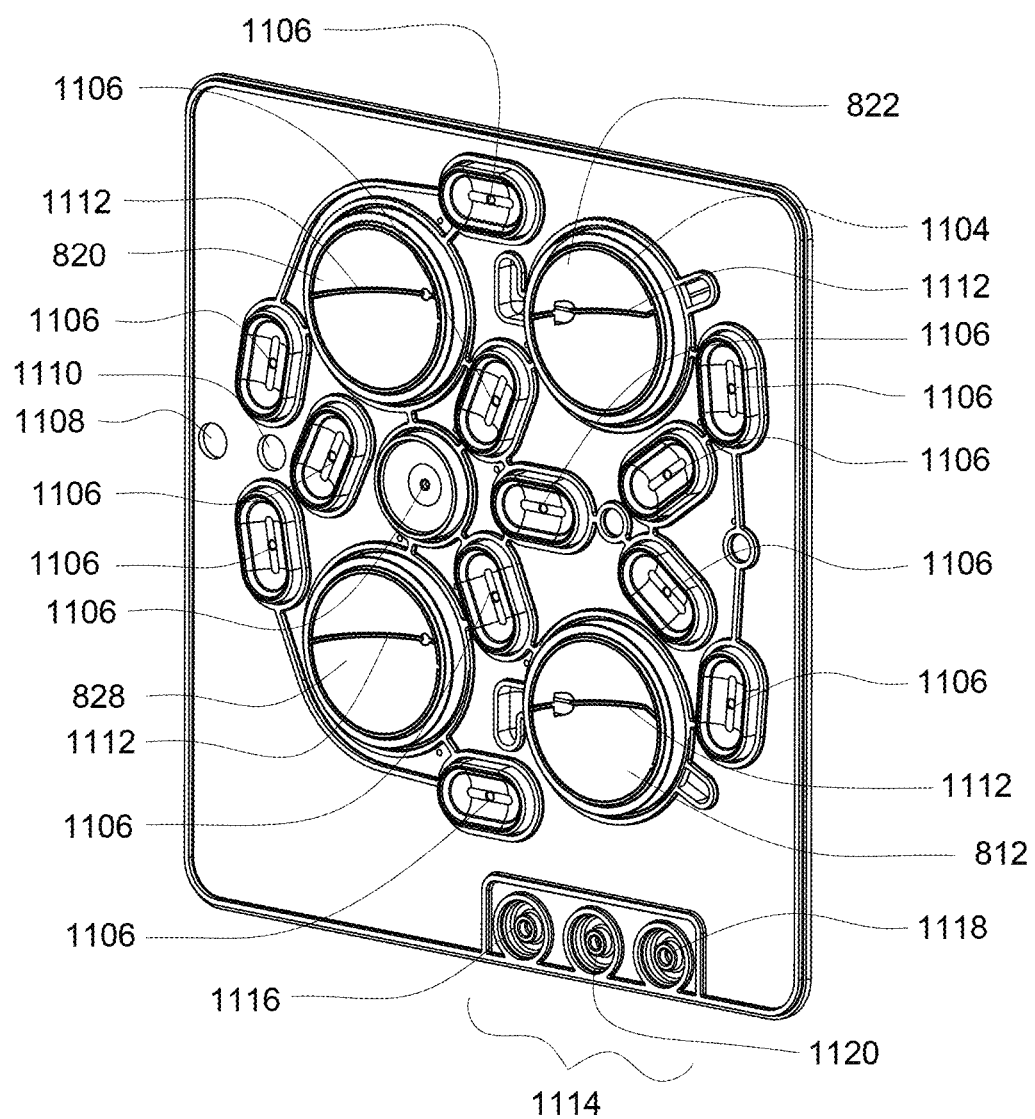
FIGS. 11A and 11B are isometric bottom views of the exemplary embodiment of bottom plate of the exemplary embodiment of the cassette.
Figure 11B:
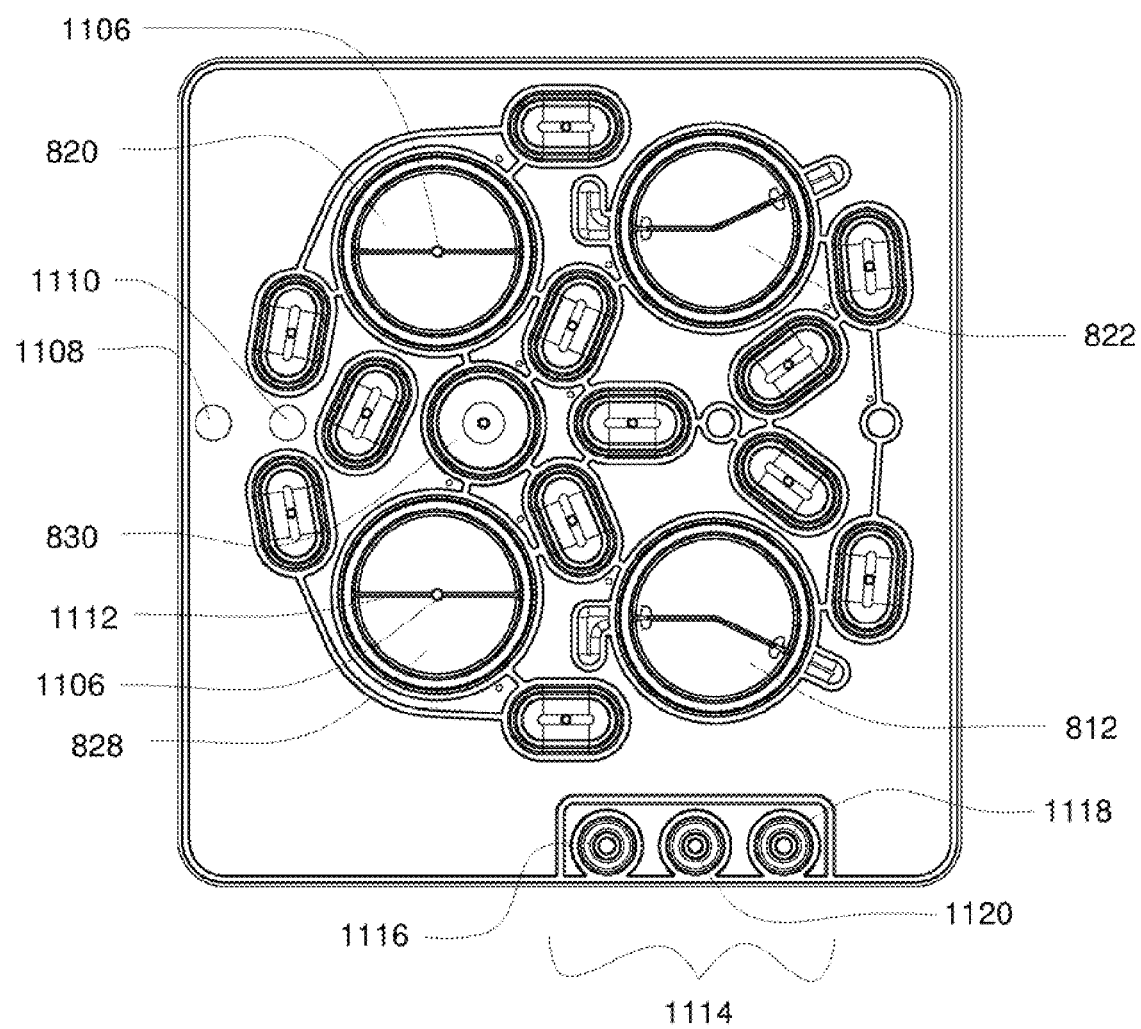

Referring now to FIGS. 11A-11E, the bottom plate 1100 is shown. Referring first to FIGS. 11A and 11B, the inside surface of the bottom plate 1100 is shown. The inside surface is the side that contacts the bottom surface of the midplate (not shown, see FIGS. 9E). The bottom plate 1100 attaches to the air lines (not shown). The corresponding entrance holes for the air that actuates the pod pumps 820, 928 and valves (not shown, see FIG. 9E) in the midplate can be seen 1106. Holes 1108, 1110 correspond to the second fluid inlet and second fluid outlet shown in FIGS. 9G, 824, 826 respectively. The corresponding halves of the pod pumps 820, 828 and balancing pods 812, 822 are also shown, as are the grooves 1112 for the fluid paths. Unlike the top plate, the bottom plate corresponding halves of the pod pumps 820, 828 and balancing pods 812, 822 make apparent the difference between the pod pumps 820, 828 and balancing pods 812, 822. The pod pumps 820, 828 include only a air path on the second half in the bottom plate, while the balancing pods 812, 822 have identical construction to the half in the top plate. Again, the balancing pods 812, 822 balance liquid, thus, both sides of the membrane, not shown, will include a liquid fluid path, while the pod pumps 820, 828 are pressure pumps that pump liquid, thus, one side includes a liquid fluid path and the other side, shown in the bottom plate 1100, includes an air actuation chamber or air fluid path.

In the exemplary embodiment of the cassette, sensor elements are incorporated into the cassette so as to discern various properties of the fluid being pumped. In one embodiment, the three sensor elements are included. In the exemplary embodiment, the sensor elements are located in the sensor cell 1114. The cell 1114 accommodates three sensor elements in the sensor element housings 1116, 1118, 1120. In the exemplary embodiment, two of the sensor housings 1116, 1118 accommodate a conductivity sensor element and the third sensor element housing 1120 accommodates a temperature sensor element. The conductivity sensor elements and temperature sensor elements can be any conductivity or temperature sensor elements in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermister potted in a stainless steel probe. However, in alternate embodiments, a combination temperature and conductivity sensor elements is used similar to the one described in co-pending U.S. patent application entitled Sensor Apparatus Systems, Devices and Methods filed Oct. 12, 2007 and published as Publication No. US 2008/0240929. In this embodiment, the sensor cell 1114 is a single opening to the fluid line or a single connection to the fluid line.

In alternate embodiments, there are either no sensors in the cassette or only a temperature sensor, only one or more conductivity sensors or one or more of another type of sensor.

Still referring to FIGS. 11A and 11B, the actuation side of the metering pump 830 is also shown as well as the corresponding air entrance hole 1106 for the air that actuates the pump.

Figure 11C:
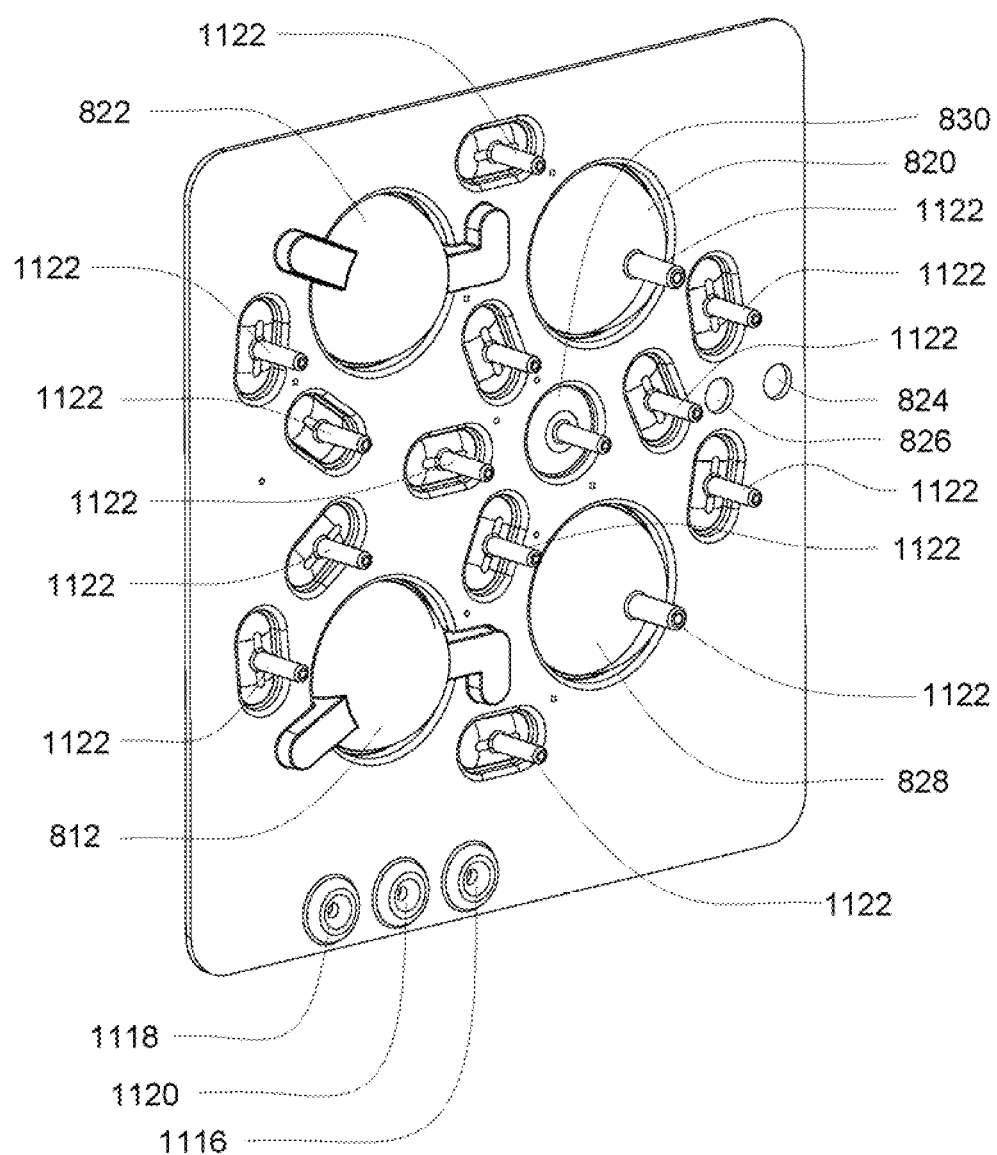
FIGS. 11C and 11D are isometric top views of the exemplary embodiment of the bottom plate of the exemplary embodiment of the cassette.
Figure 11D:
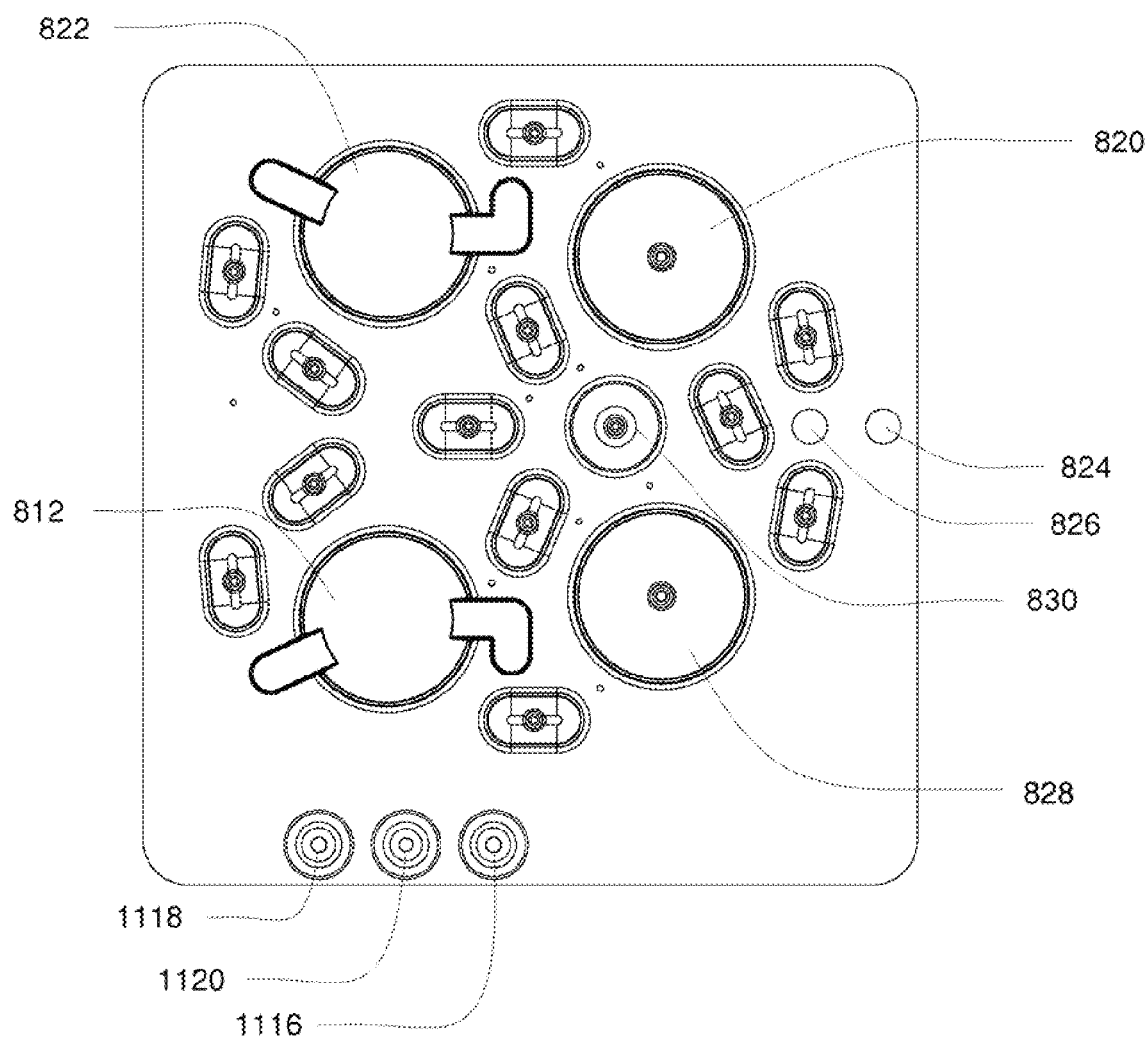

Referring now to FIGS. 11C and 11D, the outer side of the bottom plate 1100 is shown. The valve, pod pumps 820, 828 and metering pump 830 air line connection points 1122 are shown. Again, the balancing pods 812, 822 do not have air line connection points as they are not actuated by air. As well, the corresponding openings in the bottom plate 1100 for the second fluid outlet 824 and second fluid inlet 826 are shown.

Figure 11E:
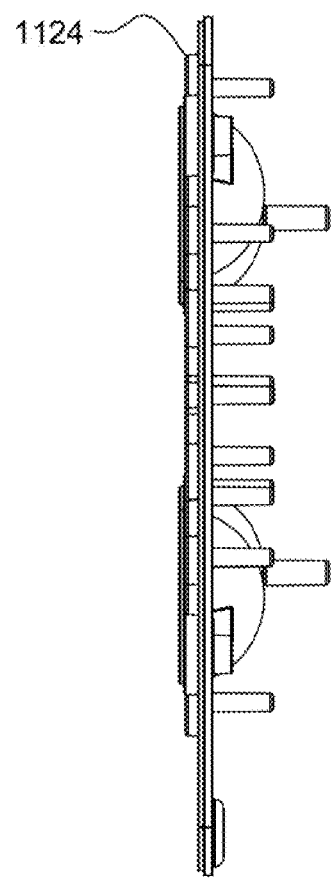
FIG. 11E is a side view of the exemplary embodiment of the bottom plate of the exemplary embodiment of the cassette.

Referring now to FIG. 11E, a side view of the bottom plate 1100 is shown. In the side view, the rim 1124 that surrounds the inner bottom plate 1100 can be seen. The rim 1124 is raised and continuous, providing for a connect point for the membrane (not shown). The membrane rests on this continuous and raised rim 1124 providing for a seal between the half of the pod pumps 820, 828 and balancing pods 812, 822 in the bottom plate 1100 and the half of the pod pumps 820, 828 and balancing pods 812, 822 in the top plate (not shown, see FIGS. 10A-10D).

5.1 Membranes

Figure 6A:
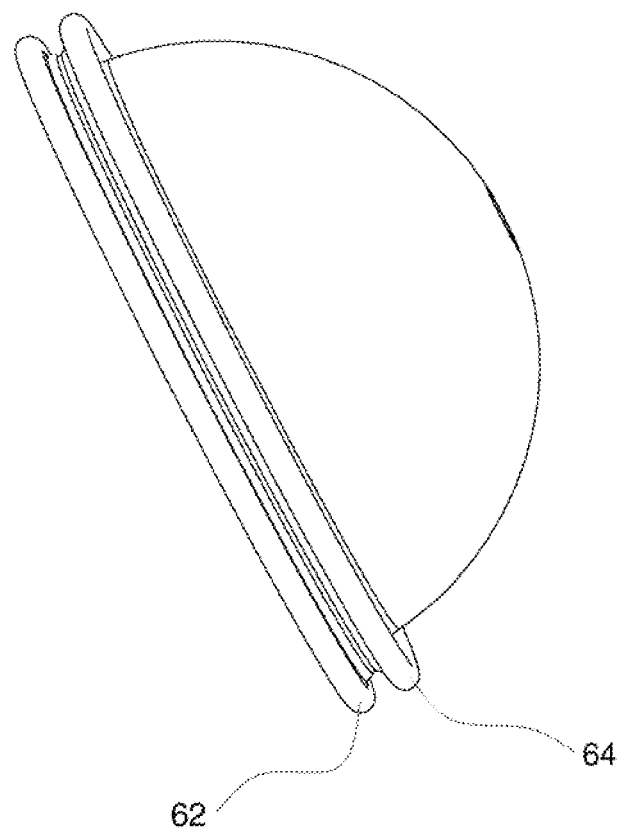
FIGS. 6A and 6B are pictorial views of a double ring membrane with a smooth surface.

In the exemplary embodiment, the membrane is a double o-ring membrane as shown in FIG. 6A. However, in some embodiments, a double o-ring membrane having texture, including, but not limited to, the various embodiments in FIGS. 6B-6F may be used.

Figure 6B:
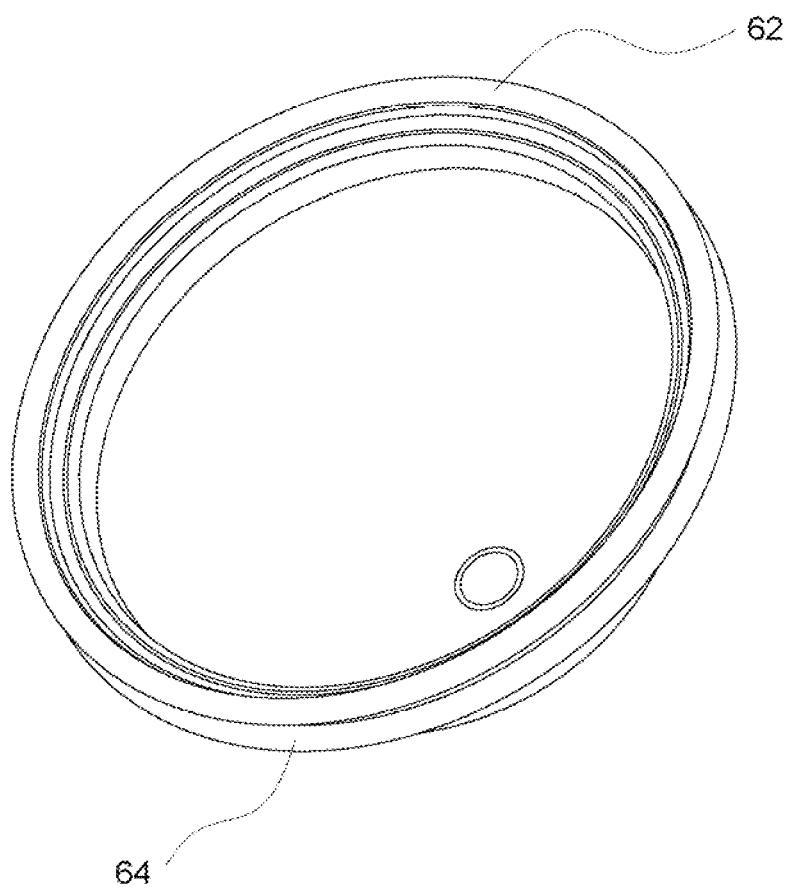
Figure 6C:
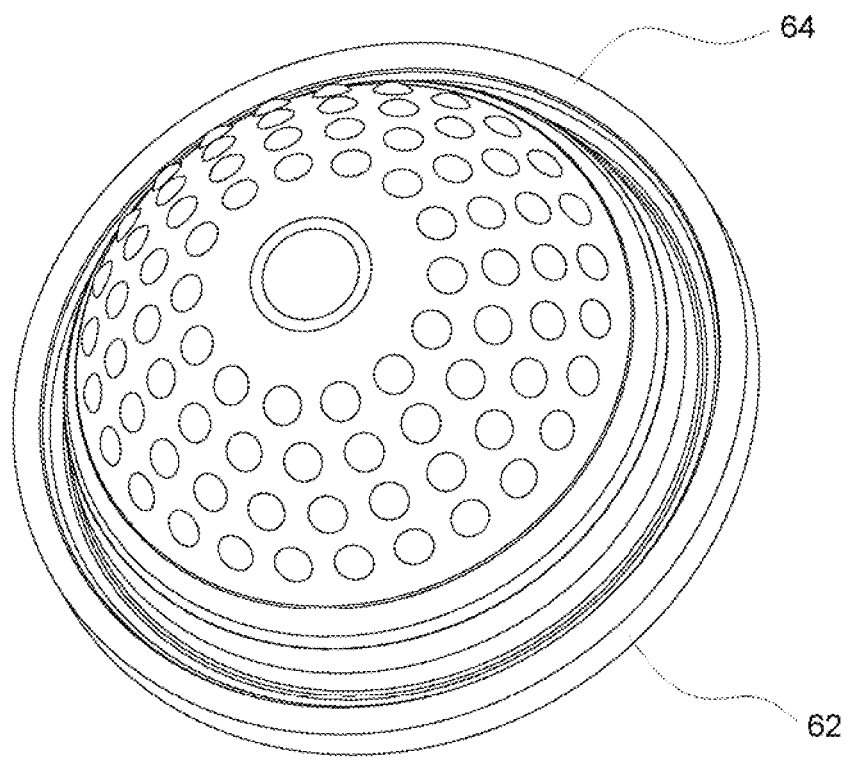
FIGS. 6C and 6D are pictorial views of a double ring membrane with a dimple surface.
Figure 6D:
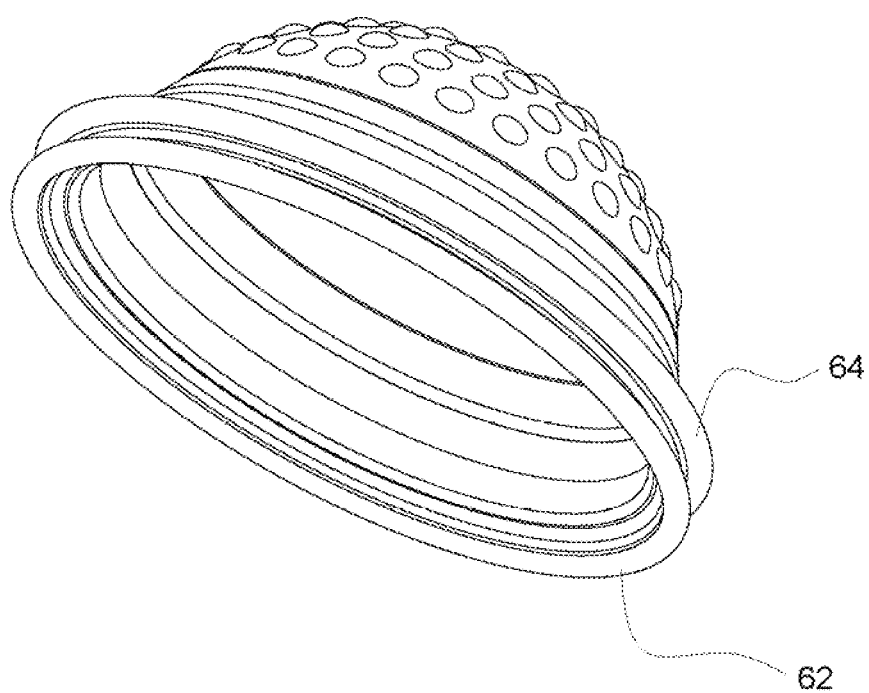
Figure 6E:
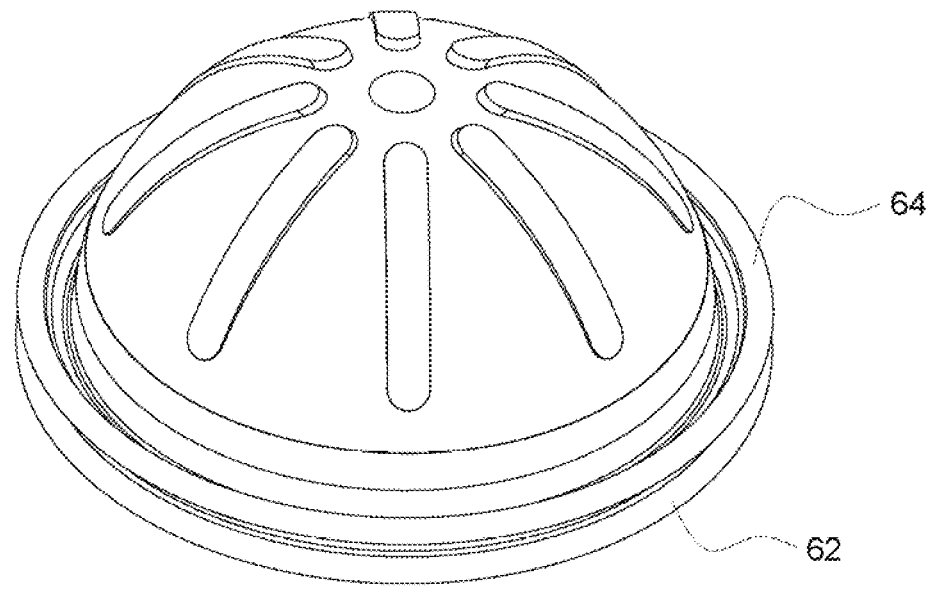
FIGS. 6E and 6F are pictorial views of double ring membranes with variable surfaces.
Figure 6F:
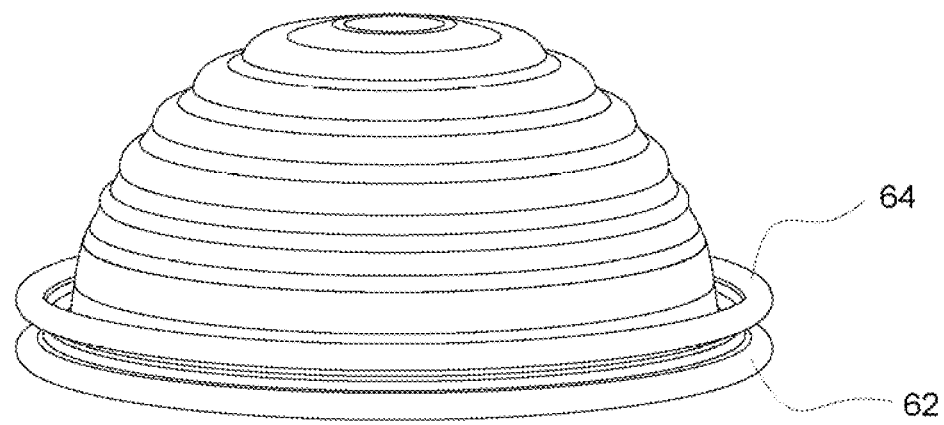
Figure 6G:
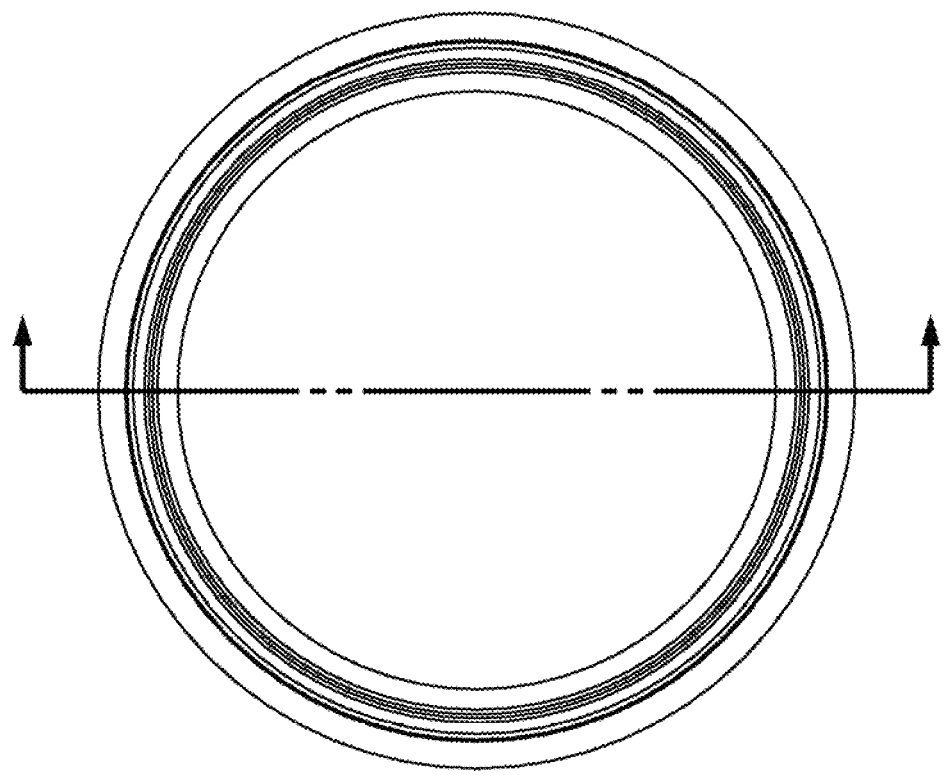
FIG. 6G is a cross sectional view of a double ring membrane with a variable surface.
Figure 6G:
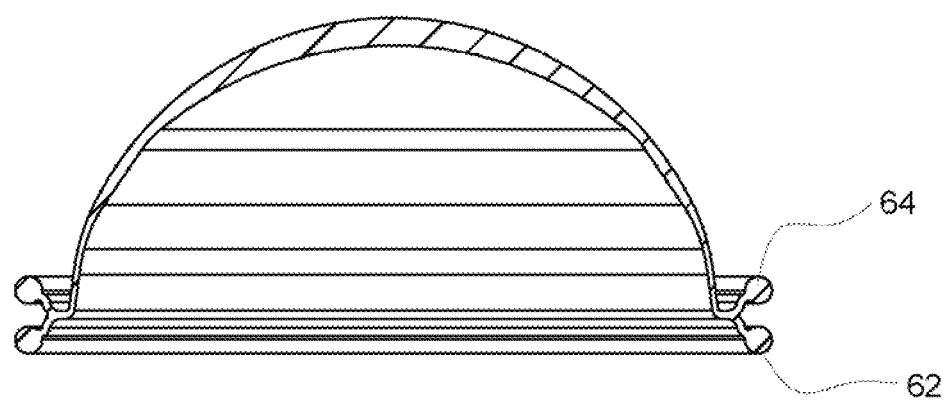
Figure 12A:
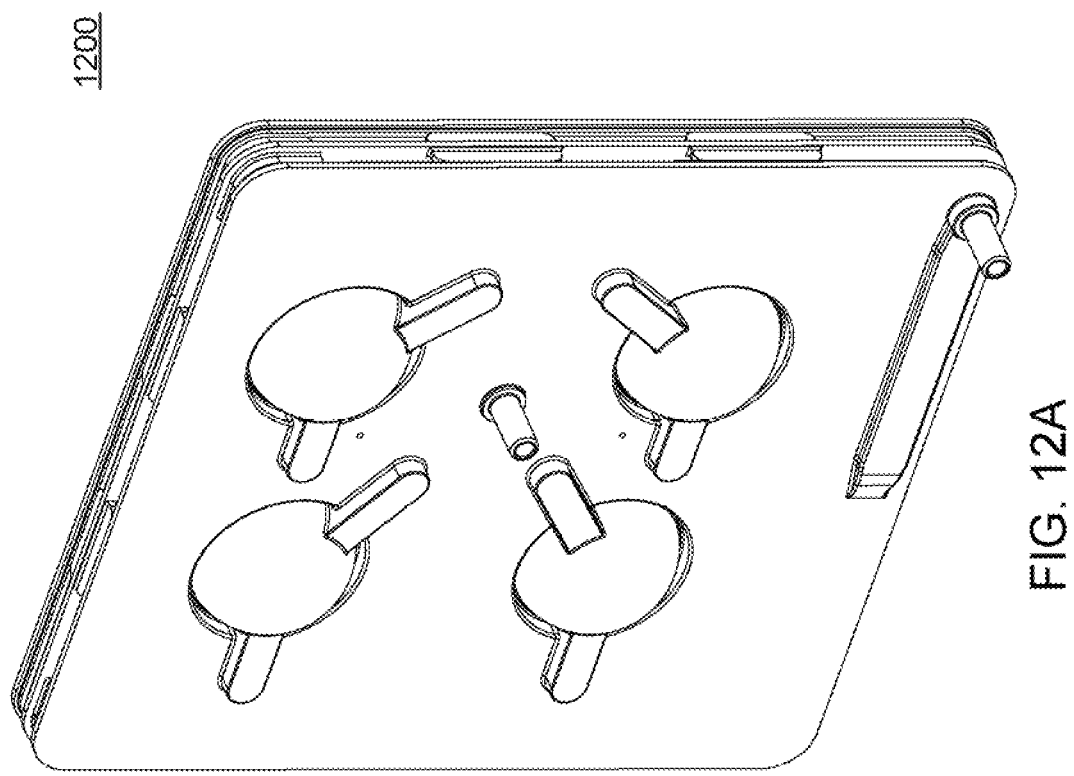
FIG. 12A is an isometric view of the top of the assembled exemplary embodiment of the cassette.
Figure 12B:
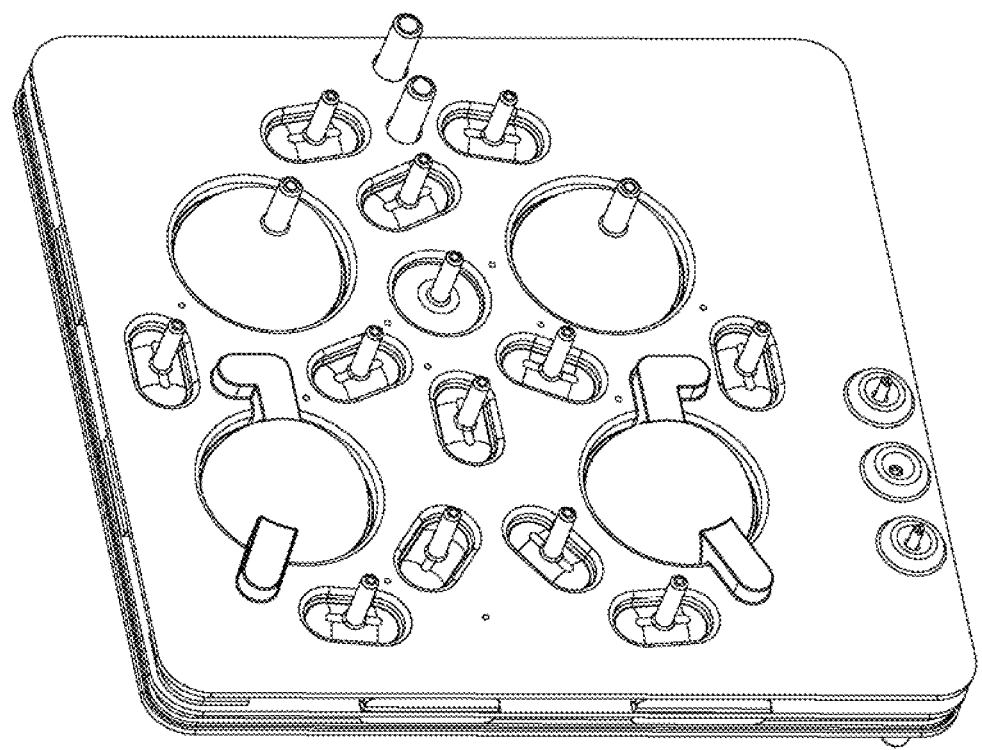
FIG. 12B is an isometric view of the bottom of the assembled exemplary embodiment of the cassette.
Figure 12C:
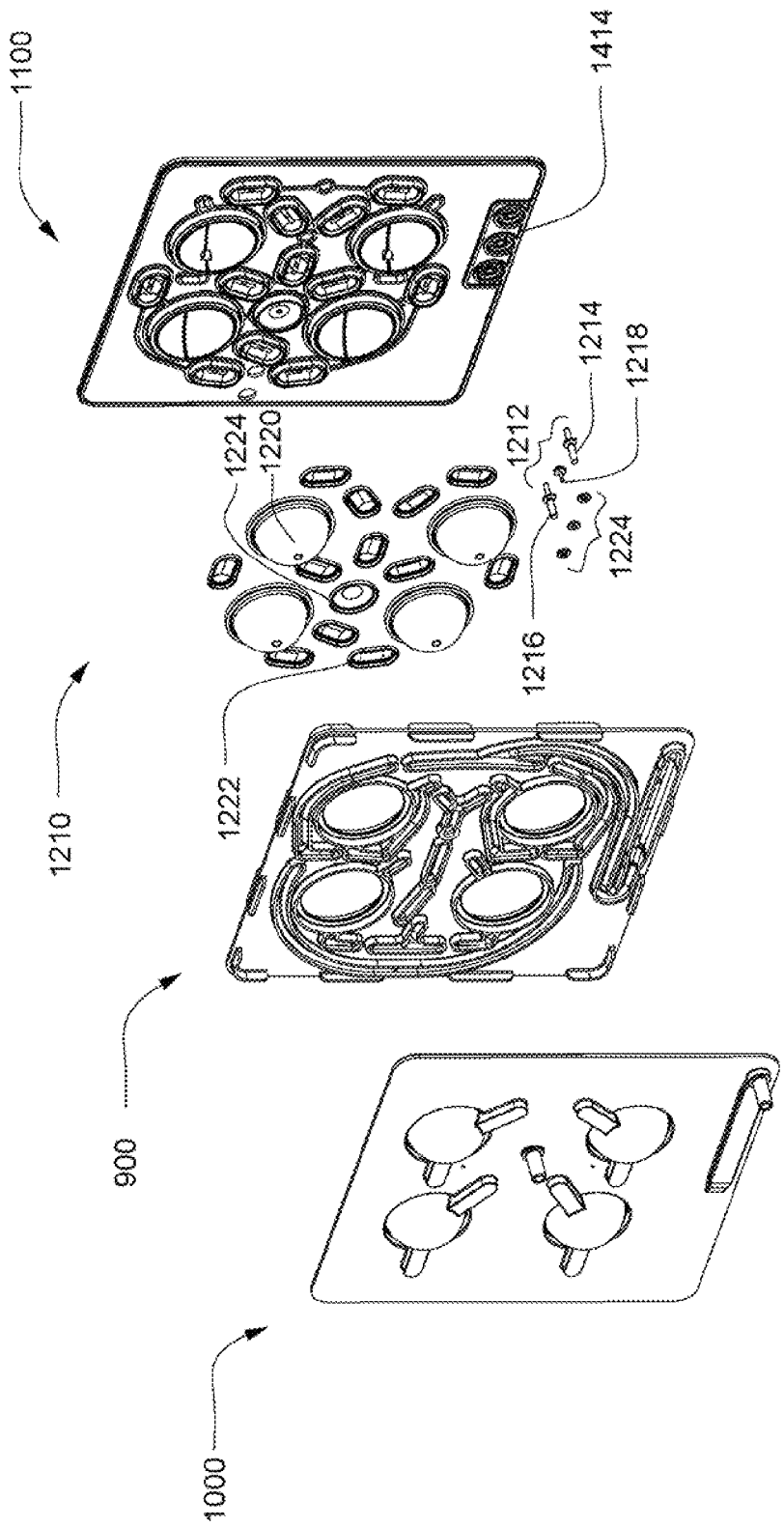
FIG. 12C is an exploded view of the assembled exemplary embodiment of the cassette.
Figure 12D:
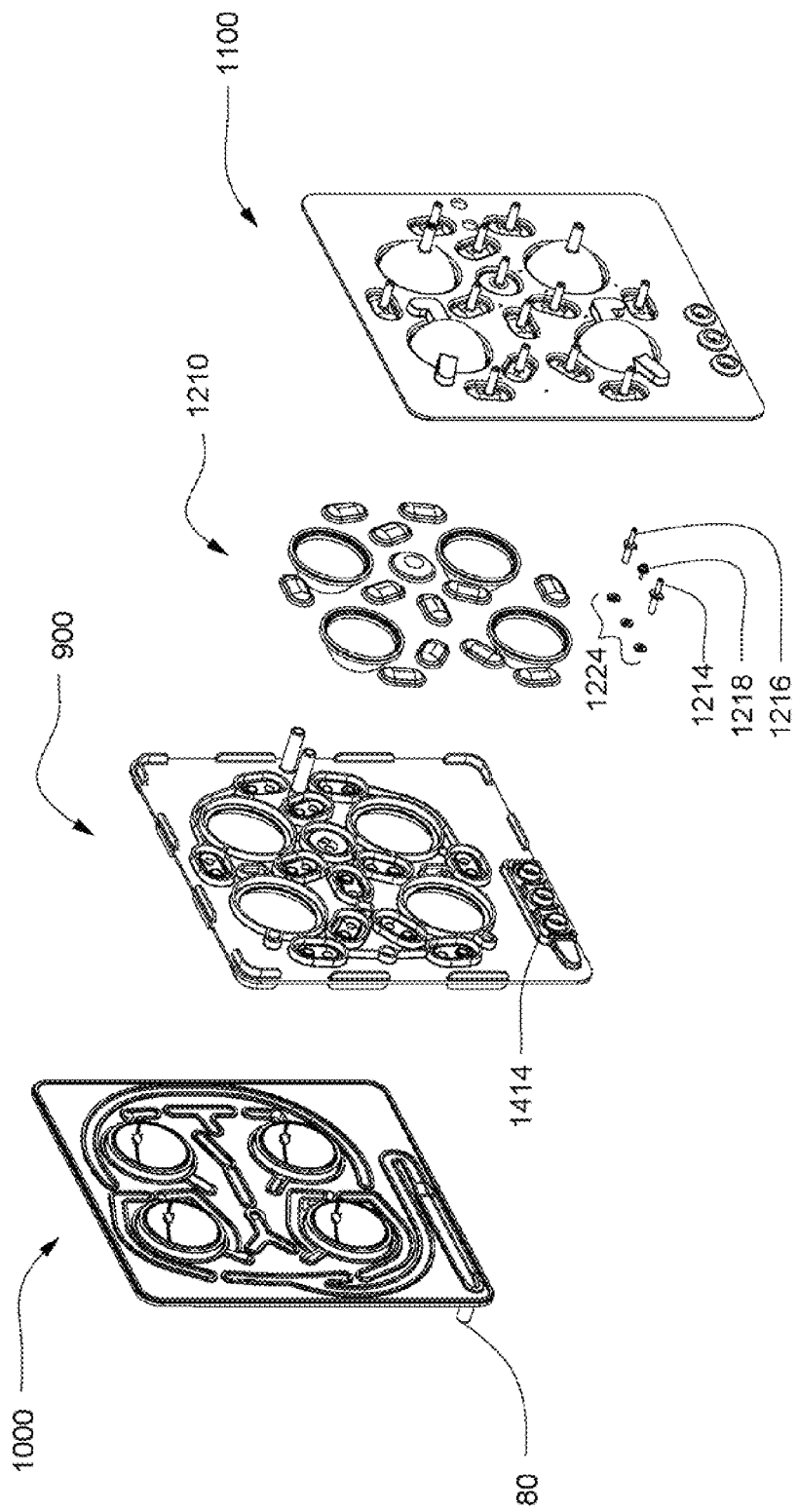
FIG. 12D is an exploded view of the assembled exemplary embodiment of the cassette.

Referring now to FIGS. 12A and 12B, the assembled exemplary embodiment of the cassette 1200 is shown. FIGS. 12C and 12D are exploded views of the exemplary embodiment of the cassette 1200. The membranes 1210 are shown. As can be seen from FIGS. 12C and 12D, there is one membrane 1220 for each of the pods pumps and balancing pods. In the exemplary embodiment, the membrane for the pod pumps and the balancing pods are identical. The membrane in the exemplary embodiment is a double o-ring membrane as shown in FIGS. 6A-6B. However, in alternate embodiments, any double o-ring membrane may be used, including, but not limited to, the various embodiments shown in FIGS. 6C-6F. However, in other embodiments, the double o-ring membrane is used in the balancing pods, but a single o-ring membrane, as shown in FIGS. 4A-4D is used in the pod pumps.

Figure 5A:
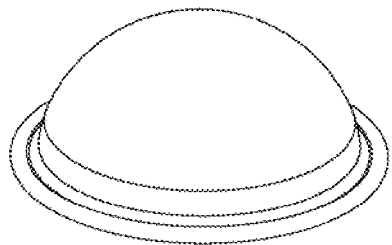
FIGS. 5A-5D are pictorial views of various embodiments of variable membranes.
Figure 5B:
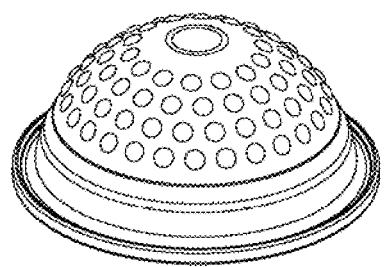
Figure 5C:
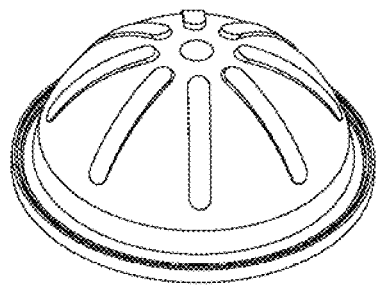
Figure 5D:
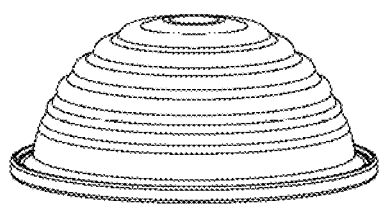
Figure 5E:
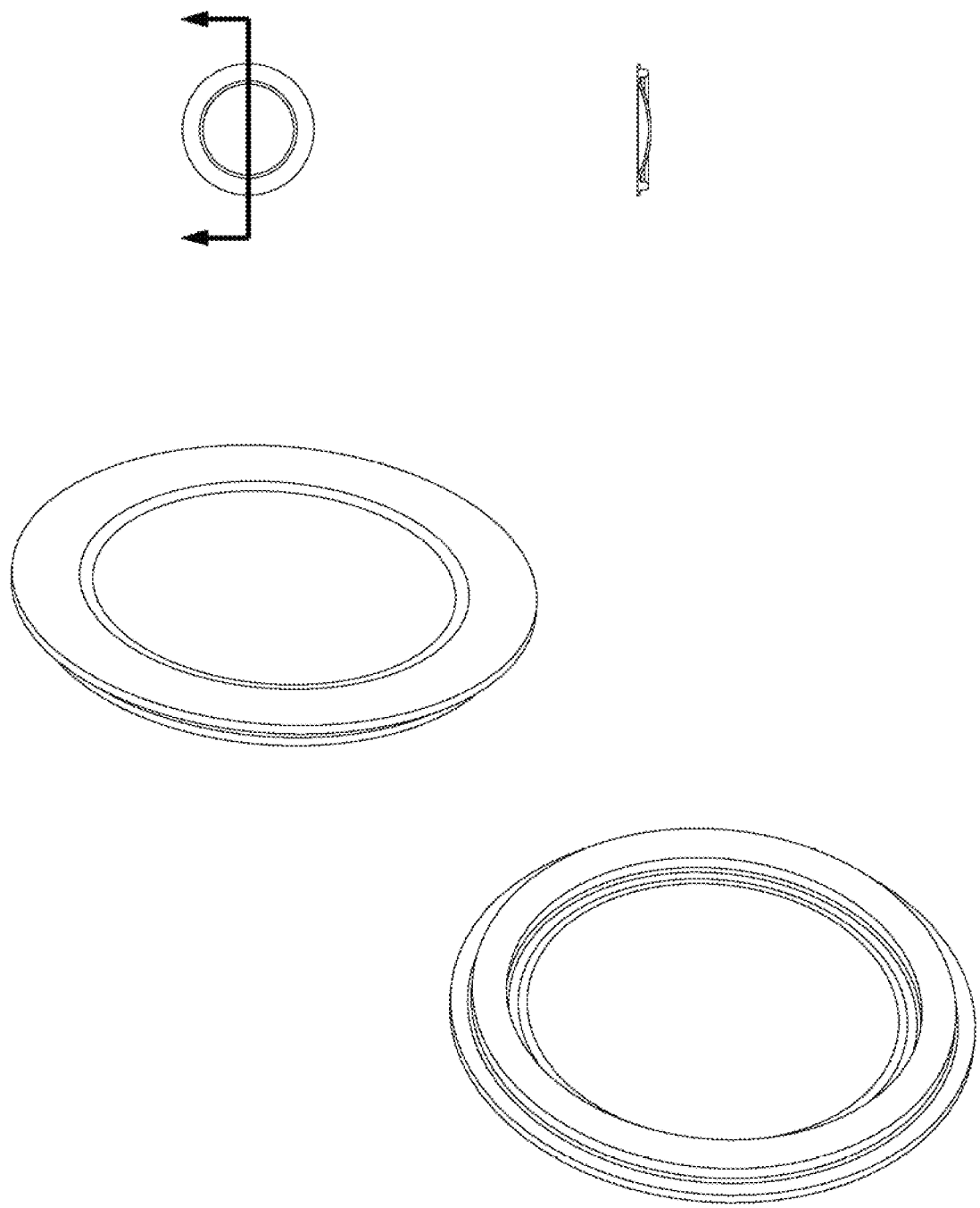
FIGS. 5E-5H are pictorial views of various embodiments of the metering pump membrane.
Figure 5F:
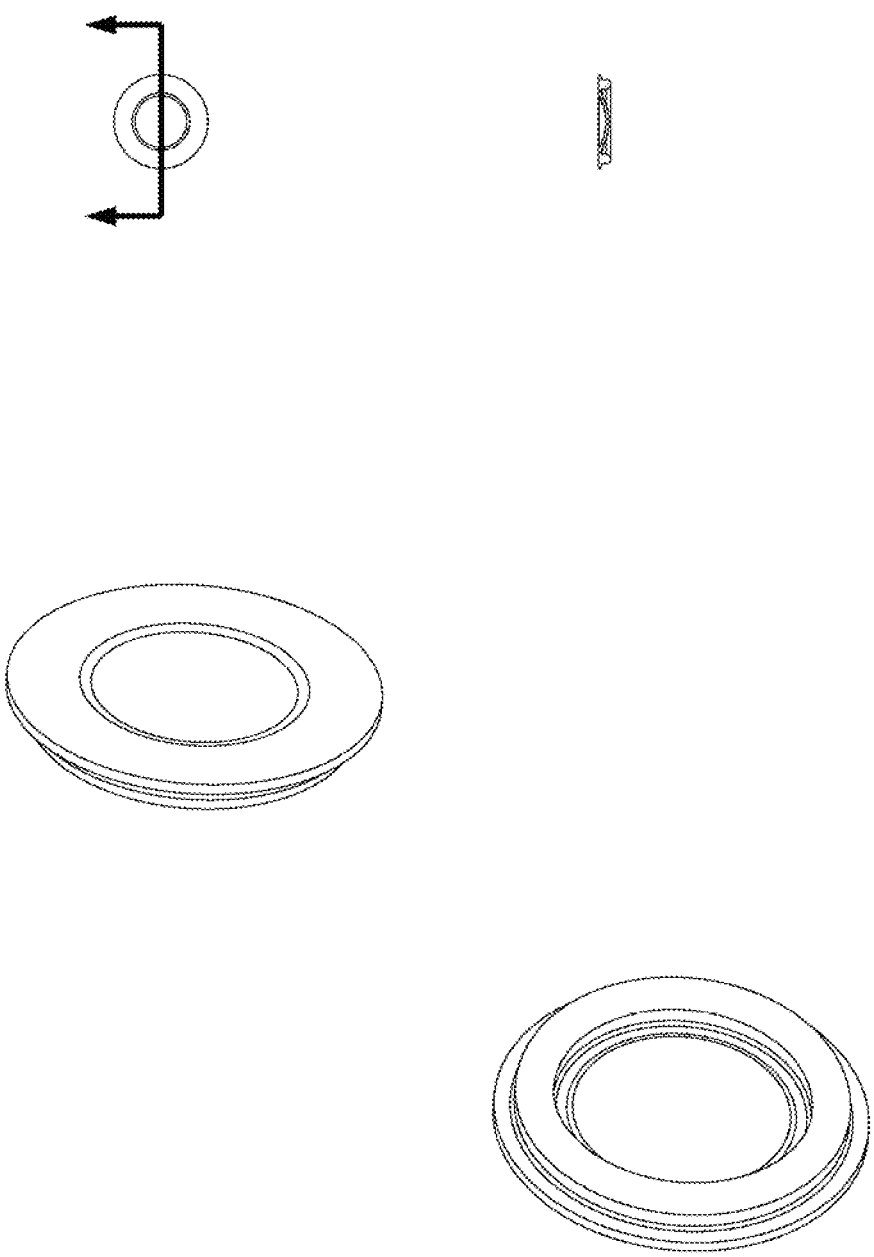
Figure 5G:
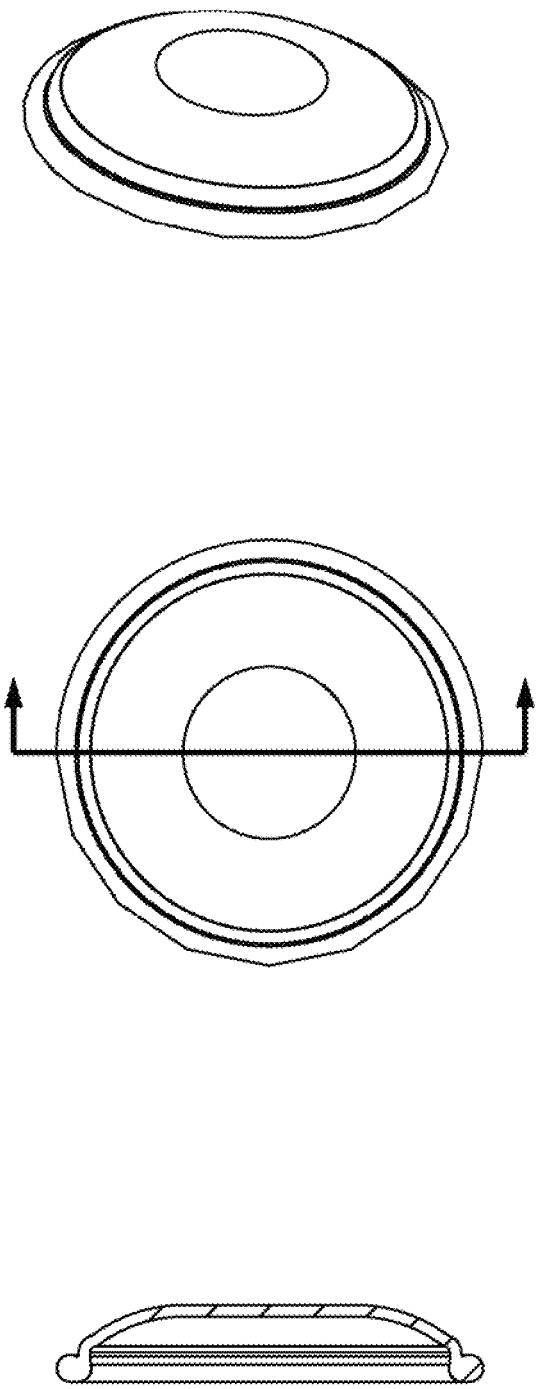
Figure 5H:
Figure 5H:
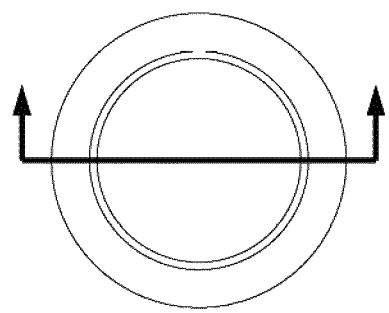
Figure 5H:

The membrane used in the metering pump 1224, in the preferred embodiment, is shown in more detail in FIG. 5G, with alternate embodiments shown in FIGS. 5E, 5F and 5H. The membrane used in the valves 1222 is shown in more detail in FIG. 2E, with alternate embodiments shown in FIGS. 2F-2G. However, in alternate embodiments, the metering pump membrane as well as the valve membranes may contain textures, for example, but not limited to, the textures shown on the pod pump/ balancing pod membranes shown in FIGS. 5A-5D.

One embodiment of the conductivity sensor elements 1214, 1216 and the temperature sensor 1218, which make up the sensor cell 1212, are also shown in FIGS. 12C and 12D. Still referring to FIGS. 12C and 12D, the sensor cell housing 1414 includes areas on the bottom plate 1100 and the midplate 900. O-rings seal the sensor housing 1414 from the fluid lines located on the upper side of the midplate 900 shown in FIG. 12C and the inner side of the top plate 1000 shown in FIG. 12D. However, in other embodiments, an o-ring is molded into the sensor cell, or any other method of sealing can be used.

5.2 Cross Sectional Views

Figure 13A:
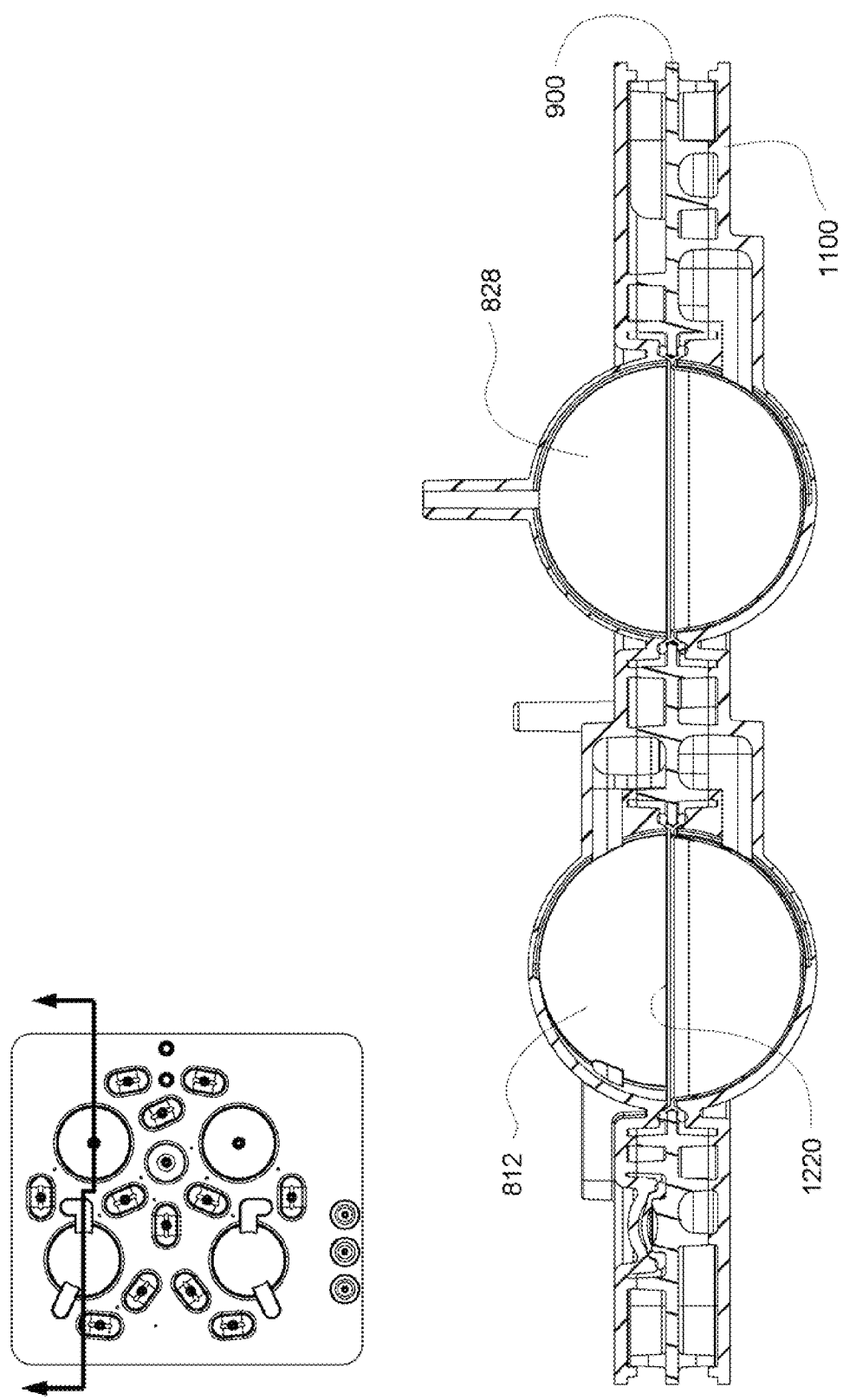
FIGS. 13A-13C show cross sectional views of the exemplary embodiment of the assembled cassette.
Figure 13B:
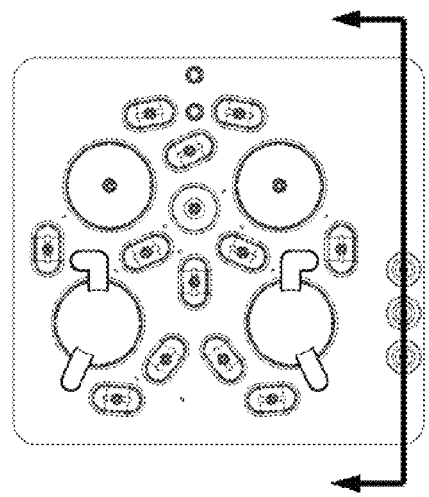
Figure 13B:
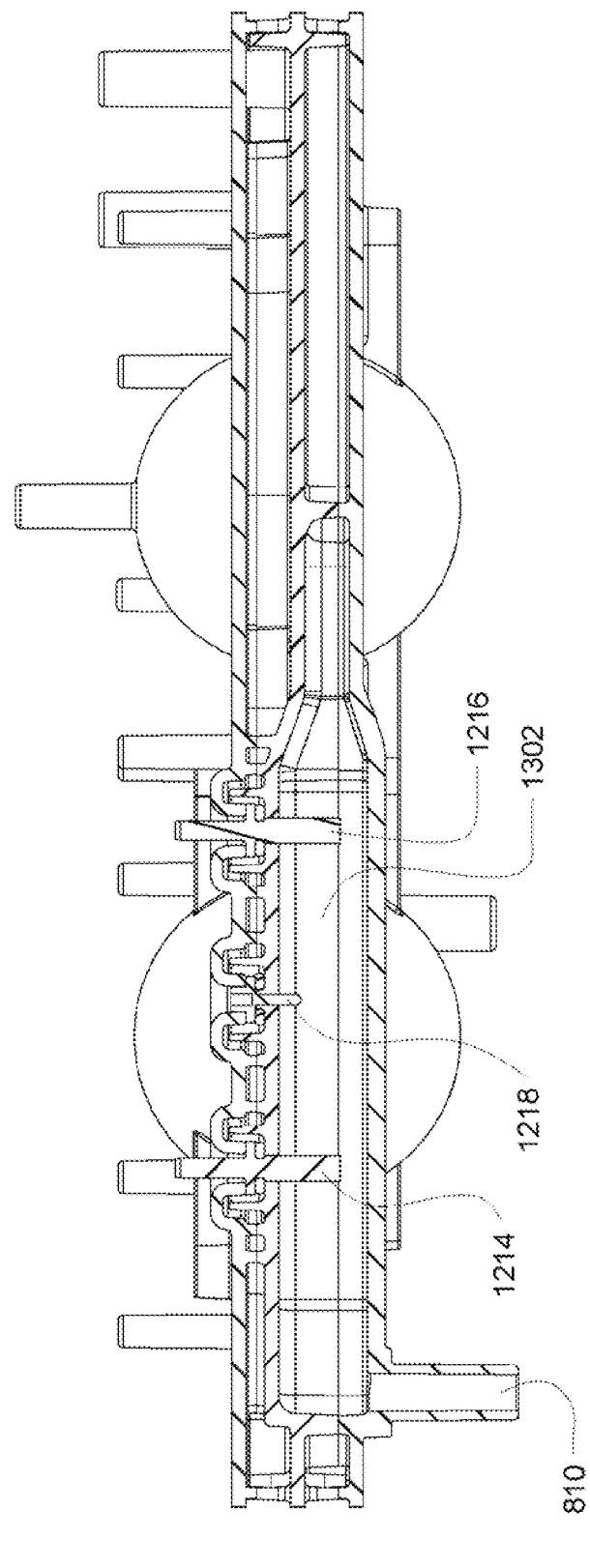
Figure 13C:
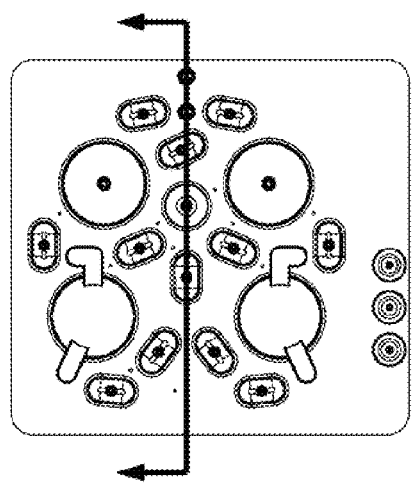
Figure 13C:
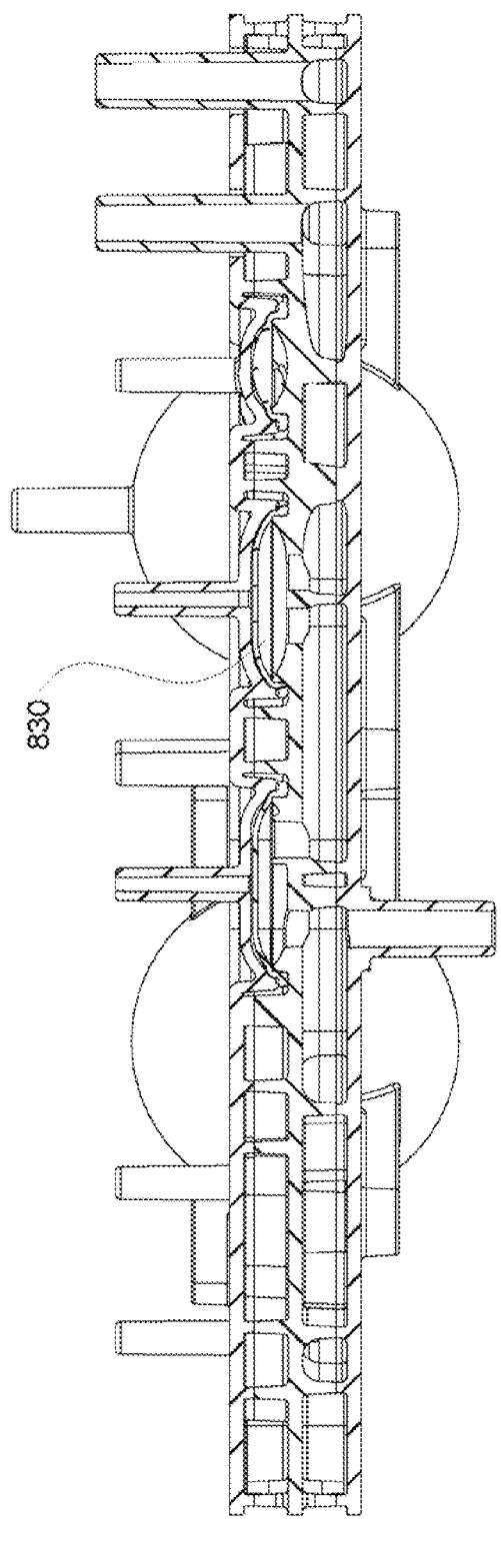
Figure 14A:
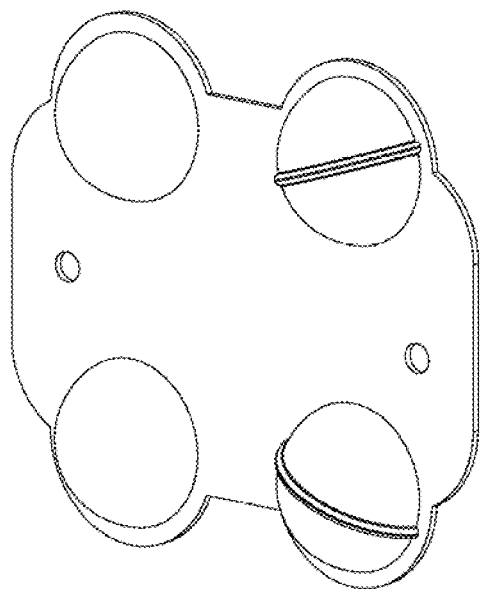
FIGS. 14A-14B show isometric and top views of an alternate embodiment of the top plate according to an alternate embodiment of the cassette.
Figure 14B:
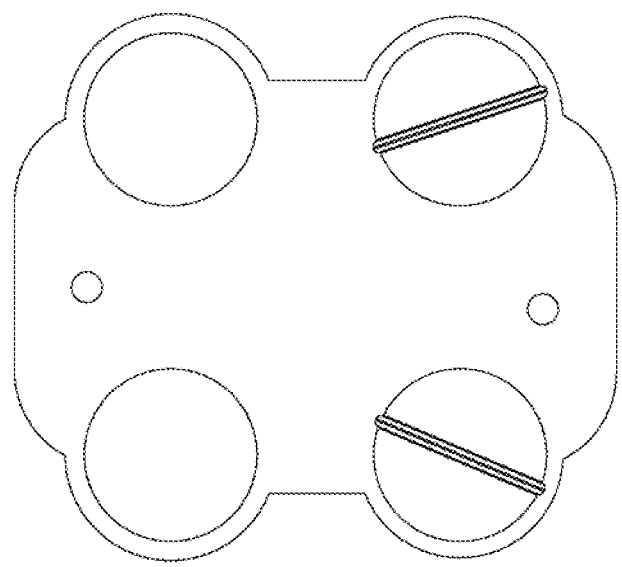
Figure 14C:
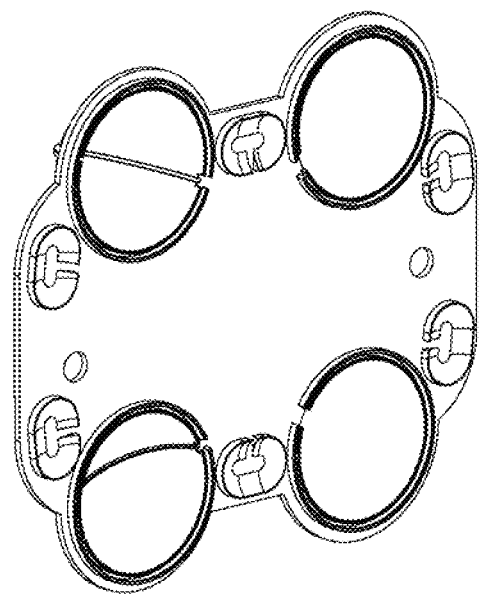
FIGS. 14C-14D show isometric and bottom views of an alternate embodiment of the top plate according to an alternate embodiment of the cassette.
Figure 14D:
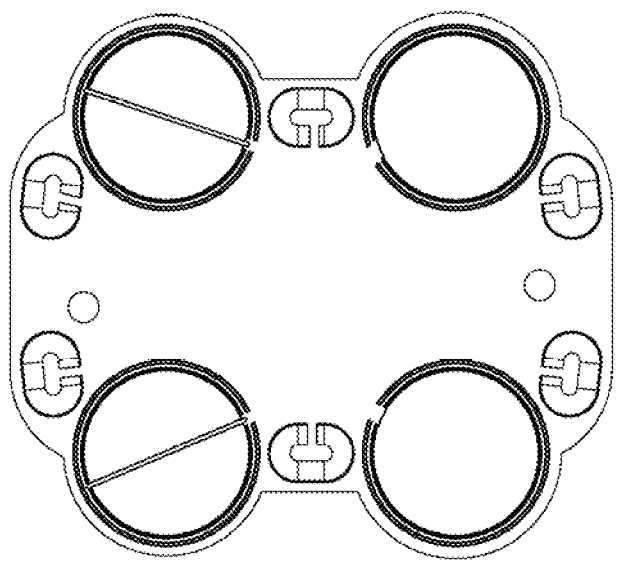
Figure 14E:
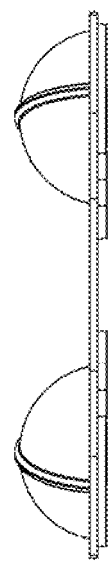
FIG. 14E shows a side view of the alternate embodiment of the top plate.
Figure 15A:
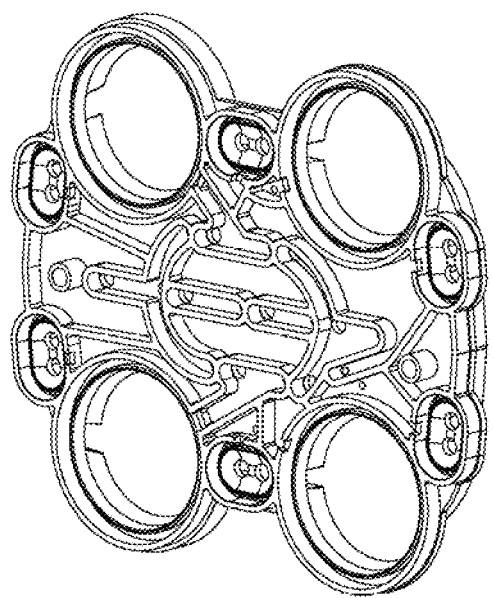
FIGS. 15A-15B show isometric and top views of an alternate embodiment of the midplate according to an alternate embodiment of the cassette.
Figure 15B:
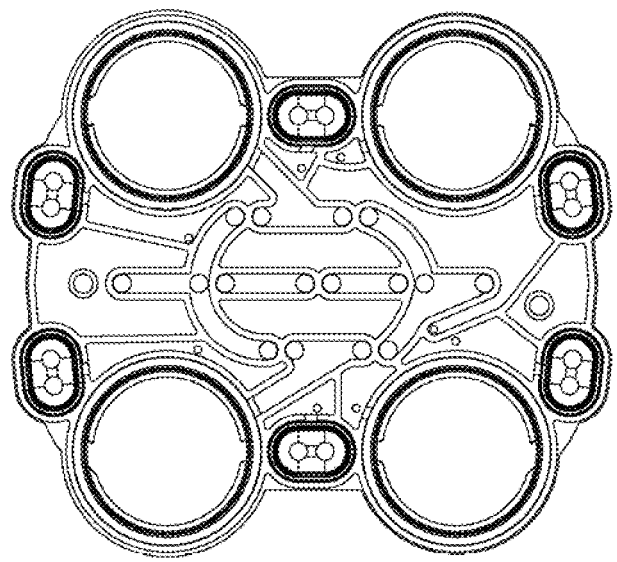
Figure 15C:
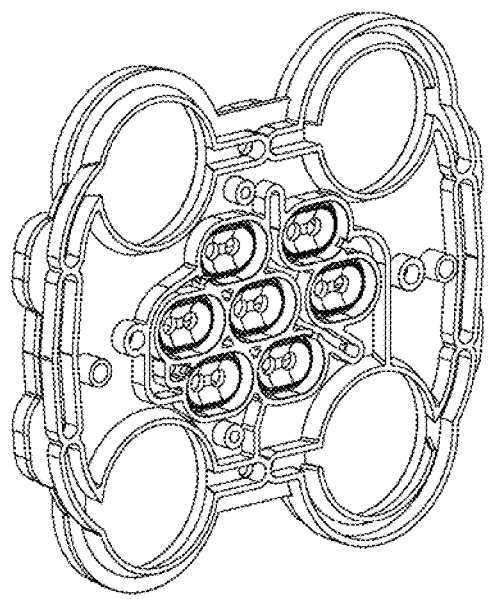
FIGS. 15C-15D show isometric and bottom views of an alternate embodiment of the midplate according to an alternate embodiment of the cassette.
Figure 15D:
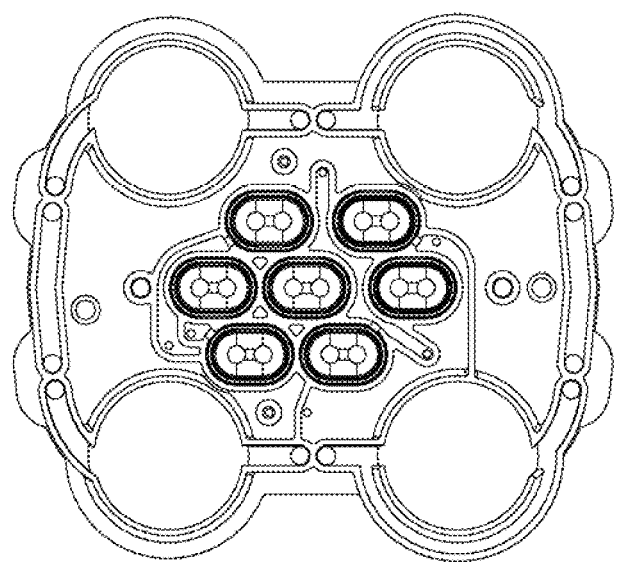
Figure 15E:
FIG. 15E shows a side view of the alternate embodiment of the midplate.
Figure 16A:
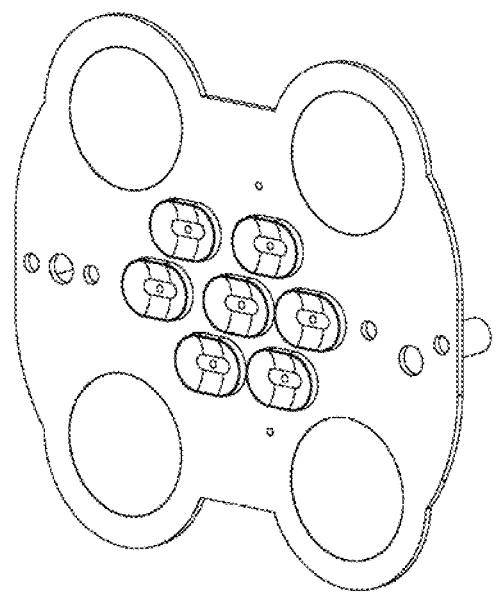
FIGS. 16A-16B show isometric and top views of an alternate embodiment of the bottom plate according to an alternate embodiment of the cassette.
Figure 16B:
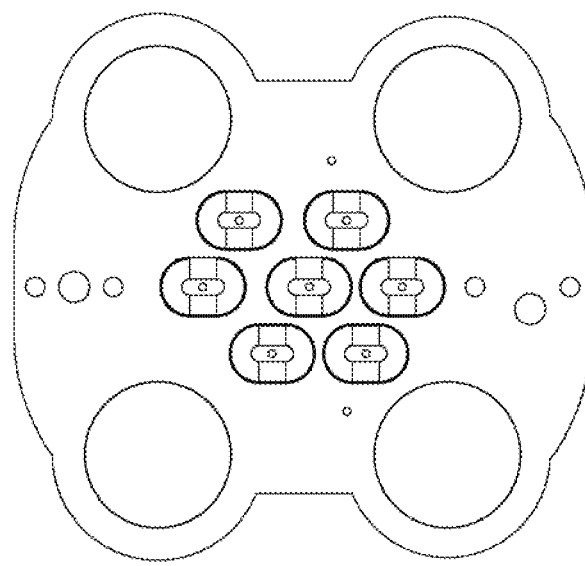
Figure 16C:
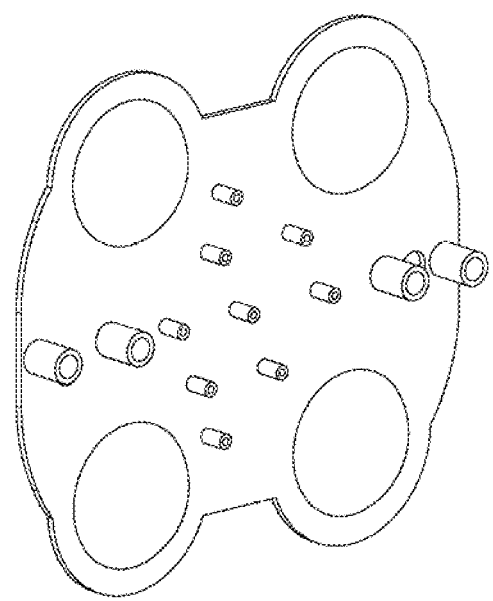
FIGS. 16C-16D show isometric and bottom views of an alternate embodiment of the bottom plate according to an alternate embodiment of the cassette.
Figure 16D:
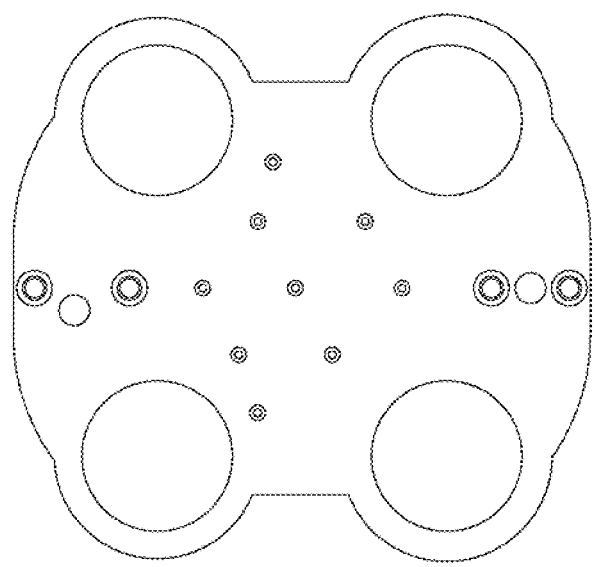
Figure 16E:
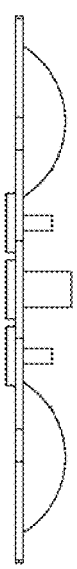
FIG. 16E shows a side view of the alternate embodiment of the bottom plate.

Referring now to FIGS. 13A-13C, various cross sectional views of the assembled cassette are shown. Referring first to FIG. 13A, the membrane 1220 is shown in a balancing pod 812 and a pod pump 828. As can be seen from the cross section, the double o-ring of the membrane 1220 is sandwiched by the midplate 900, the bottom plate 1100 and the top plate 1000.

Referring now to FIG. 13B, the two conductivity sensor elements 1214, 1216 and the temperature sensor element 1218 are shown. As can be seen from the cross section, the sensor elements 1214, 1216, 1218 are in the fluid line 1302. Thus, the sensor elements 1214, 1216, 1218 are in fluid connection with the fluid line and can determine sensor data of the first fluid entering the first fluid inlet 810. Referring now to FIG. 13C, this cross sectional view shows the metering pump 830 as well as the structure of the valves.

As described above, the exemplary embodiment is one cassette embodiment that incorporates the exemplary fluid flow-path schematic shown in FIG. 8A. However, there are alternate embodiments of the cassette that incorporate many of the same features of the exemplary embodiment, but in a different structural design. Additionally, there are alternate embodiment fluid flow paths, for example, the fluid flow path schematic shown in FIG. 8B. The alternate embodiment cassette structure corresponding to this schematic is shown in FIGS. 14A-18.

Referring now to FIGS. 14A-14E, views of an alternate embodiment of the top plate 1400 are shown. The features of the top plate 1400 are alternate embodiments of corresponding features in the exemplary embodiment.

Referring now to FIGS. 15A-15E, views of an alternate embodiment of the midplate 1500 are shown. FIGS. 16A-16E show views of an alternate embodiment of the bottom plate 1600.

Figure 17A:
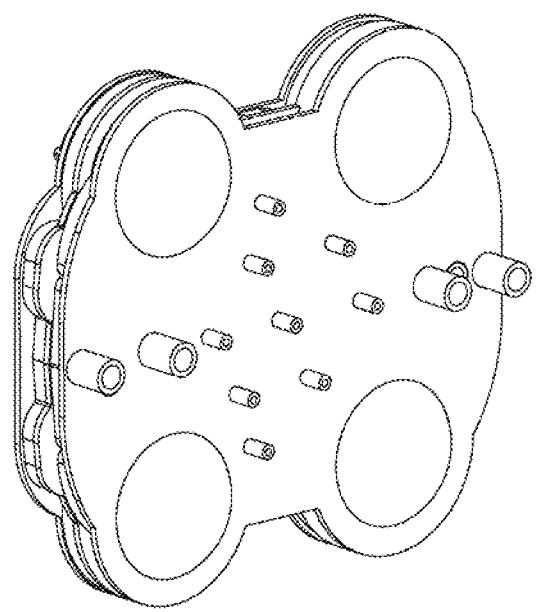
FIG. 17A is an isometric top view of an assembled alternate embodiment of the cassette.
Figure 17B:
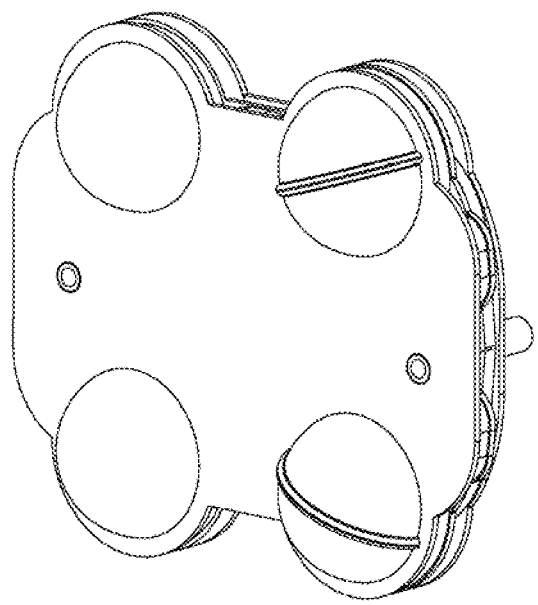
FIG. 17B is an isometric bottom view of an assembled alternate embodiment of the cassette.
Figure 17C:
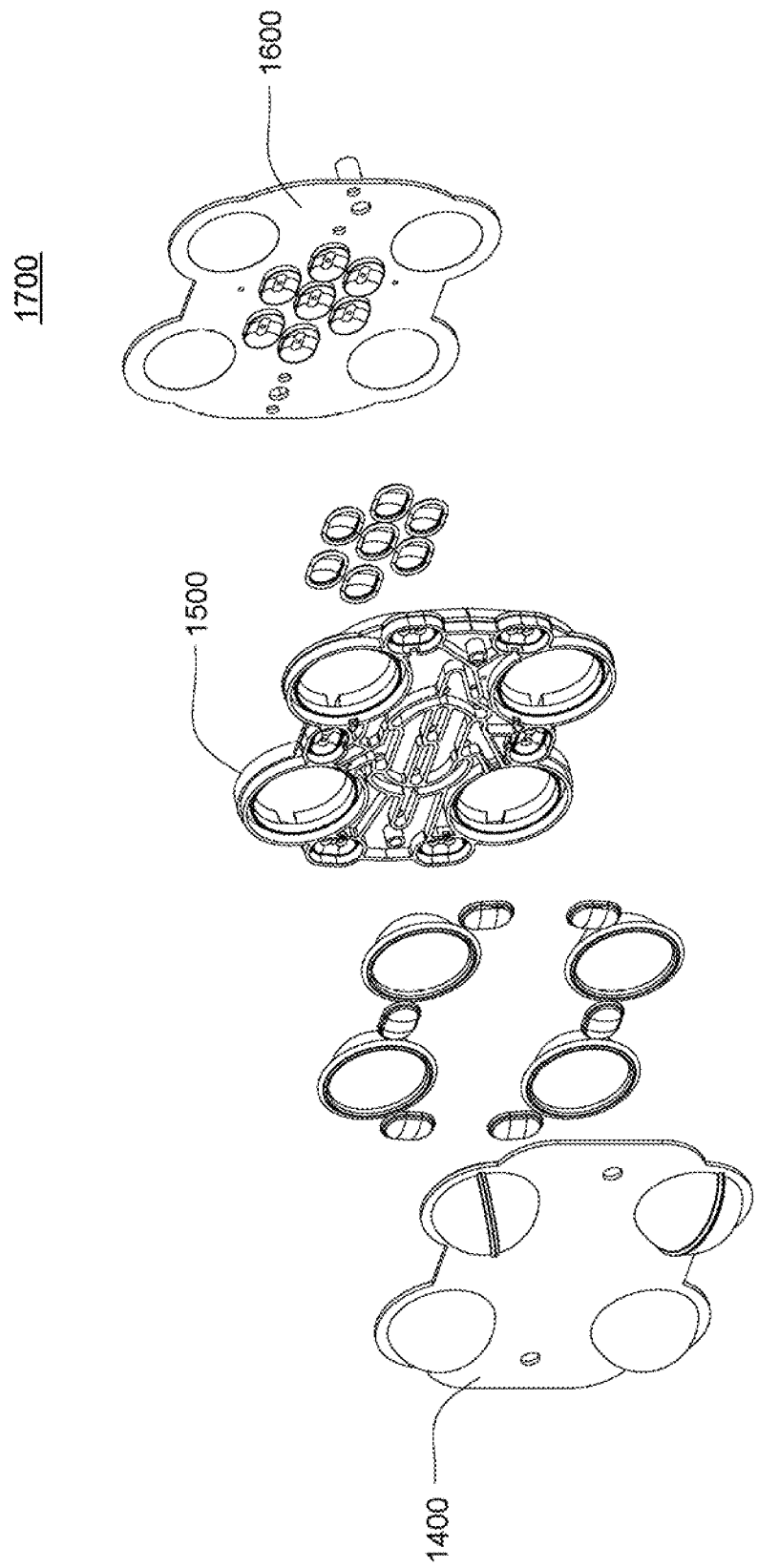
FIG. 17C is an exploded view of the assembled alternate embodiment of the cassette.
Figure 17D:
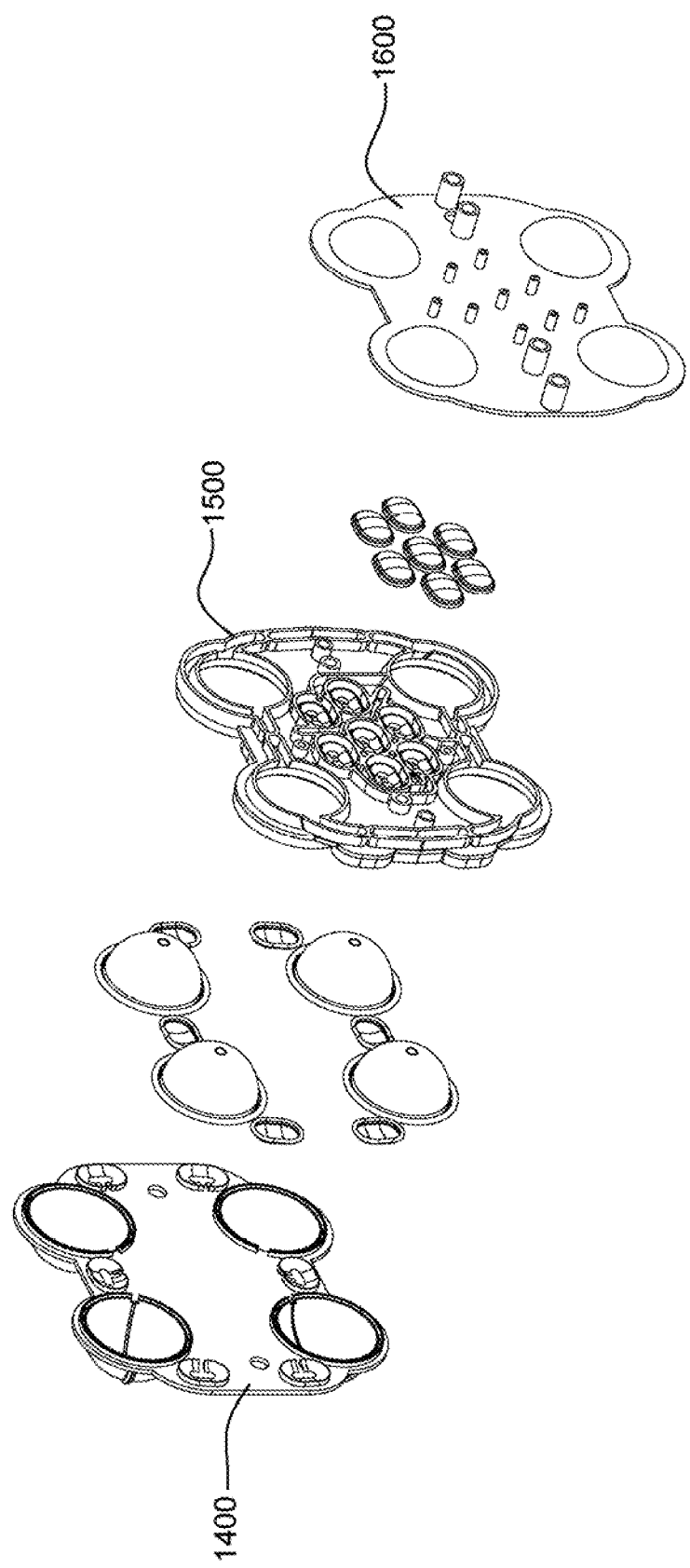
FIG. 17D is an exploded view of the assembled alternate embodiment of the cassette.
Figure 17E:
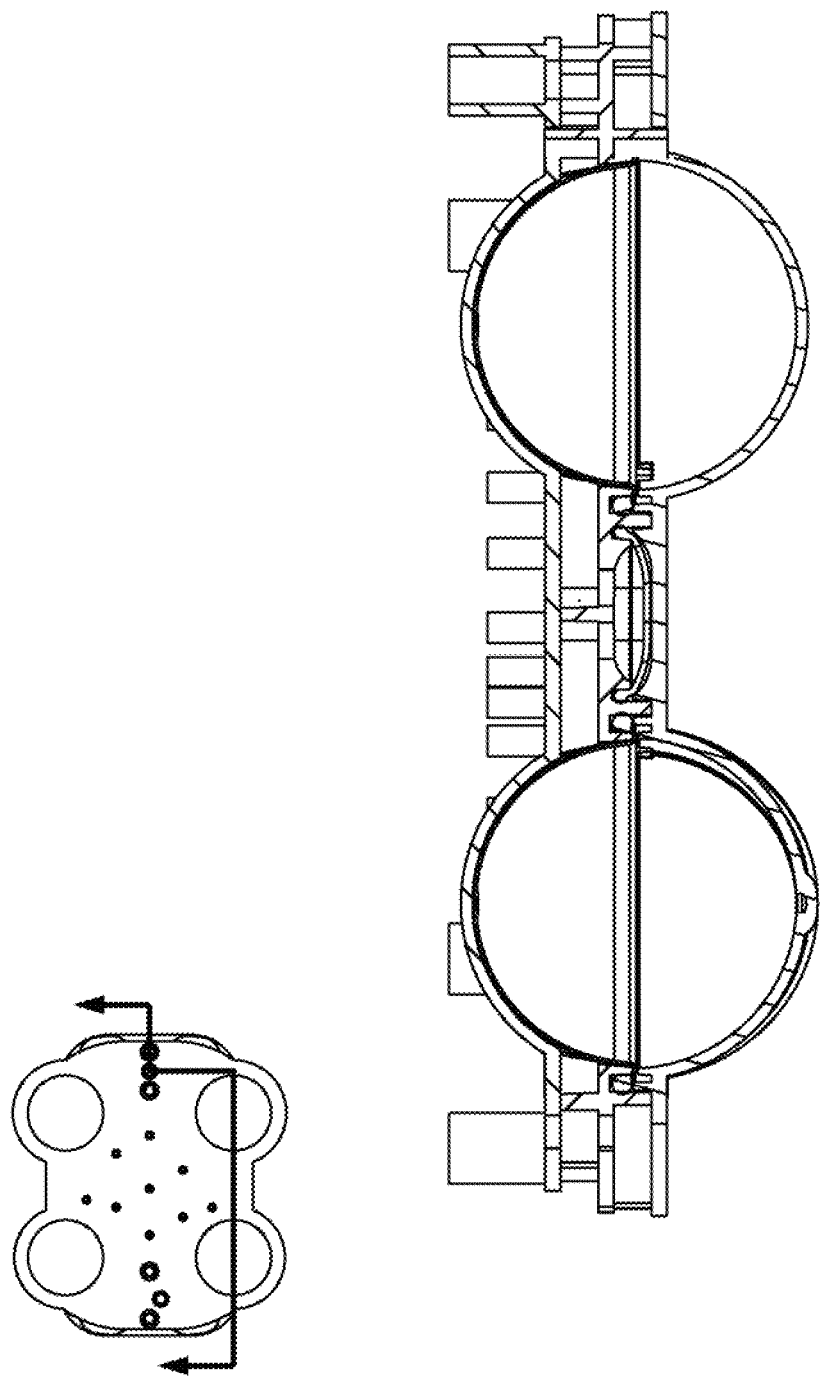
FIG. 17E shows a cross sectional view of the exemplary embodiment of the assembled cassette.
Figure 18A:
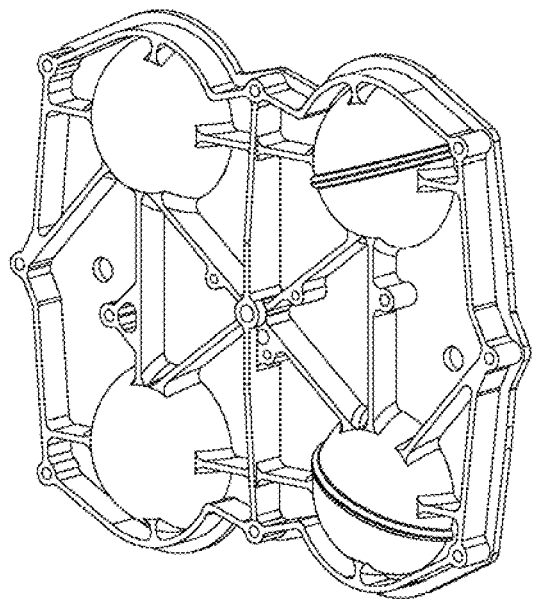
FIGS. 18A-18B show isometric and top views of an alternate embodiment of the top plate according to an alternate embodiment of the cassette.
Figure 18B:
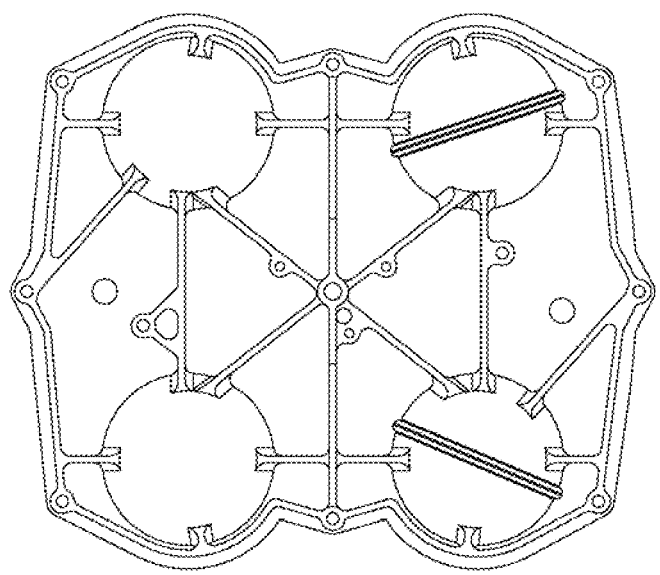
Figure 18C:
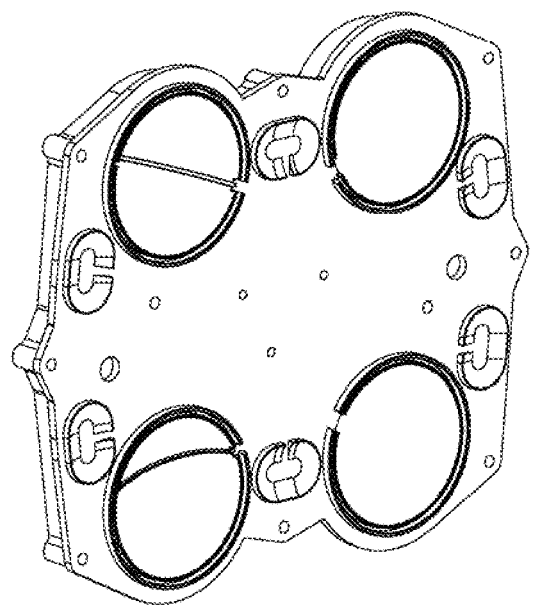
FIGS. 18C-18D show isometric and bottom views of an alternate embodiment of the top plate according to an alternate embodiment of the cassette.
Figure 18D:
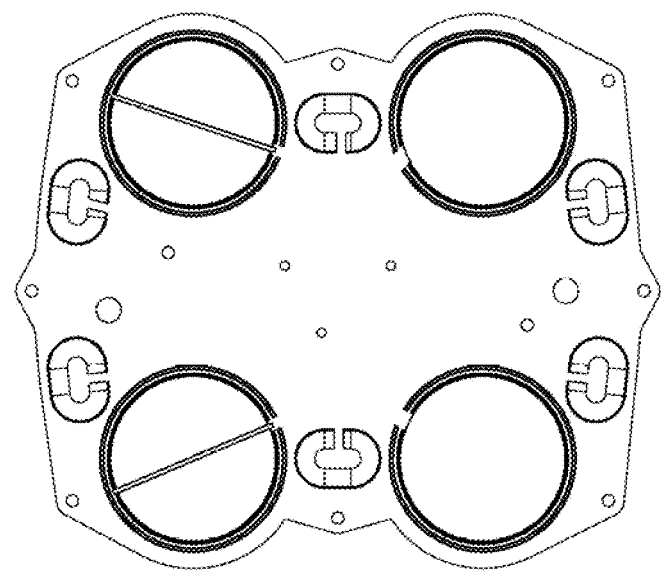
Figure 18E:
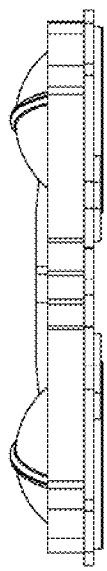
FIG. 18E shows a side view of the alternate embodiment of the top plate.
Figure 19A:
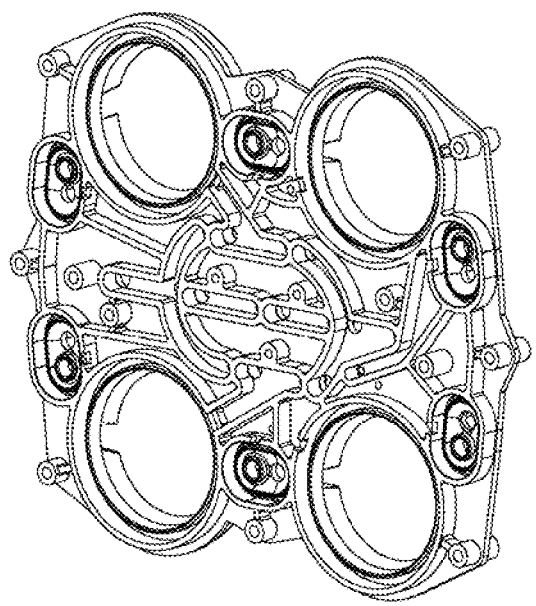
FIGS. 19A-19B show isometric and top views of an alternate embodiment of the midplate according to an alternate embodiment of the cassette.
Figure 19B:
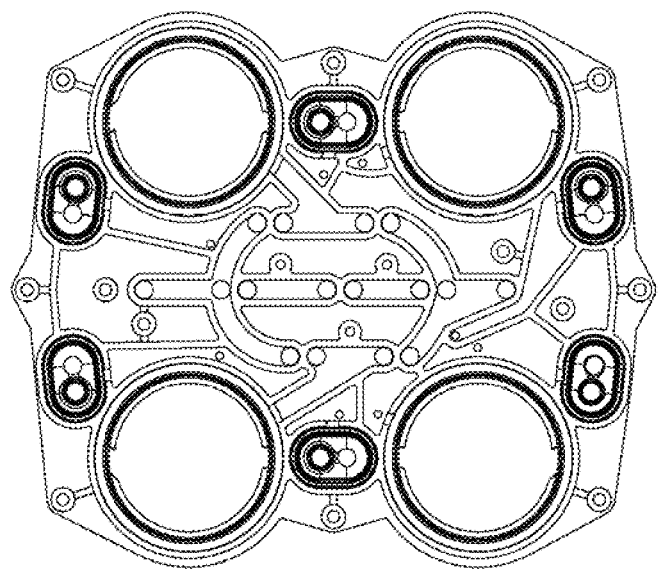
Figure 19C:
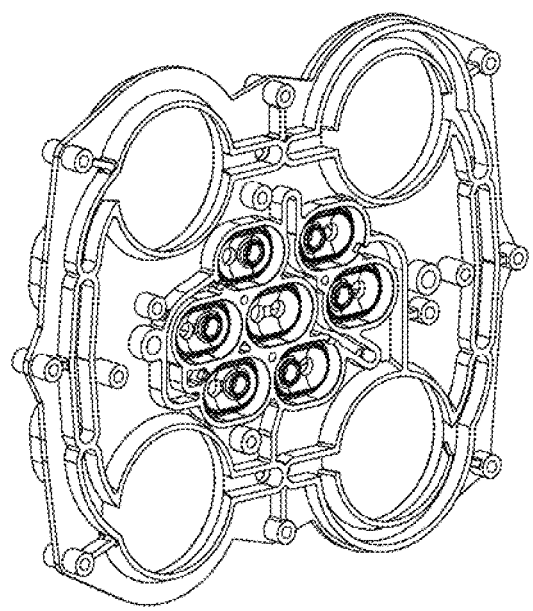
FIGS. 19C-19D show isometric and bottom views of an alternate embodiment of the midplate according to an alternate embodiment of the cassette.
Figure 19D:
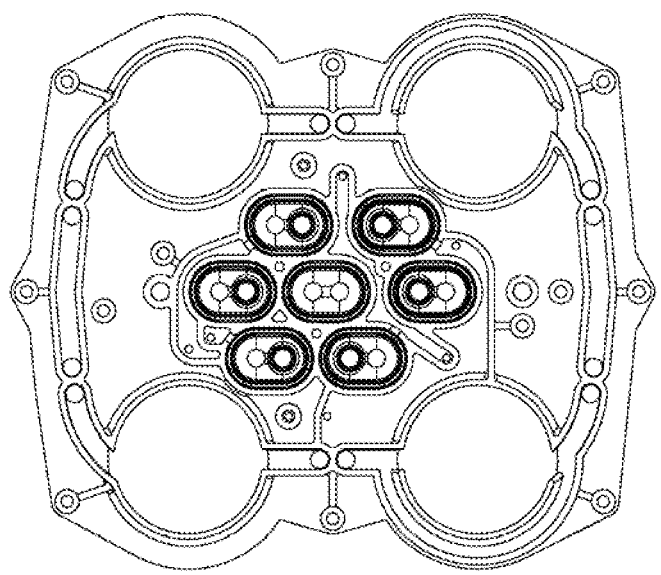
Figure 19E:
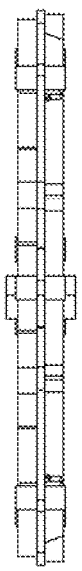
FIG. 19E shows a side view of the alternate embodiment of the midplate.
Figure 20A:
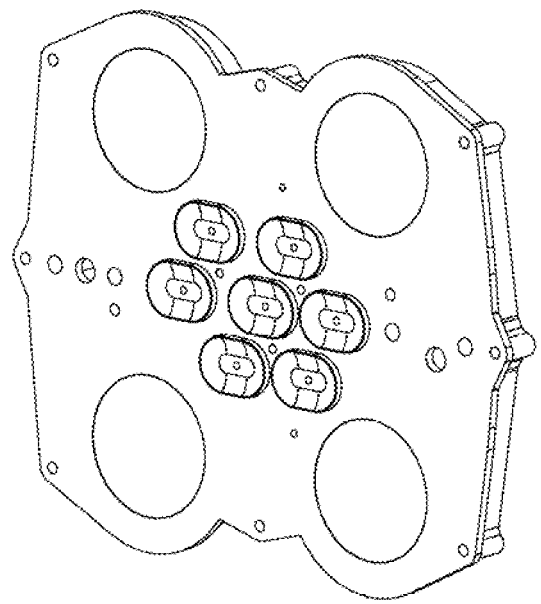
FIGS. 20A-20B show isometric and top views of an alternate embodiment of the bottom plate according to an alternate embodiment of the cassette.
Figure 20B:
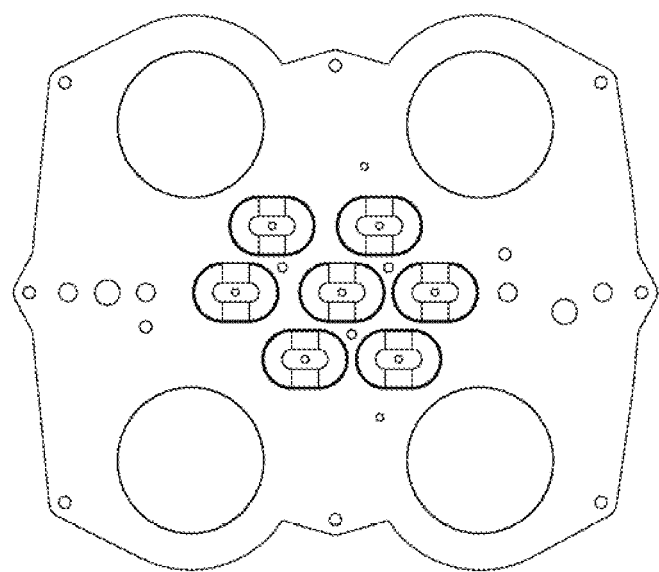
Figure 20C:
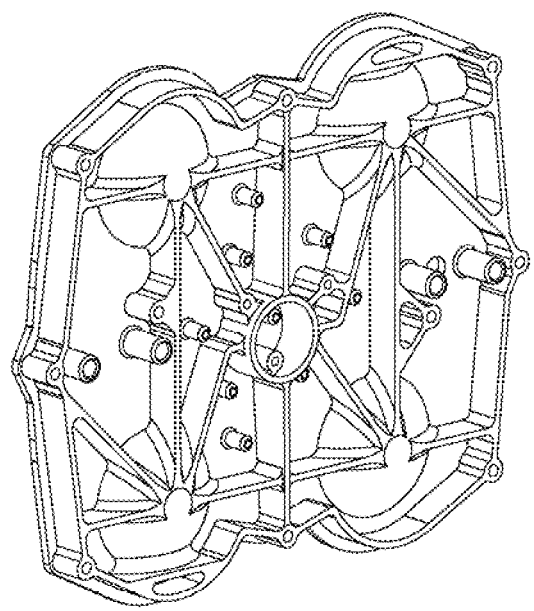
FIGS. 20C-20D show isometric and bottom views of an alternate embodiment of the bottom plate according to an alternate embodiment of the cassette.
Figure 20D:
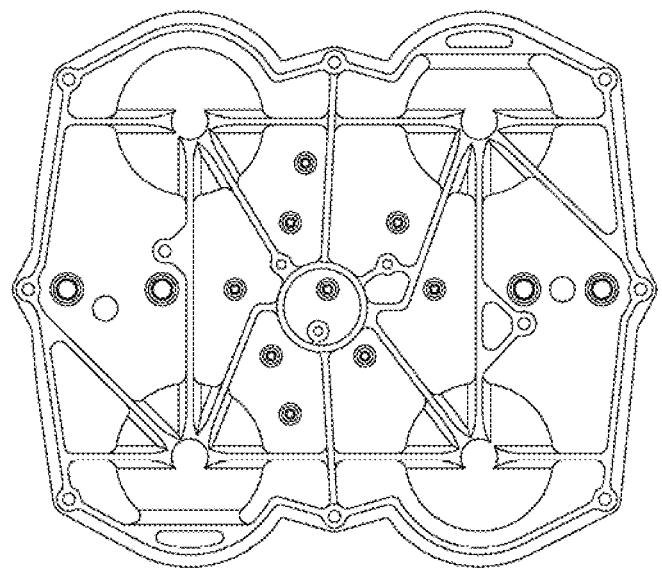
Figure 20E:
FIG. 20E shows a side view of the alternate embodiment of the bottom plate.
Figure 21A:
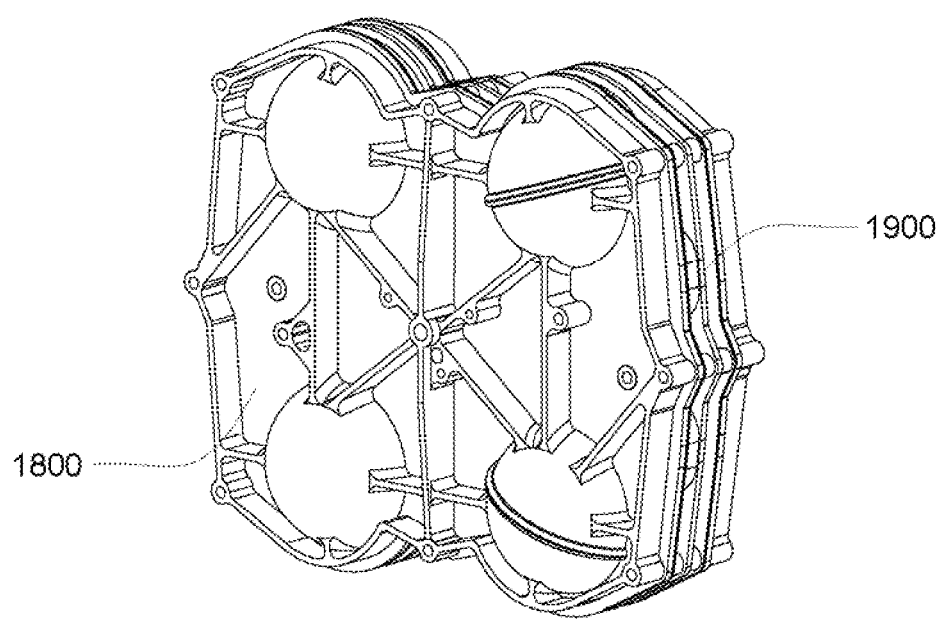
FIG. 21A is a top view of an assembled alternate embodiment of the cassette.
Figure 21B:
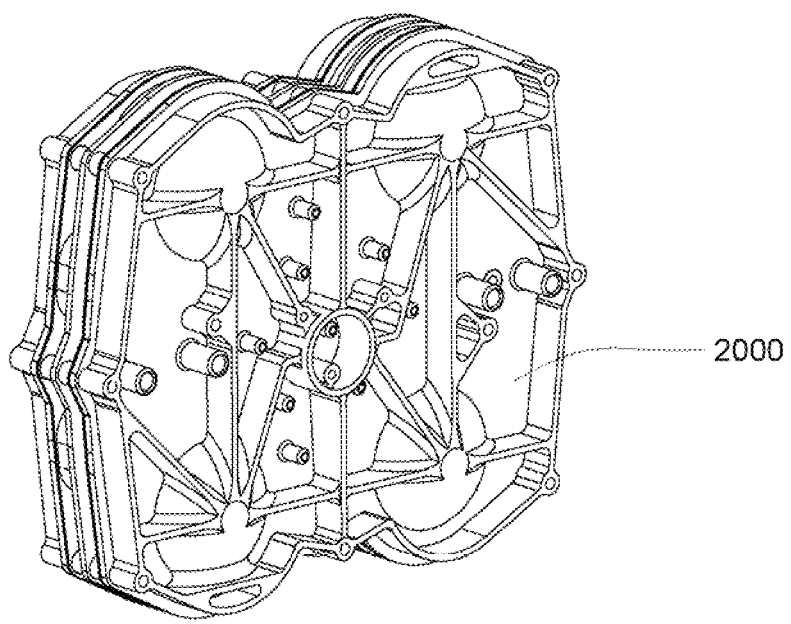
FIG. 21B is a bottom view of an assembled alternate embodiment of the cassette.
Figure 21C:
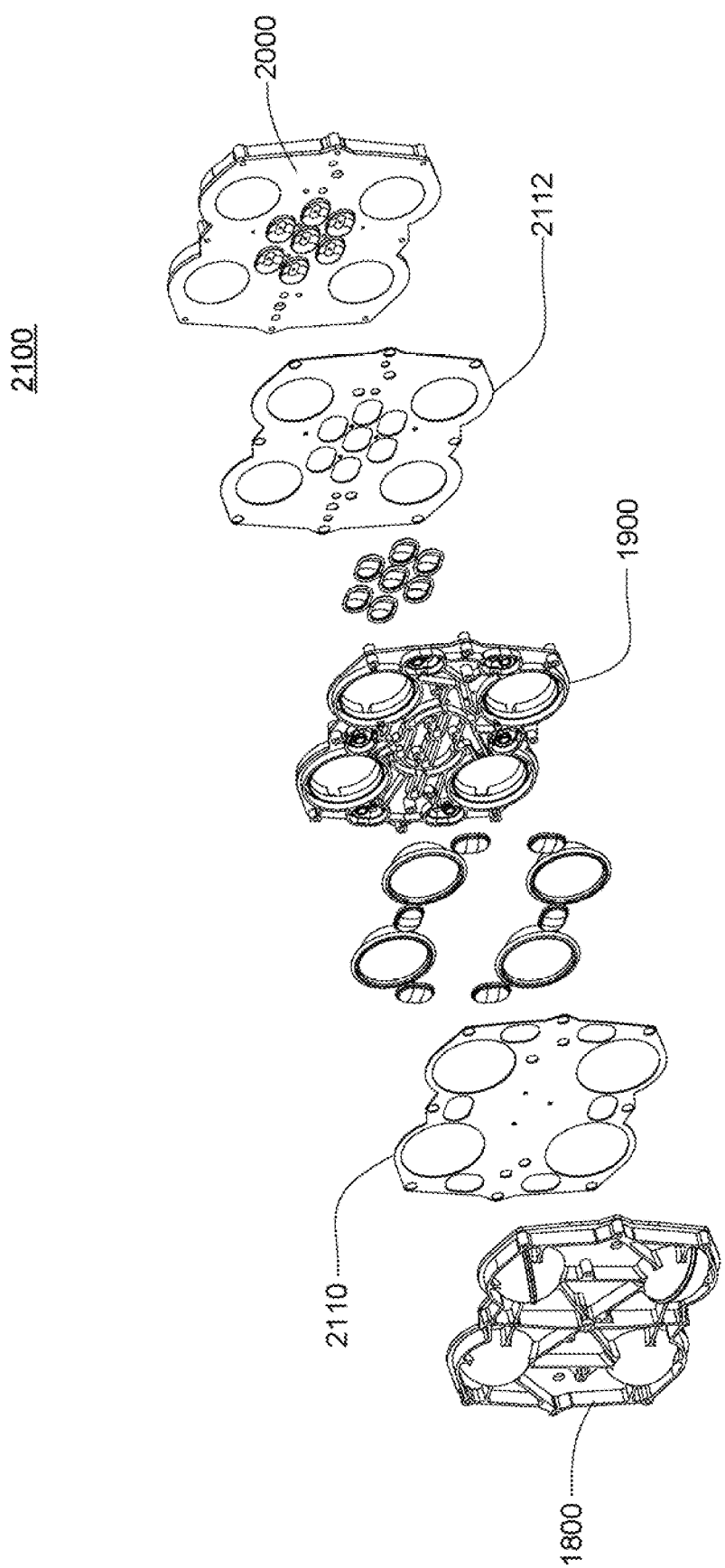
FIG. 21C is an exploded view of the assembled alternate embodiment of the cassette.
Figure 21D:
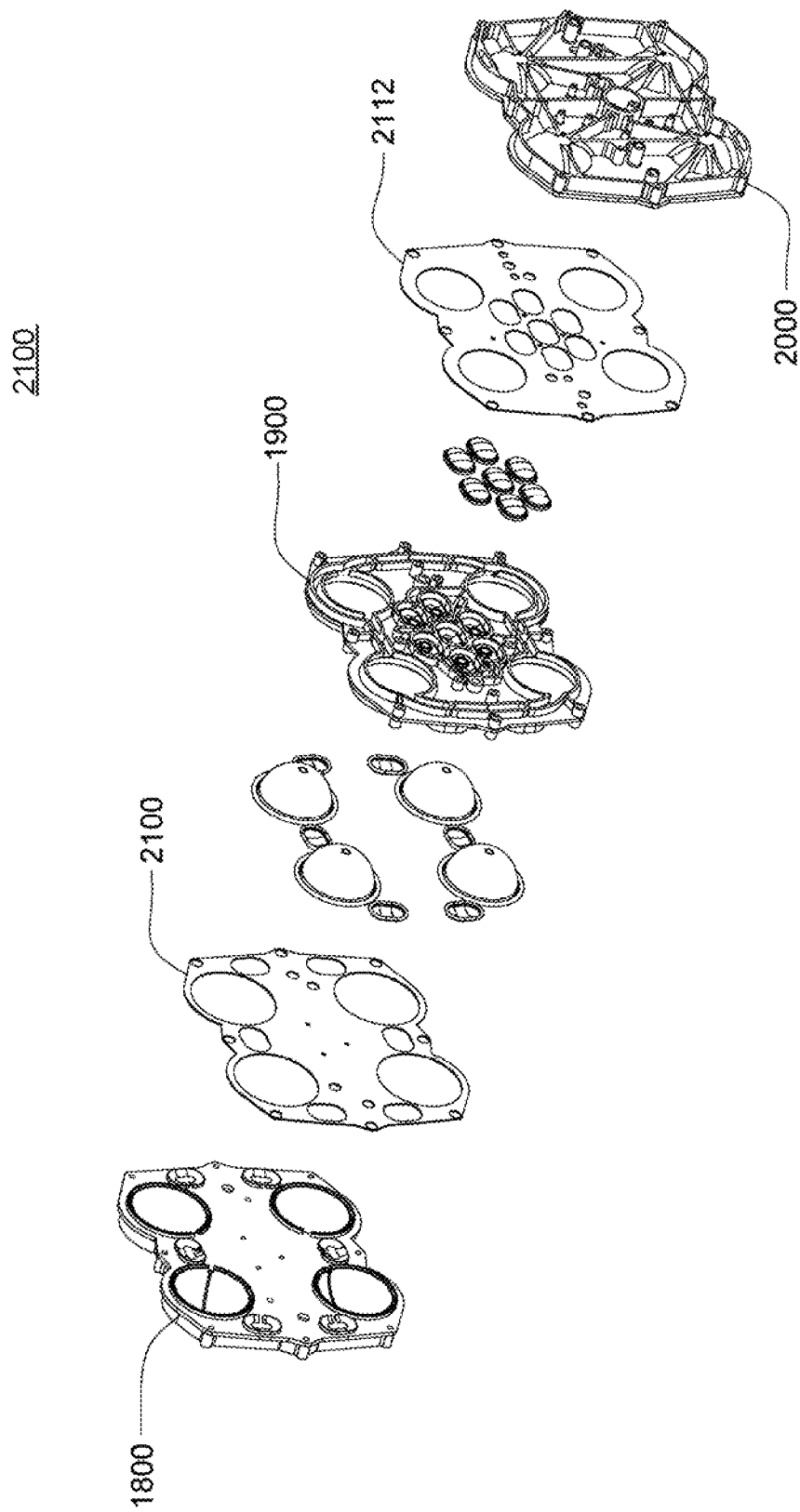
FIG. 21D is an exploded view of the assembled alternate embodiment of the cassette.
Figure 22B:
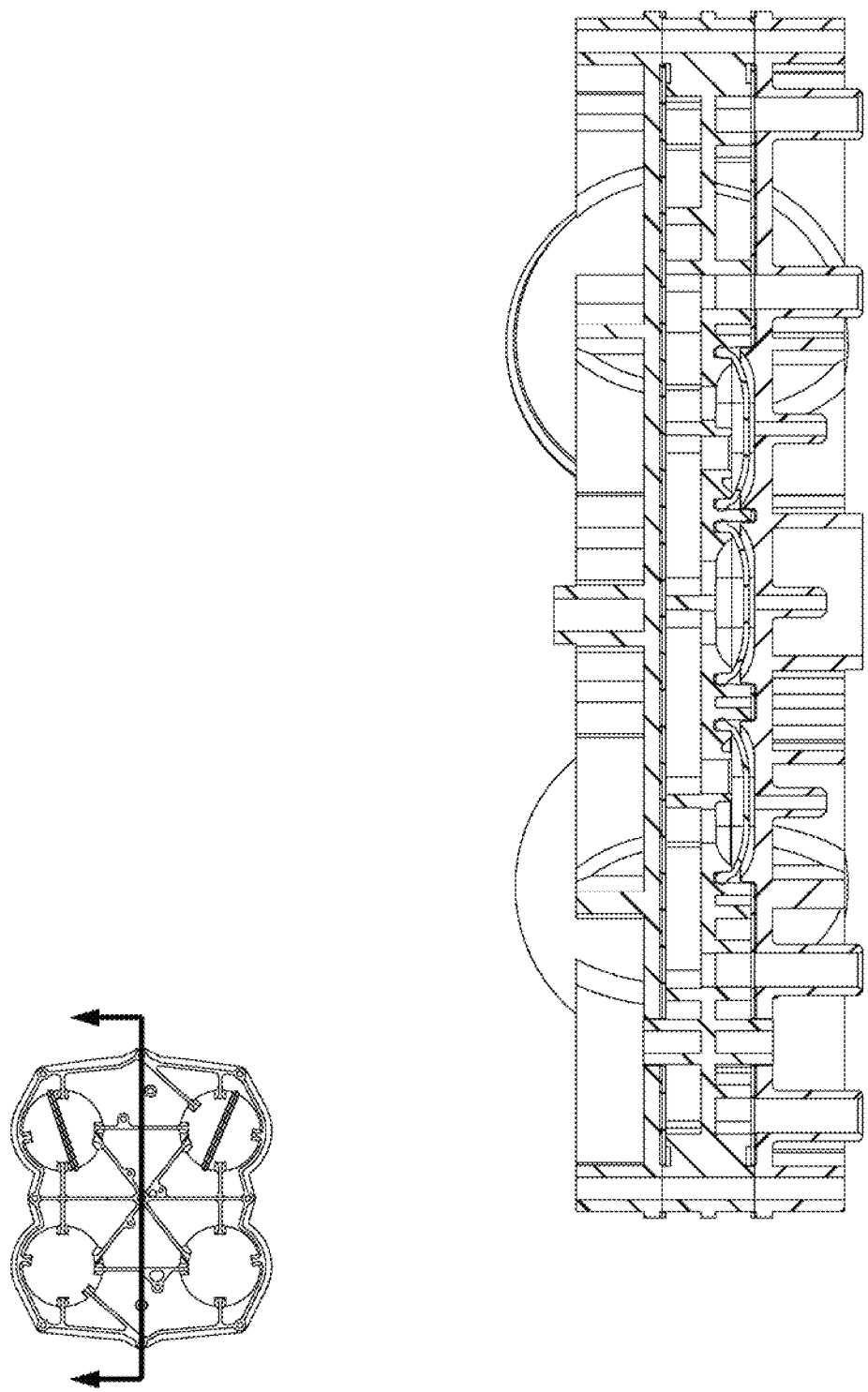
FIG. 22B shows a cross sectional view of the exemplary embodiment of the assembled cassette.

Referring now to FIGS. 17A-17B, an assembled alternate embodiment of the cassette 1700 is shown. FIGS. 17C-17D show exploded views of the cassette 1700. FIG. 17E is a cross sectional view of the assembled cassette 1700.

Referring now to FIGS. 18A-22B, another alternate embodiment of the cassette is shown. In this embodiment, when the cassette is assembled, as shown in FIGS. 21A-21B, the plates 1800, 1900, 2000 are sealed from each other using gaskets. Referring to FIGS. 21C-21D, the gaskets 2110, 2112 are shown. This embodiment additionally includes membranes (not shown). FIG. 22A is a cross sectional view of the assembled cassette, the gaskets 2110, 2112 relation to the assembled cassette assembly is shown.

5.3 Exemplary Embodiments of the Pumping Cassette

The pumping cassette can be used in a myriad of applications. However, in one exemplary embodiment, the pumping cassette is used to balance fluid going into the first fluid inlet and out the first fluid outlet with fluid coming into the cassette through the second fluid inlet and exiting the cassette through the second fluid outlet (or vice versa). The pumping cassette additionally provides a metering pump to remove a volume of fluid prior to that volume affecting the balancing pods or adds a volume of fluid prior to the fluid affecting the balancing pods.

The pumping cassette may be used in applications where it is critical that two fluid volumes are balanced. Also, the pumping cassette imparts the extra functionality of metering or bypassing a fluid out of the fluid path, or adding a volume of the same fluid or a different fluid into the fluid path. The flow paths shown in the schematic are bi-directional, and various flow paths may be created by changing the valve locations and or controls, or adding or removing valves. Additionally, more metering pumps, pod pumps and/or balancing pods may be added, as well as, more or less fluid paths and valves. Additionally, inlets and outlets may be added as well, or the number of inlets or outlets may be reduced.

One example is using the pumping cassette as an inner dialysate cassette as part of a hemodialysis system. Clean dialysate would enter the cassette through the first fluid inlet and pass through the sensor elements, checking if the dialysate is at the correct concentration and/or temperature. This dialysate would pass through the balancing pods and be pumped through the first fluid outlet and into a dialyzer. The second fluid in this case is used or impure dialysate from the dialyzer. This second fluid would enter through the second fluid inlet and balance with the clean dialysate, such that the amount of dialysate that goes into the dialyzer is equal to the amount that comes out.

The metering pump may be used to remove additional used dialysate prior to that volume being accounted for in a balancing pod, thus, creating a "false" balancing chamber through an ultra filtration ("UF") bypass. The situation is created where less clean dialysate by a volume equaled to the bypassed volume will enter the dialyzer.

In this embodiment, the valves controlling fluid connections to the balancing chambers shall be oriented such that the volcano feature of the valve is on the fluid port connected to the balancing chamber. This orientation directs most of the fluid displaced by the valve as it is thrown away from the balancing chamber.

The valves controlling fluid connections to the UF pump shall be oriented such that the volcano feature of the valve is on the fluid port connected to the pumping chamber. In the exemplary embodiment, the nominal stroke volume of each inside dialysate pump chamber shall be 38 ml. The nominal volume of each balancing pod shall be 38 ml. The stroke volume of the UF pump shall be 1.2 ml+/−0.05 ml. The inner dialysate pump low-pressure pneumatic variable valves shall vent to ambient atmospheric pressure. This architecture feature minimizes the chance that dissolved gas will leave the dialysate while inside of the balancing chambers. Other volumes of pod pumps, balancing chambers and metering pumps are easily discernable and would vary depending on the application. Additionally, although the embodiment described discusses venting to ambient, in other applications, negative pressure can be administered.

In various embodiments of the cassette, the valve architecture varies in order to alter the fluid flow path. Additionally, the sizes of the pod pumps, metering pump and balancing pods may also vary, as well as the number of valves, pod pumps, metering pumps and balancing pods. Although in this embodiment, the valves are volcano valves, in other embodiments, the valves are not volcano valves and in some embodiments are smooth surface valves.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A pumping cassette comprising:
a housing comprising a first fluid line including a first fluid inlet and a first fluid outlet for a first liquid flowpath configured to contain a first liquid, and a second fluid line including a second fluid inlet and a second fluid outlet for a second liquid flowpath configured to contain a second liquid;
a first and a second balancing pods within said housing and in fluid communication with said fluid lines, each one of said first and second balancing pods defining a cavity in which a flexible membrane is disposed, said flexible membrane dividing the cavity between a first chamber and a second chamber, the first chamber in fluid communication with the first fluid line, and the second chamber in fluid communication with the second fluid line, wherein said second chamber is configured to receive a first volume of the second liquid from the second fluid line by expelling a substantially equal volume of the first liquid from the first chamber into the first fluid line; and
a first and a second reciprocating positive displacement membrane pumps within said housing, each one of said first and second membrane pumps comprising an actuation chamber separated from a pumping chamber by a flexible membrane, wherein each one of said first and second membrane pumps is in fluid communication with the second fluid line, wherein the first membrane pump is configured to deliver in a pump stroke a volume of the second liquid into the second chamber of the first balancing pod, and wherein the second membrane pump is configured to deliver in a pump stroke a volume of the second liquid into the second chamber of the second balancing pod.

2. The cassette of claim 1, further comprising a metering pump within said housing and fluidly connected to said first or second fluid lines, wherein said metering pump is configured to pump a volume of the first or the second liquid such that pumped liquid bypasses the first and the second balancing pods.

3. The cassette of claim 2, wherein said first and second reciprocating positive displacement membrane pumps and said metering pump are pneumatically actuated membrane pumps.

4. The cassette of claim 1, wherein each one of said first and second reciprocating positive displacement pumps comprises:
- a curved rigid chamber wall; and
- a flexible membrane attached to an interior surface of the rigid chamber wall, wherein said flexible membrane separates a cavity defined by the curved rigid chamber wall into a pumping chamber and an actuation chamber.

5. The cassette of claim 1, wherein said cassette housing comprises a top plate, a mid-plate, and a bottom plate.

6. The cassette of claim 1 further comprising at least a first fluid valve in the first fluid line between the first fluid inlet and the first or the second balancing pod, and at least a second fluid valve in the second fluid line between the second fluid outlet and the first or the second balancing pod.

7. The cassette of claim 6, wherein said at least first and second fluid valves are membrane valves, each comprising a valve housing in which a membrane is disposed, the membrane separating the valve housing into a valving chamber in fluid communication with the first or the second fluid lines, and an actuation chamber for connection to a source of positive or negative pressure.

8. The cassette of claim 7, wherein said valving chamber comprises a raised valve seat configured to contact the valve membrane.

9. The cassette of claim 7, wherein said valving chamber comprises a valve seat configured to contact the valve membrane, said valve seat having a substantially smooth surface.

10. The cassette of claim 6, wherein said at least first fluid valve is a check valve.

* * * * *